United States Patent
Whitlock et al.

(10) Patent No.: US 11,945,799 B2
(45) Date of Patent: Apr. 2, 2024

(54) 4-ETHYNYLPYRIDINE DERIVATIVES USEFUL AS GCN2 INHIBITORS

(71) Applicant: IP2IPO INNOVATIONS LIMITED, London (GB)

(72) Inventors: Gavin Whitlock, Deal (GB); Matthew Fuchter, London (GB)

(73) Assignee: IP2IPO INNOVATIONS LIMITED, London (GB)

(*) Notice: Subject to any disclaimer, the term of this patent is extended or adjusted under 35 U.S.C. 154(b) by 0 days.

(21) Appl. No.: 18/191,772

(22) Filed: Mar. 28, 2023

(65) Prior Publication Data

US 2023/0250082 A1 Aug. 10, 2023

Related U.S. Application Data

(63) Continuation of application No. 18/001,317, filed as application No. PCT/GB2021/051428 on Jun. 9, 2021.

(30) Foreign Application Priority Data

Jun. 9, 2020 (GB) ..................... 2008749

(51) Int. Cl.
| | |
|---|---|
| A61K 45/06 | (2006.01) |
| C07D 401/06 | (2006.01) |
| C07D 401/14 | (2006.01) |
| C07D 471/04 | (2006.01) |
| C07D 487/04 | (2006.01) |
| C07D 513/04 | (2006.01) |

(52) U.S. Cl.
CPC ............ *C07D 401/14* (2013.01); *A61K 45/06* (2013.01); *C07D 401/06* (2013.01); *C07D 471/04* (2013.01); *C07D 487/04* (2013.01); *C07D 513/04* (2013.01)

(58) Field of Classification Search
CPC .. C07D 401/14; C07D 401/06; C07D 471/04; C07D 487/04; C07D 513/04; A61K 45/06; A61K 31/444; A61K 31/506; A61K 31/519; A61P 35/00
See application file for complete search history.

(56) References Cited

U.S. PATENT DOCUMENTS

| | | | |
|---|---|---|---|
| 7,037,927 B2 | 5/2006 | Lee et al. | |
| 7,595,332 B2 | 9/2009 | Lee et al. | |
| 8,546,413 B2 | 10/2013 | Marchionni et al. | |
| 8,969,366 B2 | 3/2015 | Marchionni et al. | |
| 9,409,914 B2 | 8/2016 | Dorsch et al. | |
| 9,604,980 B2 | 3/2017 | Menichincheri et al. | |
| 9,617,266 B2 | 4/2017 | Hoelzemann et al. | |
| 9,855,268 B2 | 1/2018 | Dorsch et al. | |
| 10,696,651 B2 | 6/2020 | Fujimoto et al. | |
| 10,793,563 B2 | 10/2020 | Bleich et al. | |
| 10,988,477 B2 | 4/2021 | Bayly et al. | |
| 11,046,699 B2 | 6/2021 | Bui et al. | |
| 2008/0146599 A1 | 6/2008 | Jones et al. | |
| 2008/0153838 A1 | 6/2008 | Jones et al. | |
| 2014/0073634 A1 | 3/2014 | Jones et al. | |
| 2015/0051202 A1 | 2/2015 | Schiemann et al. | |
| 2019/0169166 A1* | 6/2019 | Fujimoto ............. | A61K 31/444 |
| 2021/0040083 A1 | 2/2021 | Bleich et al. | |
| 2022/0274934 A1 | 9/2022 | Flynn et al. | |
| 2022/0340577 A1 | 10/2022 | Bayly et al. | |
| 2022/0388964 A1 | 12/2022 | Ramurthy et al. | |

FOREIGN PATENT DOCUMENTS

| | | |
|---|---|---|
| CN | 104829613 A | 8/2015 |
| CN | 105732614 A | 7/2016 |
| CN | 109790122 A | 5/2019 |
| EP | 3498693 A1 | 6/2019 |

(Continued)

OTHER PUBLICATIONS

Croucher, D.C. et al., "Longitudinal single-cell analysis of a myeloma mouse model identifies subclonal molecular programs associated with progression," Nature communications; 2021; 2 (1); p. 6322; 14 pages, doi 10.1038/s41467-021-26598-w.

CAS Registry No. 2375595-78-9, Aurora Fine Chemicals, Apr. 4, 2022, chemical name: N-{3-[2-(2-aminopyrimidin-5-yl)ethynyl]-2,4-difluorophenyl}-5-chloro-2-methoxypyridine-3-sulfonamide hydrochloride, 1 page.

CAS Registry No. 2375595-78-9, Acme Bioscience, Inc, Sep. 20, 2019, chemical name: 3-Pyridinesulfonamide, N-[3-[2-(2-amino-5-pyrimidinyl)ethynyl]-2,4-difluorophenyl]-5-chloro-2-methoxy-, hydrochloride (1:1), 1 page.

(Continued)

*Primary Examiner* — Savitha M Rao
*Assistant Examiner* — Andrew P Lee
(74) *Attorney, Agent, or Firm* — Haynes and Boone, LLP

(57) ABSTRACT

The invention provides compounds of formula I, wherein the substituents are as set out in further detail in the specification. The compounds are potent inhibitors of GCN2 and they have excellent pharmacokinetic properties. The compounds are useful for the treatment or prevention of a variety of conditions, particularly cancer. The invention further provides pharmaceutical compositions comprising the compounds of the invention and uses of the compounds and the compositions.

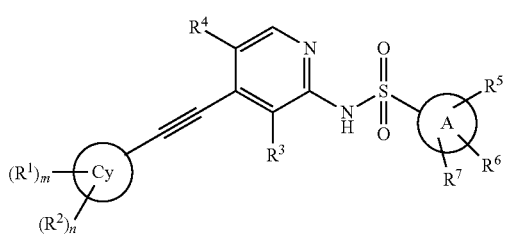

5 Claims, No Drawings

(56) References Cited

FOREIGN PATENT DOCUMENTS

| | | |
|---|---|---|
| JP | 2008-528662 A | 7/2008 |
| JP | 2012-530099 A | 11/2012 |
| JP | 2015-505541 A | 2/2015 |
| JP | 2016-510044 A | 4/2016 |
| JP | 2016-510045 A | 4/2016 |
| WO | 2005/040121 A2 | 5/2005 |
| WO | WO 2006/082371 A1 | 8/2006 |
| WO | 2006/082404 A1 | 10/2006 |
| WO | WO 2010/145998 A1 | 12/2010 |
| WO | WO 2013/110309 A1 | 8/2013 |
| WO | WO 2013/131609 A1 | 9/2013 |
| WO | 2014/031928 A2 | 2/2014 |
| WO | 2014/072220 A1 | 5/2014 |
| WO | WO 2014/135244 A1 | 9/2014 |
| WO | WO 2014/135245 A1 | 9/2014 |
| WO | WO 2018/030466 A1 | 2/2018 |
| WO | WO 2018/068739 A1 | 4/2018 |
| WO | WO 2019/148132 A1 | 8/2019 |
| WO | WO 2019/148136 A1 | 8/2019 |
| WO | WO 2019/236631 A1 | 12/2019 |
| WO | WO 2020/210828 A1 | 10/2020 |
| WO | 2021/155253 A1 | 8/2021 |
| WO | WO 2021/165346 A1 | 8/2021 |
| WO | WO 2021/222147 A1 | 11/2021 |
| WO | WO 2021/250399 A1 | 12/2021 |
| WO | WO 2022/109001 A1 | 5/2022 |
| WO | WO 2022/159745 A1 | 7/2022 |
| WO | WO 2022/159746 A1 | 7/2022 |

OTHER PUBLICATIONS

Castilho, B, A. et al., "Keeping the eIF2 alpha kinase Gen2 in check," Biochimica et Biophysica Acta 1843 (2014) 1948-1968.

Romano, P. R. et al., "Autophosphorylation in the Activation Loop Is Required for Full Kinase Activity In Vivo of Human and Yeast Eukaryotic Initiation Factor 2α Kinases PKR and GCN2," Mol Cell Biol, 1998, 18, 2282-2297.

Wek, S. A. et al., "The histidyl-tRNA synthetase-related sequence in the eIF-2 alpha protein kinase GCN2 interacts with tRNA and is required for activation in response to starvation for different amino acids," Mol Cell Biol, 1995, 15, 4497-4506.

Talloczy, Z. et al., "Regulation of starvation- and virus-induced autophagy by the eIF2α kinase signaling pathway," Proc Natl Acad Sci USA. 2002, 99, 190-195.

Wendgrod, J. et al., "Phosphorylation of eIF2α triggered by mTORC1 inhibition and PP6C activation is required for autophagy and is aberrant in PP6C-mutated melanoma," Sci Signal, 2015, 8, ra27, 12 pages.

B'chir, W. et al., "The eIF2α/ATF4 pathway is essential for stress-induced autophagy gene expression," Nucleic Acids Res., 2013, 41, 7683-7699.

Ye, J. et al., "GCN2 sustains mTORC1 suppression upon amino acid deprivation by inducing Sestrin2," Genes Dev., 2015, 29, 2331-2336.

Ravindran R. et al., "The amino acid sensor GCN2 controls gut inflammation by inhibiting inflammasome activation," Nature, 2016, 531, 523-527.

Wang, Y. et al., "Amino Acid Deprivation Promotes Tumor Angiogenesis through the GCN2/ATF4 Pathway," Neoplasia, 2013, 8, 989-997.

Ye, J. et al., "The GCN2-ATF4 pathway is critical for tumour cell survival and proliferation in response to nutrient deprivation," EMBO J, 2010, 29, 2082-2096.

Parzych, K et al., "The coordinated action of VCP/p97 and GCN2 regulates cancer cell metabolism and proteostasis during nutrient limitation," Oncogene, 2019, 28, 3216-3231.

Tameire, F. et al., "ATF4 couples MYC-dependent translational activity to bioenergetic demands during tumour progression," Nat. Cell. Biol., 2019, 21, 889-899.

Schmidt, S. et al., "A MYC-GCN2-eIF2α negative feedback loop limits protein synthesis to prevent MYC-dependent apoptosis in colorectal cancer," Nat. Cell. Biol., 2019, 21, 1413-1424.

Halaby, M. J. et al., "GCN2 drives macrophage and MDSC function and immunosuppression in the tumor microenvironment," Sci. Immunol, 2019, 4, 42, eaax8189, 18 pages.

Bunpo P, et al., "GCN2 Protein Kinase Is Required to Activate Amino Acid Deprivation Responses in Mice Treated with the Anti-cancer Agent l-Asparaginase," J. Biol. Chem., 2009, 284, 32742-32739.

Anthony, T. G. et al., "Preservation of Liver Protein Synthesis during Dietary Leucine Deprivation Occurs at the Expense of Skeletal Muscle Mass in Mice Deleted for eIF2 Kinase GCN2," J. Biol. Chem., 2004, 279, 36553-36561.

Zhang P. et al., "The GCN2 eIF2α Kinase Is Required for Adaptation to Amino Acid Deprivation in Mice," Mol. Cell. Biol., 2002, 22, 6681-6688.

Parzych, K. et al., "Inadequate fine-tuning of protein synthesis and failure of amino acid homeostasis following inhibition of the ATPase VCP/p97," Cell Death & Disease, 2015, 6, e2031, 11 pages.

Suraweera, A. et al., "Failure of Amino Acid Homeostasis Causes Cell Death following Proteasome Inhibition," Mol. Cell, 2012, 48, 242-253.

Vabulas, R. M. and Hartl F. U., "Protein Synthesis upon Acute Nutrient Restriction Relies on Proteasome Function," Science, 2005, 310, 1960-1963.

Nakamura, A. et al., "Inhibition of GCN2 sensitizes ASNS-low cancer cells to asparaginase by disrupting the amino acid response," PNAS, 2018, 115, 33, E7776-7785.

Berge, S. M., et al., "Pharmaceutical Salts," J. Pharm. Sci., 1977, 66, 1-19.

Li, Y. et al., "N-(3-Ethynyl-2,4-difluorophenyl)sulphonamide Derivatives as Selective Raf Inhibitors," ACS Medicinal Chemistry Letters, 2015, 6, 5, 543-547.

Chang, Y. et al., "Structure Based Design of N-(3-(1H-Pyrazolo[3,4-b]pyridin-5-yl)ethynyl)benzenesulfonamides as Selective Leucine-Zipper and Sterile-α Motif Kinase (ZAK) Inhibitors," Journal of Medicinal Chemistry, 2017, 60, 13, 5927-5932, 8 pages.

Wek. R. C. et al., "Coping with stress: eIF2 kinases and translational control," Biochem. Soc. Trans., 2006, 34, 1, 7-11.

Jackson, J. J., et al., "Potent GCN2 Inhibitor Capable of Reversing MDSC-Driven T Cell Suppression Demonstrates In Vivo Efficacy as a Single Agent and in Combination with Anti-Angiogenesis Therapy," J. Med. Chem., 2022, 65, 29, 12895-12924, 30 pages.

Fujimoto, J., et al., "Identification of novel, potent, and orally available GCN2 inhibitors with Type 1 half binding mode," ACS Medicinal Chemistry Letters 2019, vol. 10, pp. 1498-1503.

International Search Report for PCT/GB2021/051428 dated Aug. 5, 2021, 2 pages.

Office Action issued in Chinese Application No. 202180058556.4, dated Oct. 25, 2023.

* cited by examiner

4-ETHYNYLPYRIDINE DERIVATIVES USEFUL AS GCN2 INHIBITORS

CROSS REFERENCE TO RELATED APPLICATION

This application is a continuation of U.S. patent application Ser. No. 18/001,317, filed on Dec. 9, 2022, which is a 35 U.S.C. 371 National Phase Entry Application from PCT/GB2021/051428, filed Jun. 9, 2021, which claims priority to United Kingdom Patent Application No. 2008749.0, filed Jun. 9, 2020, the disclosures of which are incorporated herein in their entireties by reference, and priority is claimed to each of the foregoing.

FIELD OF THE INVENTION

The present invention relates to compounds of formula (I) and pharmaceutical compositions thereof, and their use as medicaments. The compounds of the invention are inhibitors of general control nonderepressible 2 (GCN2) and as such may be useful for the treatment or prevention of a variety of conditions, and particularly for use in the treatment of diseases, such as cancer.

BACKGROUND

The kinase general control nonderepressible 2 (GCN2), encoded by EIF2 AK4, is a pivotal regulator of cellular adaptations to amino acid shortages (Castilho, B. A., et al (2014) Biochim Biophys Acta 1843, 1948-1968). GCN2 is activated when uncharged tRNAs accumulate as a consequence of low amino acid levels (Romano, P. R., et al (1998) AutMol Cell Biol 18, 2282-2297; and Wek, S. A., et al (1995) Mol Cell Biol 15, 4497-4506). Activated GCN2 phosphorylates its only known target, the translation initiation factor eIF2α, resulting in attenuation of global protein synthesis. GCN2 also regulates Sestrin2-mediated repression of mTORC1 and induces autophagy (Talloczy, Z., et al (2002) Proc Natl Acad Sci USA 99, 190-195; Wengrod, J., et al (2015) Sci Signal 8, ra27; B'Chir, W., et al (2013) Nucleic Acids Res 41, 7683-7699; Ye, J., et al (2015) Genes Dev 29, 2331-2336; and Ravindran, R., et al (2016) Nature 531, 523-527). Together, these GCN2 effects promote the recovery of cells from amino acid shortages.

In solid tumours, GCN2 signalling is critical for cancer cell survival under conditions of nutrient deprivation (Wang, Y., et al (2013) Neoplasia 15, 989-997; Ye, J., et al (2010) EMBO J 29, 2082-2096; and Parzych, K., et al (2019) Oncogene 38, 3216-3231). GCN2 has also been shown to have a key role in MYC-driven tumour progression, by adapting protein synthesis to ensure that translation rates are compatible with the bioenergetic capacity and survival of cancer cells (Tameire, F., et al (2019) Nat Cell Biol 21, 889-899; and Schmidt, S., et al. (2019) Nat Cell Biol 21, 1413-1424). Moreover, some tumours may depend on myeloid GCN2 signals for protection from anti-cancer immune attacks (Halaby, M. J., et al (2019). Sci Immunol 4(42), eaax8189). GCN2 depletion enhances the anti-tumour effects of asparaginase treatment (Ye, J., et al (2010) EMBO J 29, 2082-2096; and Bunpo, P., et al (2009) J Biol Chem 284, 32742-32749). Importantly, mice deficient in GCN2 do not show gross pathologies unless they receive diets that lack essential amino acids (Anthony, T. G., et al (2004) J Biol Chem 279, 36553-36561; and Zhang, P., et al (2002) Mol Cell Biol 22, 6681-6688). Taken together, these data suggest that GCN2 inhibition may be an effective cancer therapy in a diverse range of cancers.

It has also been shown that proteasome inhibitors trigger intracellular amino acid shortage, and that this effect may be the main cause of multiple myeloma cell death upon proteasome inhibitor treatment (Parzych, K., et al (2015) Cell death & disease 6, e2031; Suraweera, A., et al (2012) Mol Cell 48, 242-253; and Vabulas, R. M., and Hartl, F. U. (2005) Science 310, 1960-1963). GCN2 inhibition is therefore predicted to be particularly effective in combination with proteasome inhibitors in the treatment of multiple myeloma.

There are very few known inhibitors of GCN2. WO 2018/030466 (Takeda Pharmaceutical Company Limited) discloses a series of GCN2 inhibitor compounds having an alkynyl-phenyl core. Other GCN2 inhibitor compounds are disclosed in Fujimoto, J. et al (2019) ACS Med. Chem. Lett 10(1), 1498-1503, and US published patent applications US 2019/0233411 and US 2019/0233425.

There is a need in the art for further GCN2 inhibitor compounds, in particular GCN2 inhibitor compounds that have high potency, and GCN2 inhibitor compounds that have good pharmacokinetic properties, such as good solubility, and therefore can be used as medicaments for the treatment of, for example, cancer.

SUMMARY

This invention provides a compound of formula (I) or a pharmaceutically acceptable ester, amide, carbamate or salt thereof, including a pharmaceutically acceptable salt of such an ester, amide or carbamate:

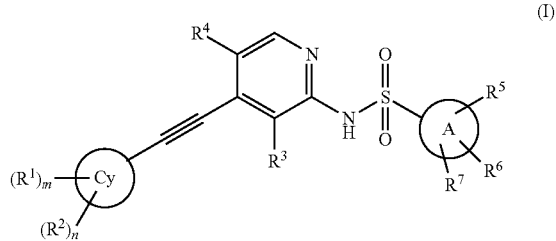

wherein
Cy is a 5-, 6-, 7-, 8-, 9- or 10-membered mono or bicyclic heteroaryl group comprising at least 1 N heteroatom and optionally 1, 2 or 3 further heteroatoms selected from the group consisting of N, S and O;
m is 0 or 1;
n is 0, 1 or 2;
when present, $R^1$ is selected from the group consisting of —$NH_2$; —$NR^A(C_{1-6}alkyl)$; —$NR^A(C_{1-6}alkyl$ substituted by 1, 2 or 3 groups independently selected from the group consisting of OH, halogen, and O—$C_{1-3}$ alkyl optionally substituted by 1, 2 or 3 halogen); —$NR^A(C(O)C_{1-6}alkyl$ optionally substituted by 1, 2 or 3 groups independently selected from the group consisting of OH, halogen and O—$C_{1-3}$ alkyl optionally substituted by 1, 2 or 3 halogen); —$NR^A(C_{0-3}alkyene-C_{3-6}cycloalkyl$, wherein said cycloalkyl is optionally substituted by 1, 2 or 3 groups independently selected from the group consisting of OH, halogen, $C_{1-3}$ alkyl optionally substituted by 1, 2 or 3 halogen, $C_{1-3}alkyl$-OH, and O—$C_{1-3}alkyl$ optionally substituted by 1, 2 or 3 halogen); —$NR^A(C_{0-3}alkyene-C_{3-6}heterocycloalkyl$, wherein said heterocycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen); —NR$^A$(C(O)C$_{3-6}$cycloalkyl optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen); and —NR$^A$ (5- or 6-membered heteroaryl group comprising at least 1 N heteroatom and optionally 1 or 2 further heteroatoms selected from the group consisting of N, S and O, wherein said 5- or 6-membered heteroaryl group is optionally substituted with 1 or 2 substituents independently selected from the group consisting of $C_{1-3}$alkyl optionally substituted by 1, 2 or 3 groups independently selected from the group consisting of halogen, OH and O—$C_{1-3}$alkyl optionally substituted by 1, 2 or 3 halogen; halogen; —O—$C_{1-3}$alkyl optionally substituted by 1, 2 or 3 groups independently selected from the group consisting of halogen, OH and O—$C_{1-3}$alkyl optionally substituted by 1, 2 or 3 halogen; OH; NH$_2$; NH($C_{1-6}$alkyl); N($C_{1-6}$alkyl)$_2$; cyano; $C_{3-4}$cycloalkyl optionally substituted by 1, 2, or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen).

when present, R$^A$ is selected from the group consisting of hydrogen; —$C_{1-6}$alkyl optionally substituted by 1, 2 or 3 groups independently selected from the group consisting of OH, halogen and O—$C_{1-3}$alkyl optionally substituted by 1, 2 or 3 halogen; —$C_{0-3}$alkyene-$C_{3-6}$cycloalkyl, wherein said cycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen; —$C_{0-3}$ alkyene-$C_{3-6}$heterocycloalkyl, wherein said heterocycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen; —C(O)$C_{3-6}$cycloalkyl optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen; —C(O)$C_{1-6}$alkyl optionally substituted by 1, 2 or 3 groups independently selected from the group consisting of OH, halogen and O—$C_{1-3}$alkyl optionally substituted by 1, 2 or 3 halogen; —C(O)$C_{3-6}$cycloalkyl optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen; and 5- or 6-membered heteroaryl group comprising at least 1 N heteroatom and optionally 1 or 2 further heteroatoms selected from the group consisting of N, S and O, wherein said 5- or 6-membered heteroaryl group is optionally substituted with 1 or 2 substituents independently selected from the group consisting of $C_{1-3}$alkyl optionally substituted by 1, 2 or 3 groups independently selected from the group consisting of halogen, OH and O—$C_{1-3}$alkyl optionally substituted by 1, 2 or 3 halogen; halogen; —O—$C_{1-3}$alkyl optionally substituted by 1, 2 or 3 groups independently selected from the group consisting of halogen, OH and O—$C_{1-3}$alkyl optionally substituted by 1, 2 or 3 halogen; OH; NH$_2$; NH($C_{1-6}$alkyl); N($C_{1-6}$alkyl)$_2$; cyano; $C_{3-4}$cycloalkyl optionally substituted by 1, 2, or 3 groups independently selected from the group consisting of OH, halogen, $C_{1-3}$alkyl optionally substituted by 1, 2 or 3 halogen, $C_{1-3}$alkyl-OH, and O—$C_{1-3}$alkyl optionally substituted by 1, 2 or 3 halogen;

when present, each R$^2$ is independently selected from the group consisting of oxo, $C_{1-6}$alkyl optionally substituted by 1, 2 or 3 groups independently selected from the group consisting of halogen, OH and O—$C_{1-3}$alkyl optionally substituted by 1, 2 or 3 halogen; halogen; —O—$C_{1-6}$alkyl optionally substituted by 1, 2 or 3 groups independently selected from the group consisting of halogen, OH and O—$C_{1-3}$alkyl optionally substituted by 1, 2 or 3 halogen; OH; =O; NH$_2$; NH($C_{1-6}$alkyl); N($C_{1-6}$alkyl)$_2$; cyano; and $C_{3-6}$cycloalkyl optionally substituted by 1, 2, or 3 groups independently selected from the group consisting of halogen, OH and O—$C_{1-3}$alkyl optionally substituted by 1, 2 or 3 halogen;

R$^3$ is halogen;

R$^4$ is selected from the group consisting of hydrogen and halogen;

A is selected from the group consisting of phenyl; naphthyl; and 5-, 6-, 7-, 8-, 9-, 10- or 11-membered heteroaryl group comprising 1 N heteroatom and optionally 1 or 2 further heteroatoms selected from the group consisting of N, S and O;

R$^5$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; O—$C_{1-6}$alkyl optionally substituted by 1, 2 or 3 groups independently selected from the group consisting of halogen, OH and O—$C_{1-3}$alkyl optionally substituted by 1, 2 or 3 halogen; NH$_2$; NH($C_{1-6}$alkyl); and N($C_{1-6}$alkyl)$_2$; and R$^6$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; O—$C_{1-6}$alkyl optionally substituted by 1, 2 or 3 groups independently selected from the group consisting of halogen, OH and O—$C_{1-3}$alkyl optionally substituted by 1, 2 or 3 halogen; NH$_2$; NH($C_{1-6}$alkyl); N($C_{1-6}$alkyl)$_2$; optionally substituted phenyl; optionally substituted naphthyl; optionally substituted 5-, 6-, 7-, 8-, 9-, 10- or 11-membered heteroaryl group comprising 1 N heteroatom and optionally 1 or 2 further heteroatoms independently selected from the group consisting of N, S and O (preferably N and S); optionally substituted 5-, 6-, 7-, 8-, 9-, 10- or 11-membered non-aromatic heterocycle group comprising 1 N heteroatom and optionally 1 or 2 further heteroatoms independently selected from the group consisting of N, S and O (preferably N and S); and optionally substituted $C_{3-10}$cycloalkyl; wherein said phenyl, naphthyl, 5-, 6-, 7-, 8-, 9-, 10- or 11-membered heteroaryl group, 5-, 6-, 7-, 8-, 9-, 10- or 11-membered non-aromatic heterocycle group, and $C_{3-11}$cycloalkyl are optionally substituted with 1, 2 or 3 groups independently selected from the group consisting of halogen; OH; $C_{1-3}$alkyl optionally substituted by 1, 2 or 3 groups independently selected from the group consisting of halogen, OH and O—$C_{1-3}$alkyl optionally substituted by 1, 2 or 3 halogen; O—$C_{1-3}$alkyl optionally substituted by 1, 2 or 3 groups independently selected from the group consisting of halogen, OH and O—$C_{1-3}$alkyl optionally substituted by 1, 2 or 3 halogen; and $R^7$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; $NH(C_{1-6}$alkyl); and $N(C_{1-6}$alkyl$)_2$.

The invention also provides a pharmaceutical composition comprising a compound of formula (I) and at least one pharmaceutically acceptable carrier or excipient.

The invention further provides a pharmaceutical composition comprising a compound of formula (I), wherein said composition further comprises at least one further therapeutic agent.

The invention further provides a compound according to formula (I) or a pharmaceutical composition comprising a compound of formula (I) for use as a medicament.

The invention further provides a compound according to formula (I) or a pharmaceutical composition comprising a compound of formula (I) for use in the treatment or prophylaxis of a disease or disorder in which the inhibition of GCN2 provides a therapeutic effect.

The invention further provides a compound according to formula (I) or a pharmaceutical composition comprising a compound of formula (I) for use in the treatment of a disease or disorder selected from the group consisting of: cancer (for example solid cancers and hematological cancers).

The invention further provides a method for the treatment or prophylaxis of a disease or disorder in which the inhibition of GCN2 provides a therapeutic effect in a mammal (for example the treatment or prophylaxis of cancer in a mammal), which comprises administering to the mammal a therapeutically effective amount of a compound according to formula (I) or a pharmaceutical composition comprising a compound of formula (I).

The invention further provides the use of a compound according to formula (I) for the manufacture of a medicament for the treatment or prophylaxis of a disease or disorder in which the inhibition of GCN2 provides a therapeutic effect (for example the treatment or prophylaxis of cancer).

Further advantageous features of various embodiments of the invention are defined in the dependent claims and within the detailed description below.

DETAILED DESCRIPTION

The invention provides compounds of formula (I) as defined above and pharmaceutical compositions comprising compounds of formula (I).

The compounds of the present invention have been found to be potent inhibitors of GCN2. Thus, the compounds of the present invention inhibit GCN2 activity and/or translation of initiation factor eIF2α, resulting in attenuation of global protein synthesis in a subject.

The compounds of the invention have excellent pharmacokinetic properties. In particular, they have good solubility in aqueous media. The compounds of the invention also have good bioavailability and very suitable 'drug-like' pharmacokinetic properties. Therefore, the present invention also provides therapeutic uses of the compounds of formula (I) and the pharmaceutical compositions comprising compounds of formula (I).

As mentioned in the introduction, WO 2018/030466 (Takeda Pharmaceutical Company Limited) discloses a series of GCN2 inhibitor compounds having an alkynylphenyl core. The compounds of the current invention have been found to have surprisingly superior properties compared with the compounds disclosed in a WO 2018/030466. As demonstrated by the data herein, the compounds of the current invention are significantly more soluble in aqueous media, and they also have strong potency in the inhibition of GCN2 activity.

Furthermore, the compounds of the current invention have been found by the current inventors to have good kinase selectivity for GCN2. The kinase selectivity of compounds of the current invention has been found by the current inventors, in a KINOMEscan™ assay, to be superior to the kinase selectivity of compounds of WO 2018/030466.

The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of Experimental Immunology" (D. M. Weir & C. C. Blackwell, eds., 1986); "Current Protocols in Molecular Biology" (F. M. Ausubel et al., eds., 1987, and periodic updates); and "Current Protocols in Immunology" (J. E. Coligan et al., eds., 1991), each of which is herein incorporated by reference in its entirety.

Various aspects of the invention are set forth below in sections; however, aspects of the invention described in one particular section are not to be limited to any particular section. Further, when a variable is not accompanied by a definition, the previous definition(s) of the variable may be applied.

Embodiments of the Invention

The present invention provides a compound according to the general formula (I) (for example, the compound is a compound of formula (IA) or (IB), as described below), or a pharmaceutically acceptable ester, amide, carbamate or salt thereof, including a pharmaceutically acceptable salt of such an ester, amide or carbamate:

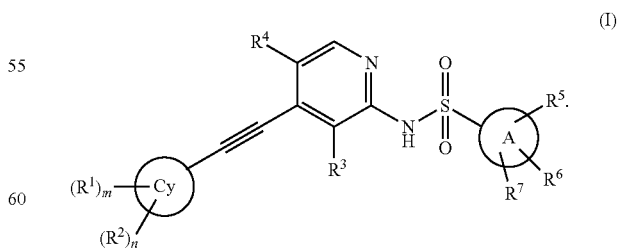

Depending upon the substituents present in the compounds of the invention, the compounds may exist as stereoisomers. In particular, the compounds of the invention may contain chiral (asymmetric) centres or the compounds as a whole may be chiral. All individual stereoisomers, as well as mixtures thereof, are included within the scope of the invention.

Diastereomeric mixtures can be separated into their individual diastereoisomers on the basis of their physical chemical differences by methods well known to those skilled in the art, such as, for example, chromatography and/or fractional crystallisation. Enantiomers can be separated by chiral HPLC column. Enantiomers can also be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolysing) the individual diastereomers to the corresponding pure enantiomers.

Isotopic forms, for example where a hydrogen atom is replaced with deuterium or tritium, or a carbon atom is replaced with a carbon-13 atom, are also included within the invention. Certain isotopic forms may have beneficial biological properties, for example improved metabolic stability or enhanced therapeutic activity over other isotopic forms; or a specific isotopic form may be useful for biological imaging purposes, for example, carbon-11, nitrogen-13, oxygen-15 or fluorine-18 isotopic variants may be used for positron emission tomography.

In one preferred embodiment, $R^4$ is hydrogen, i.e. the compound of the invention is a compound of formula (IA):

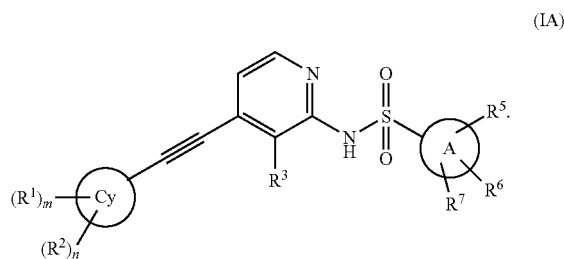

(IA)

In another especially preferred embodiment, the compound of the invention is a compound of formula (IB):

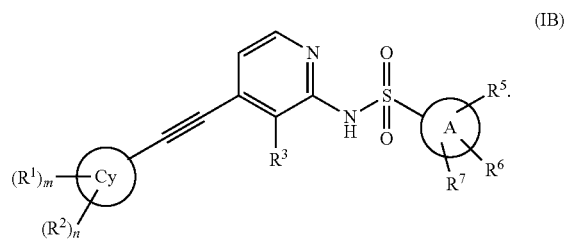

(IB)

Wherein:
m=0 or 1;
n=0
$R^1$ is amino;
Cy is a 5-, 6-, 7-, 8-, 9- or 10-membered mono or bicyclic heteroaryl group comprising at least 1 N heteroatom and optionally 1, 2 or 3 further heteroatoms selected from the group consisting of N, for example, pyrimidinyl, pyrazolopyridinyl, naphthyridinyl (for example, 1,7-naphthyridinyl and 1,6-naphthyridinyl), pyridopyrazinyl, pyrazolopyrimidinyl, imidazopyridyl, quinoxalinyl or imidazopyrazinyl.

$R^3$ is halogen, for example, F;
A is a 5-, 6-, 7-membered heteroaryl group comprising 1 N heteroatom and optionally 1 or 2 further heteroatoms selected from the group consisting of N, for example, pyridyl;
$R^5$ is halogen;
$R^6$ is O—$C_{1-3}$alkyl; and
$R^7$ is hydrogen.

In one embodiment, -A($R^5$, $R^6$, $R^7$) is 2-$C_{1-3}$alkoxy 5-halopyridyl, for example, 2-methoxy-5-chloropyrid-3-yl.

In the compounds of the invention, $R^3$ is halogen, for example, $R^3$ is F or Cl. In one preferred embodiment, $R^3$ is F.

In the compounds of the invention, $R^4$ is selected from the group consisting of hydrogen and halogen. In one preferred embodiment, $R^4$ is selected from the group consisting of hydrogen, F and Cl. In another preferred embodiment, $R^4$ is selected from the group consisting of hydrogen and F.

In one very preferred embodiment, $R^4$ is hydrogen.

In another very preferred embodiment, $R^3$ is F or Cl; and, $R^4$ is hydrogen.

In the compounds of the invention, Cy is a 5-, 6-, 7-, 8-, 9- or 10-membered heteroaryl group comprising at least 1 N heteroatom and optionally 1, 2 or 3 further heteroatoms selected from the group consisting of N, S and O (preferably N and S, more preferably N).

Preferably, Cy is a 5-, 6-, 7-, 8-, 9- or 10-membered heteroaryl group comprising at least 1 N heteroatom and optionally 1 or 2 further heteroatoms selected from the group consisting of N, S and O (preferably N and S, more preferably N).

In one preferred embodiment, Cy is a 5-, 6-, 7-, 8-, 9- or 10-membered heteroaryl group comprising at least 1 N heteroatom and optionally 1 or 2 further heteroatoms selected from the group consisting of N and S (preferably N). In another preferred embodiment, Cy is a 5- or 6-membered heteroaryl group comprising at least 1 N heteroatom and optionally 1 or 2 further heteroatoms selected from the group consisting of N and S (preferably N); or Cy is a 9- or 10-membered heteroaryl group comprising at least 1 N heteroatom and optionally 1 or 2 further heteroatoms selected from the group consisting of N and S (preferably N). In another preferred embodiment, Cy is a 5- or 6-membered heteroaryl group comprising at least 1 N heteroatom and optionally 1 or 2 further heteroatoms (preferably optionally 1 further heteroatom) selected from the group consisting of N and S (preferably N); or Cy is a 9- or 10-membered heteroaryl group comprising at least 2 N heteroatom and optionally 1 further heteroatom selected from the group consisting of N and 5 (preferably N).

In certain embodiments wherein Cy is a 5-, 6-, 7-, 8-, 9- or 10-membered heteroaryl group comprising at least 1 N heteroatom and optionally 1, 2 or 3 further heteroatoms selected from the group consisting of N, S and O, the heteroaryl may be selected from the group consisting of pyridyl (i.e., pyridinyl), pyrimidinyl, pyrazinyl, pyridazinyl, triazinyl, quinolyl, tetra hydroquinolyl, isoquinolyl, tetra hydroisoquinolyl, imidazolyl, thiazolyl, indolyl, pyrryl, oxazolyl, benzthiazolyl, isoxazolyl, pyrazolyl, triazolyl, indazolyl, 1,2,4-thiadiazolyl, isothiazolyl, benzimidazolyl (for example, benzo[a]imidazolyl), benzopyrazolyl (for example, benzo[e]pyrazolyl), benzopyridazinyl (for example, benzo[b]pyridazinyl, indoliny, pyridoimidazolyl (for example, pyrido[2,3-a]imidazolyl, pyrido[3,4-a]imidazole, pyrido[3,4-d]imidazole), pyridothiazolyl (for example, pyrido[3,4-d]thiazolyl), pyridopyrazolyl (for example, pyrido[3,4-c]pyrazolyl, pyrido[3,4-d]pyrazolyl or pyrido[3, 4-e]pyrazolyl) pridopyridyl (for example, pyrido[2,3-c]pyridyl) and pyrazinopyridyl (for example, pyrazino[2,3-c]pyridyl) I. In one especially preferred embodiment, Cy is a pyrimidinyl group.
In certain embodiments, preferably Cy is selected from the group consisting of:
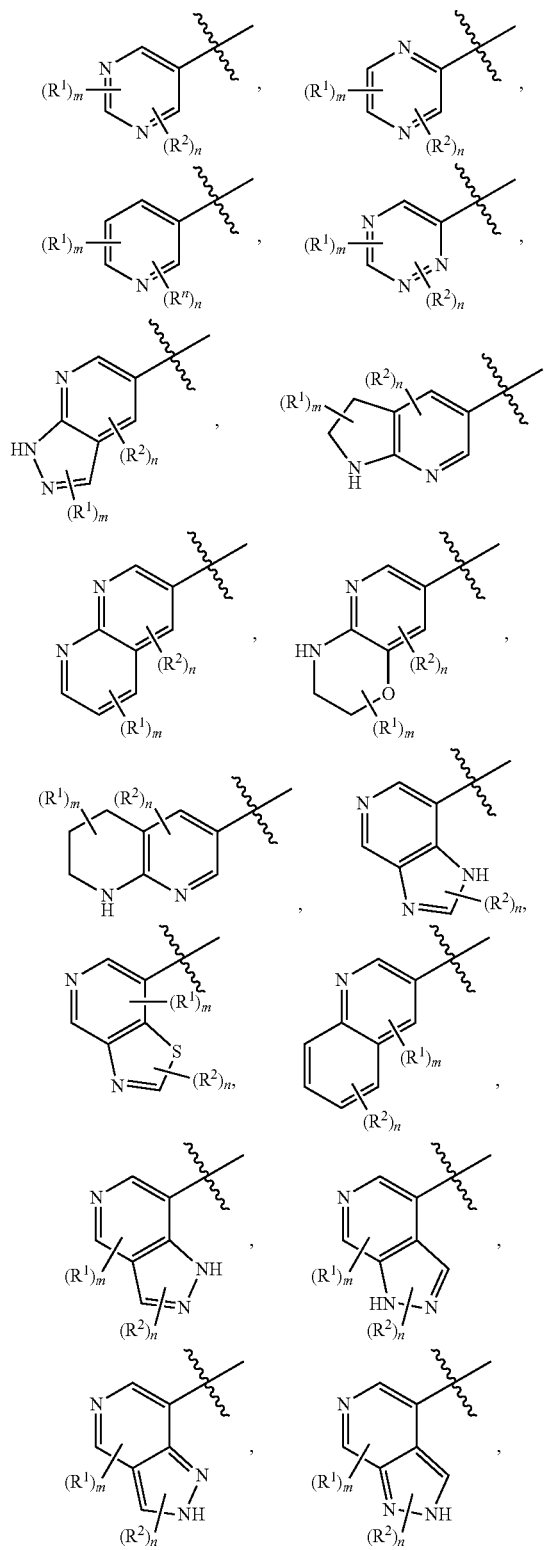
-continued
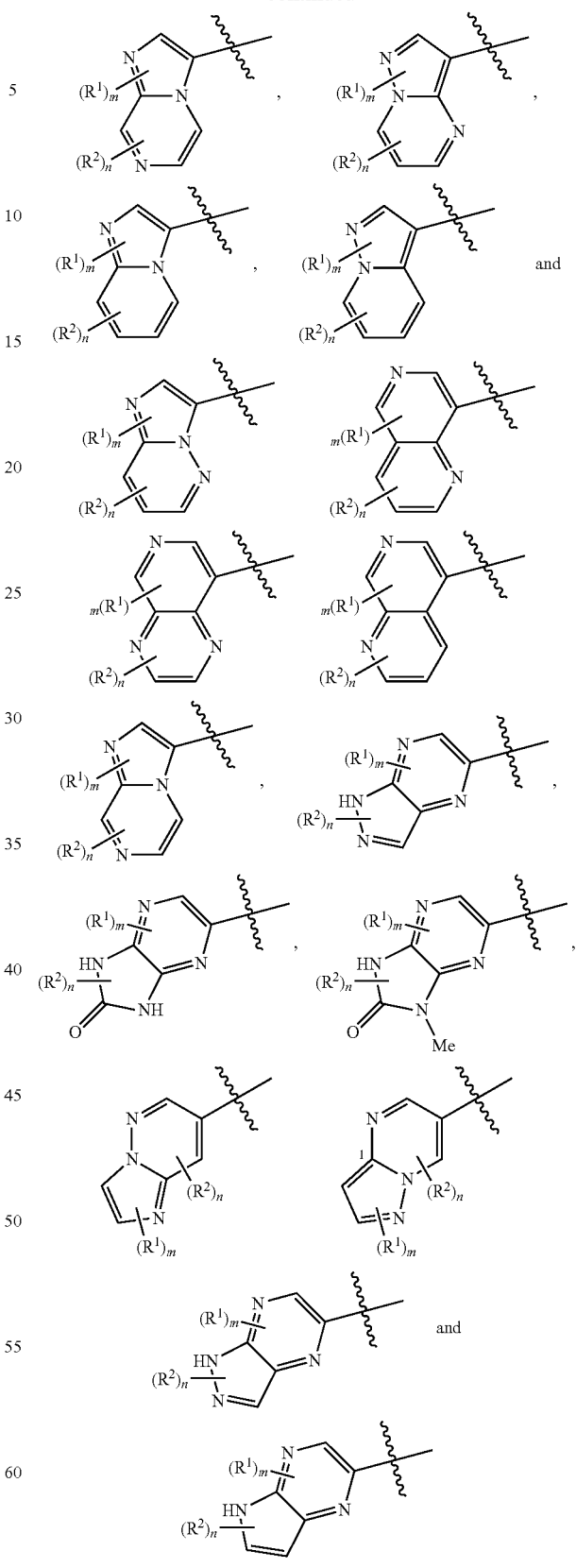
More preferably, Cy is selected from the group consisting of:

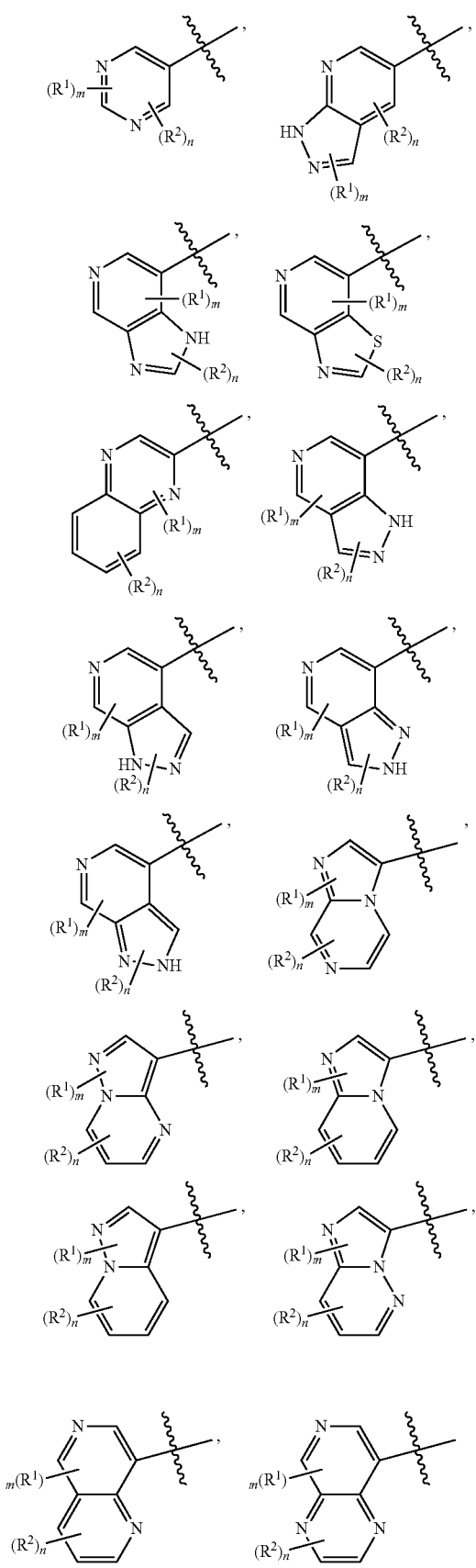
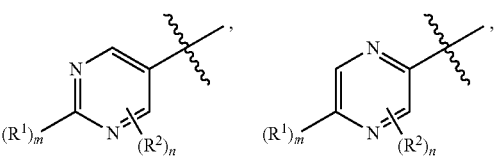
In certain embodiments, preferably Cy is selected from the group consisting of:
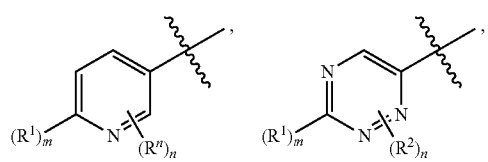
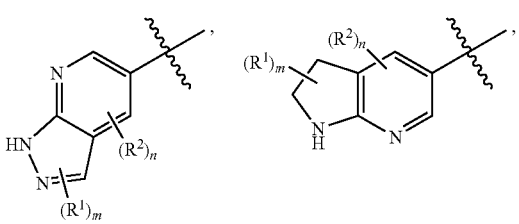
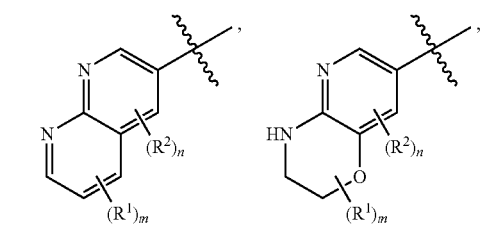
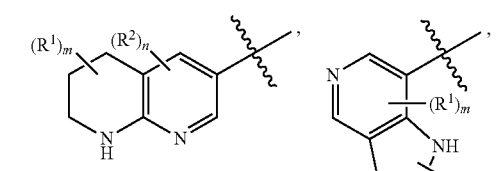
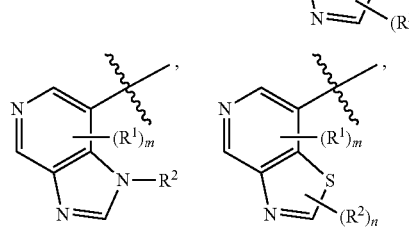
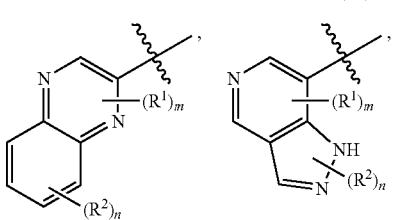

-continued
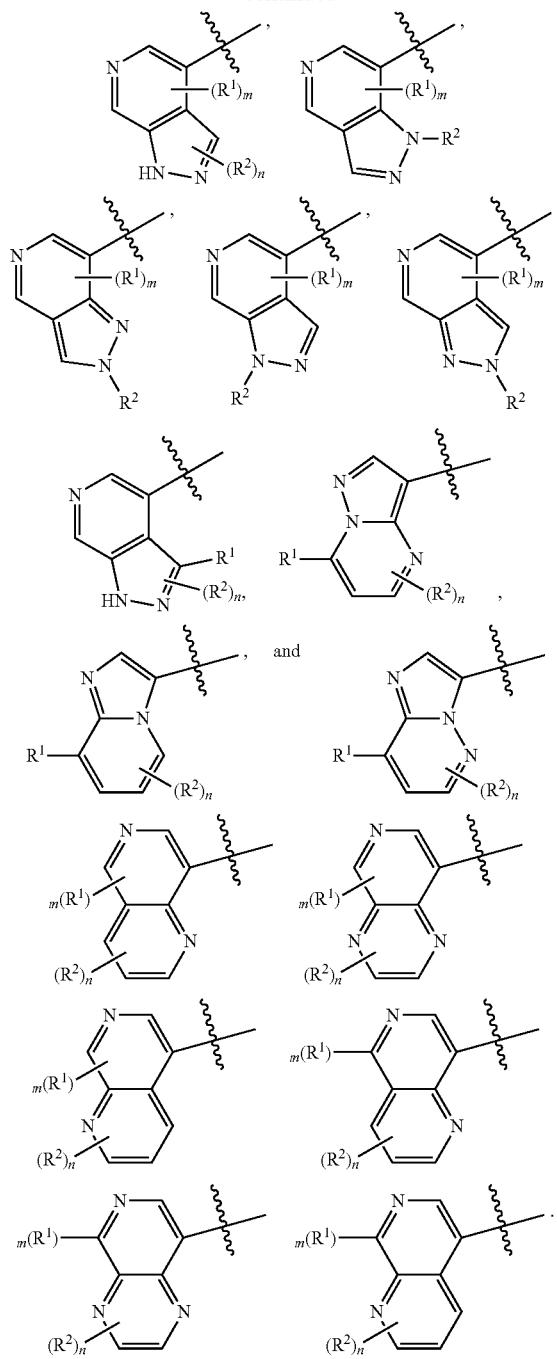
More preferably, Cy is selected from the group consisting of:
-continued
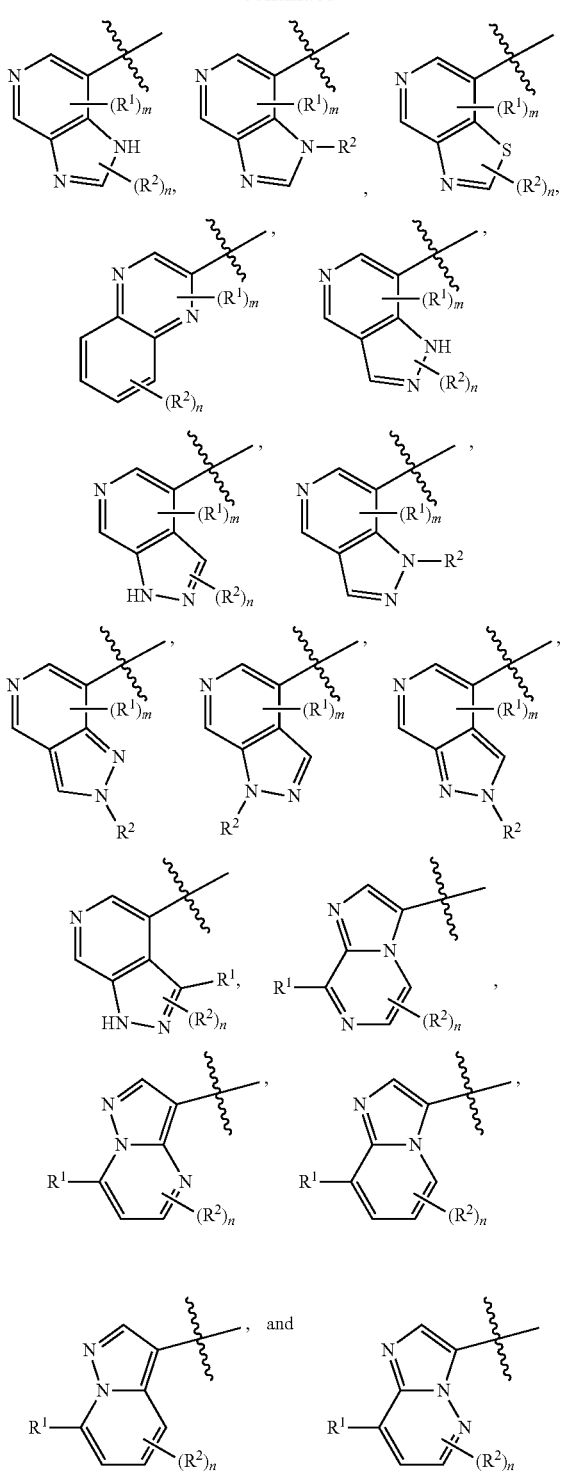
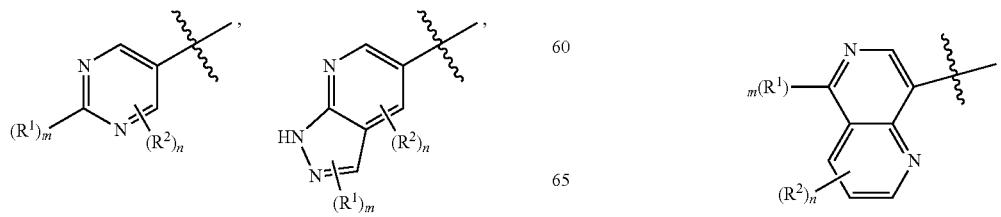

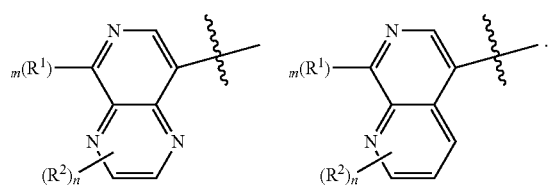
In certain embodiments, Cy is selected from the group consisting of:
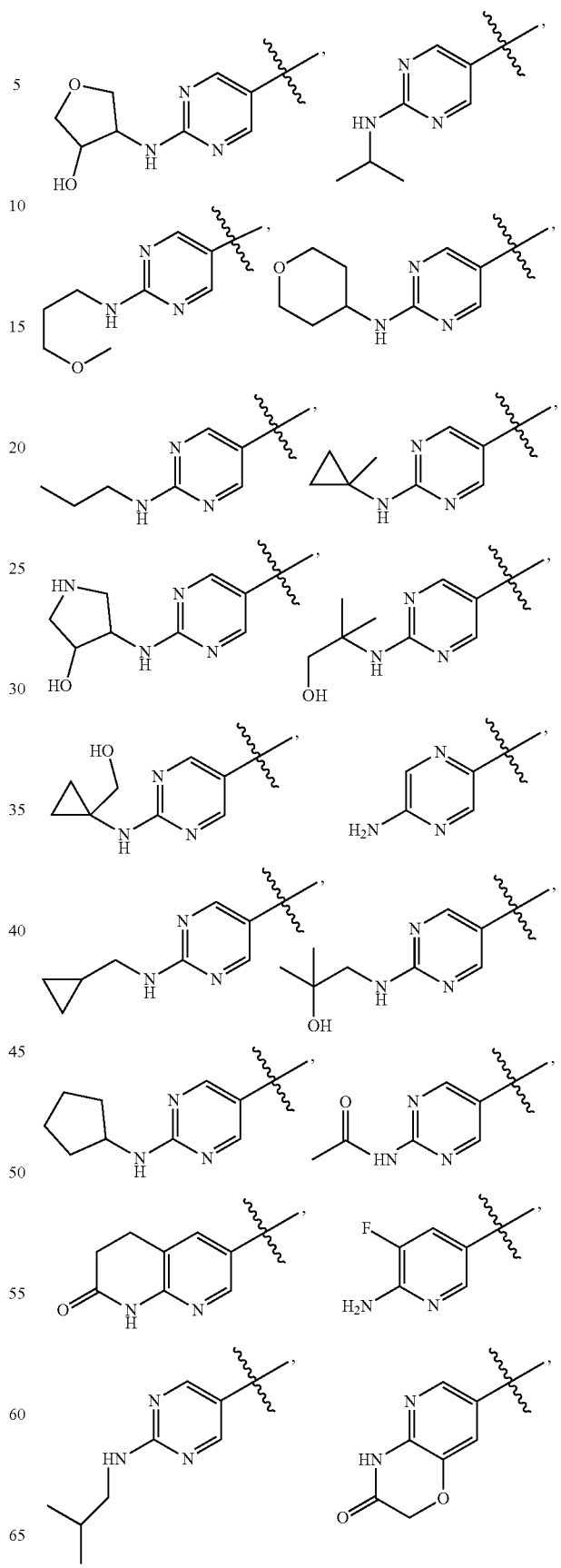

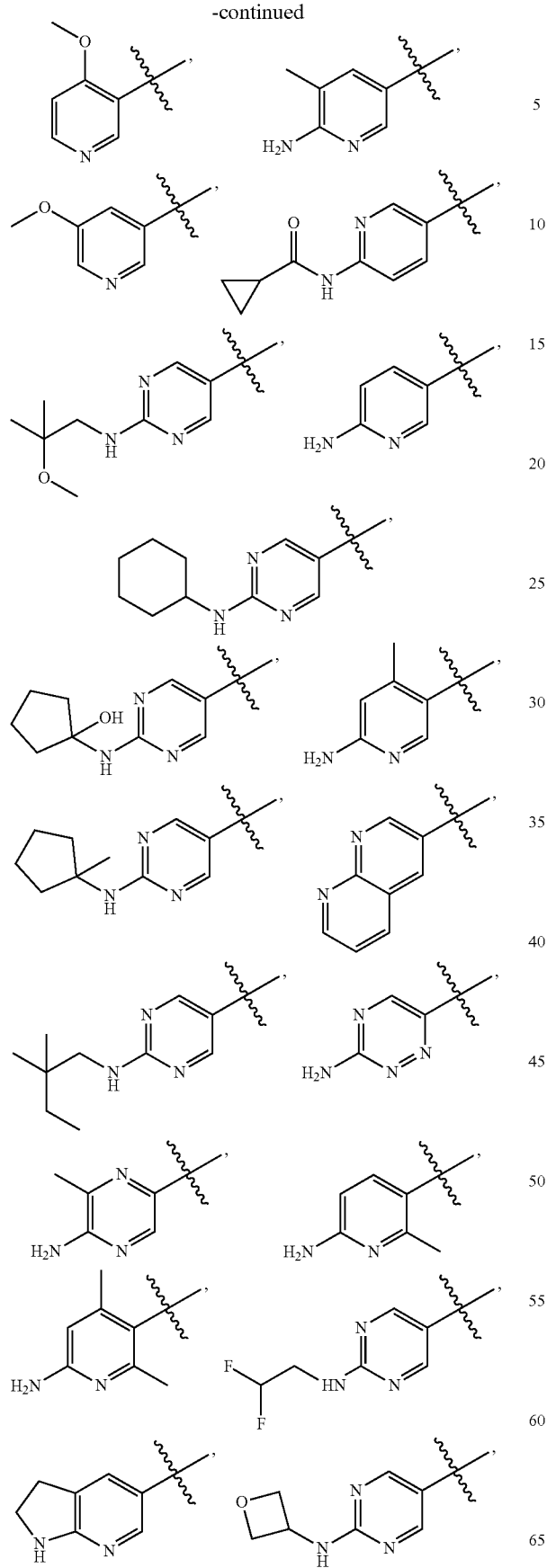
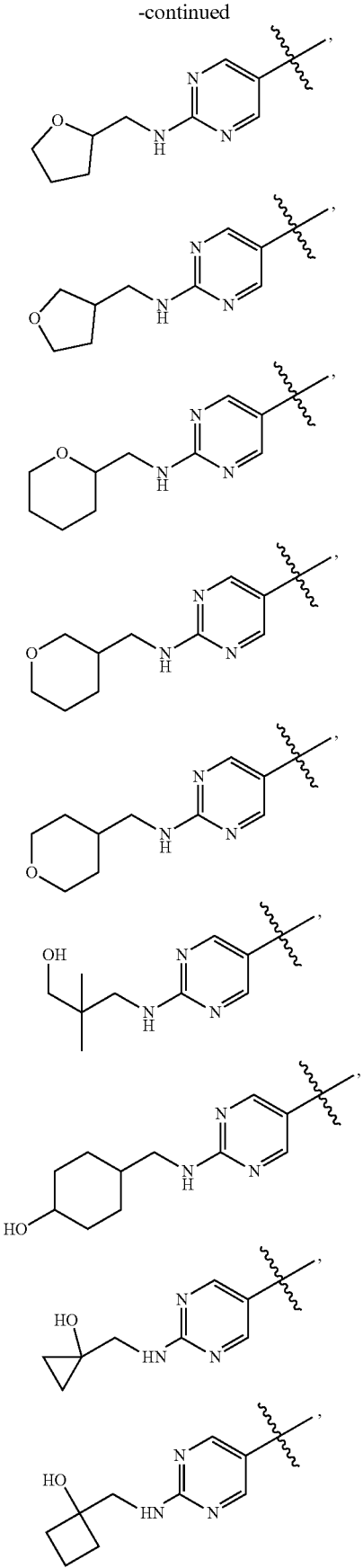

19
-continued
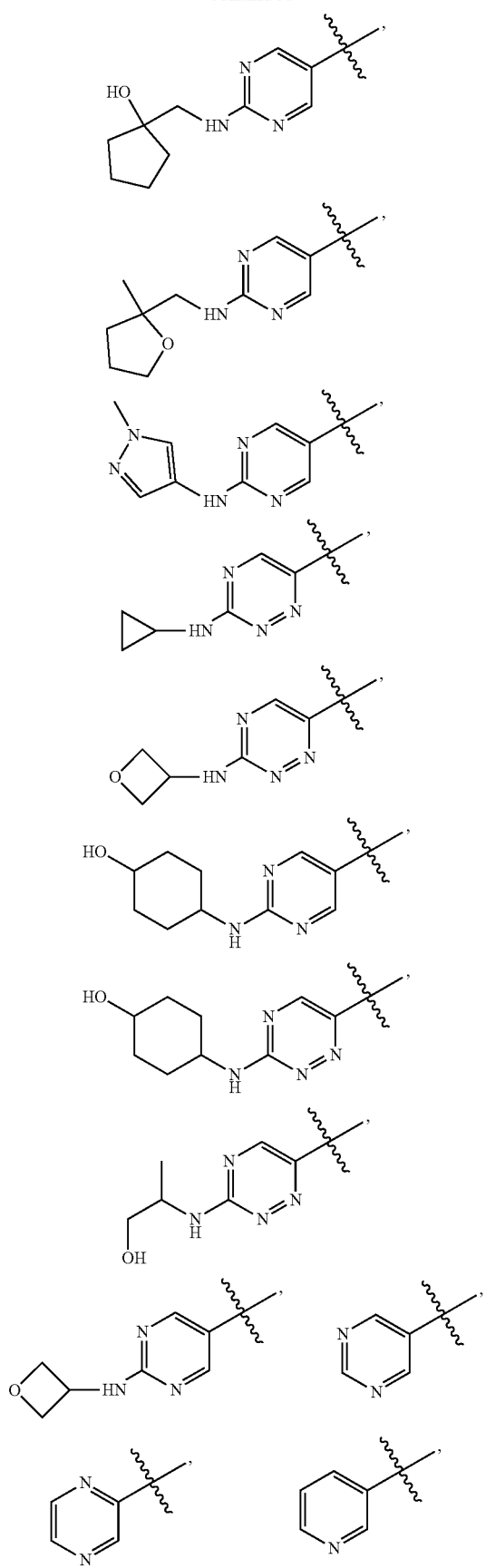
20
-continued
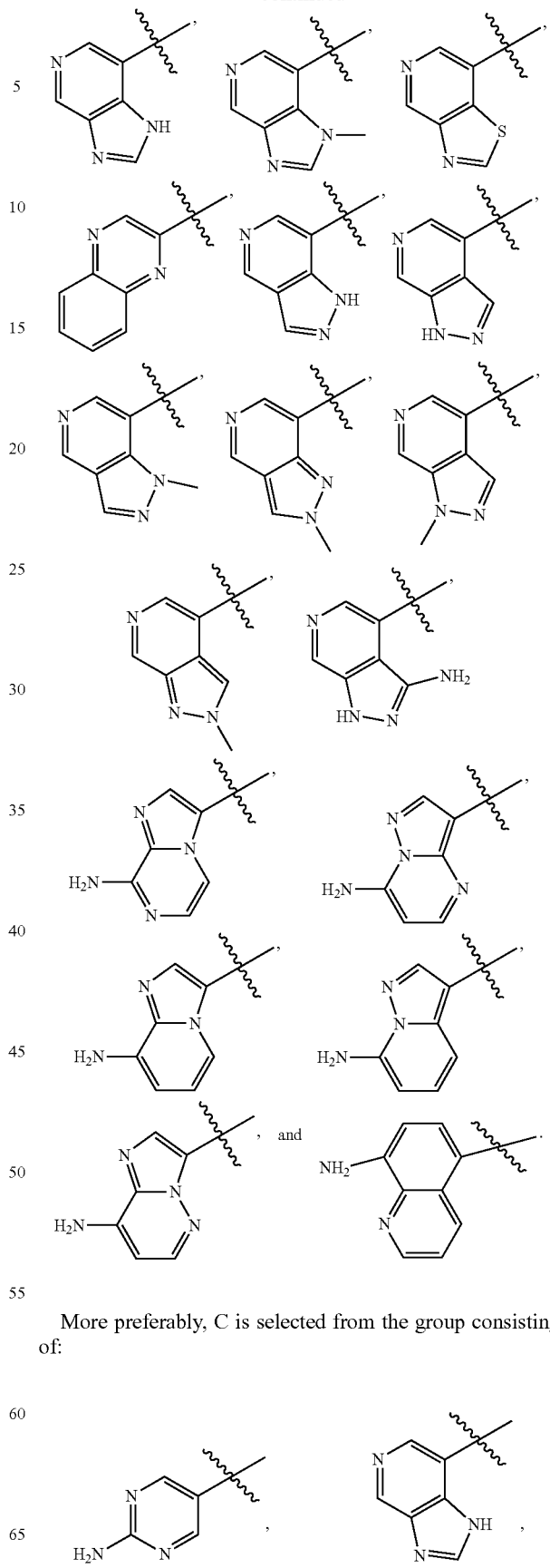
More preferably, C is selected from the group consisting of:

-continued

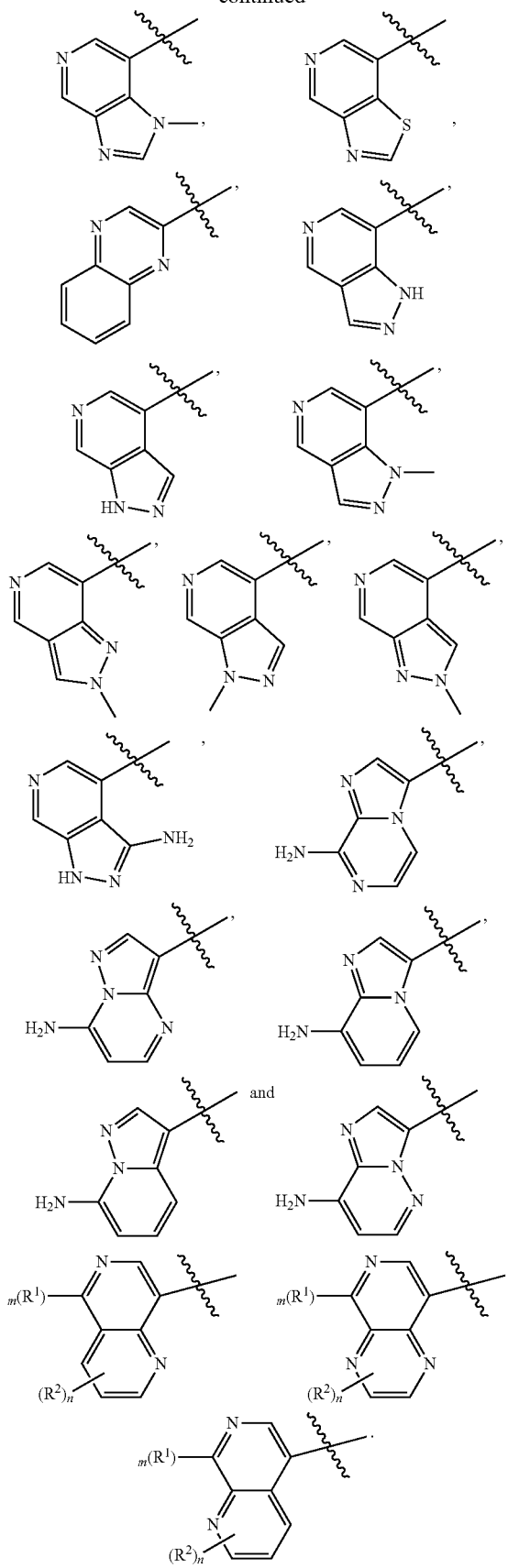

For the avoidance of doubt where rings systems, comprising two or more rings fused together, are drawn and an $R^1$ and/or an $R^2$ groups is drawn such the $R^1$ and/or $R^2$ group position is not fixed on the ring, the $R^1$ and/or $R^2$ groups can be bound at any chemically feasible point on any of the rings.

In the compounds of the invention, m is 0 or 1; and n is 0, 1 or 2. In one embodiment, m is 0 or 1; and n is 0 or 1.

In certain preferred embodiments, m is 1; and n is 0, 1 or 2 (more preferably n is 0 or 1). In one preferred embodiment, m is 1; and n is 1. In another preferred embodiment, m is 1; and n is 0.

In certain embodiments, m is 0; and n is 0, 1 or 2 (more preferably n is 0 or 1). In one embodiment, m is 0; and n is 1. In another embodiment, m is 0; and n is 0. In another embodiment, m is 0; and n is 2.

In embodiments of the invention, when present, $R^1$ is selected from the group consisting of —$NH_2$; —$NR^A(C_{1-6}alkyl)$ (for example —$NR^A(C_{1-3}alkyl)$); —$NR^A$ ($C_{1-3}$alkyl substituted by 1, 2 or 3 groups independently selected from the group consisting of OH, halogen, and O—$C_{1-3}$alkyl optionally substituted by 1, 2 or 3 halogen) (for example —$NR^A(C_{1-3}$alkyl substituted by 1, 2 or 3 groups independently selected from the group consisting of OH, halogen, and O—$C_{1-3}$alkyl optionally substituted by 1, 2 or 3 halogen)); —$NR^A(C(O)C_{1-6}$alkyl optionally substituted by 1, 2 or 3 groups independently selected from the group consisting of OH, halogen and O—$C_{1-3}$-alkyl optionally substituted by 1, 2 or 3 halogen) (for example, —$NR^A$ (C(O)$C_{1-3}$alkyl optionally substituted by 1, 2 or 3 groups independently selected from the group consisting of OH, halogen and O—$C_{1-3}$ alkyl optionally substituted by 1, 2 or 3 halogen)); —$NR^A(C_{0-3}$alkyene-$C_{3-6}$cycloalkyl, wherein said cycloalkyl is optionally substituted by 1, 2 or 3 groups independently selected from the group consisting of OH, halogen, $C_{1-3}$alkyl optionally substituted by 1, 2 or 3 halogen, $C_{1-3}$alkyl-OH, and O—$C_{1-3}$ alkyl optionally substituted by 1, 2 or 3 halogen); —$NR^A(C_{0-3}$alkyene-$C_{3-6}$heterocycloalkyl, wherein said heterocycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen); —$NR^A$ (C(O)$C_{3-6}$cycloalkyl optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen); and —$NR^A$ (5- or 6-membered heteroaryl group comprising at least 1 N heteroatom and optionally 1 or 2 further heteroatoms selected from the group consisting of N, S and O (preferably N and S, more preferably N), wherein said 5- or 6-membered heteroaryl group is optionally substituted with 1 or 2 substituents independently selected from the group consisting of $C_{1-3}$alkyl optionally substituted by 1, 2 or 3 groups independently selected from the group consisting of halogen, OH and O—$C_{1-3}$alkyl optionally substituted by 1, 2 or 3 halogen; halogen; —O—$C_{1-3}$alkyl optionally substituted by 1, 2 or 3 groups independently selected from the group consisting of halogen, OH and O—$C_{1-3}$alkyl optionally substituted by 1, 2 or 3 halogen; OH; $NH_2$; $NH(C_{1-6}alkyl)$; $N(C_{1-6}alkyl)_2$; cyano; $C_{3-4}$cycloalkyl optionally substituted by 1, 2, or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen).

In one preferred embodiment, $R^A$ is hydrogen, and as such, when present, $R^1$ is selected from the group consisting of —$NH_2$; —$NH(C_{1-6}alkyl)$ (for example —$NH(C_{1-3}alkyl)$); —$NH(C_{1-6}alkyl$ substituted by 1, 2 or 3 groups independently selected from the group consisting of OH, halogen, and O—$C_{1-6}alkyl$ optionally substituted by 1, 2 or 3 halogen) (for example $NH(C_{1-3}$ alkyl substituted by 1, 2 or 3 groups independently selected from the group consisting of OH, halogen, and O—$C_{1-3}alkyl$ optionally substituted by 1, 2 or 3 halogen)); —$NH(C(O)C_{1-6}alkyl$ optionally substituted by 1, 2 or 3 groups independently selected from the group consisting of OH, halogen and O—$C_{1-3}$ alkyl optionally substituted by 1, 2 or 3 halogen) (for example —NH $(C(O)C_{1-3}alkyl$ optionally substituted by 1, 2 or 3 groups independently selected from the group consisting of OH, halogen and O—$C_{1-3}alkyl$ optionally substituted by 1, 2 or 3 halogen)); —$NH(C_{0-3}alkyene-C_{3-6}cycloalkyl$, wherein said cycloalkyl is optionally substituted by 1, 2 or 3 groups independently selected from the group consisting of OH, halogen, $C_{1-3}alkyl$ optionally substituted by 1, 2 or 3 halogen, $C_{1-3}alkyl$-OH, and O—$C_{1-3}alkyl$ optionally substituted by 1, 2 or 3 halogen); —$NH(C_{0-3}alkyene-C_{3-6}heterocycloalkyl$, wherein said heterocycloalkyl is optionally substituted by 1, 2 or 3 groups independently selected from the group consisting of OH, halogen, $C_{1-3}$ alkyl optionally substituted by 1, 2 or 3 halogen, $C_{1-3}alkyl$-OH, and O—$C_{1-3}$ alkyl optionally substituted by 1, 2 or 3 halogen); —$NH(C(O)C_{3-6}cycloalkyl$ optionally substituted by 1, 2 or 3 groups independently selected from the group consisting of OH, halogen, $C_{1-3}$ alkyl optionally substituted by 1, 2 or 3 halogen, $C_{1-3}alkyl$-OH, and O—$C_{1-3}alkyl$ optionally substituted by 1, 2 or 3 halogen); and —NH (5- or 6-membered heteroaryl group comprising at least 1 N heteroatom and optionally 1 or 2 further heteroatoms selected from the group consisting of N, S and O (preferably N and S, more preferably N), wherein said 5- or 6-membered heteroaryl group is optionally substituted with 1 or 2 substituents independently selected from the group consisting of $C_{1-3}alkyl$ optionally substituted by 1, 2 or 3 groups independently selected from the group consisting of halogen, OH and O—$C_{1-3}alkyl$ optionally substituted by 1, 2 or 3 halogen; halogen; —O—$C_{1-3}alkyl$ optionally substituted by 1, 2 or 3 groups independently selected from the group consisting of halogen, OH and O—$C_{1-3}alkyl$ optionally substituted by 1, 2 or 3 halogen; OH; $NH_2$; $NH(C_{1-6}alkyl)$; $N(C_{1-6}alkyl)_2$; cyano; $C_{3-4}cycloalkyl$ optionally substituted by 1, 2 or 3 groups independently selected from the group consisting of OH, halogen, $C_{1-3}alkyl$ optionally substituted by 1, 2 or 3 halogen, $C_{1-3}alkyl$-OH, and O—$C_{1-3}alkyl$ optionally substituted by 1, 2 or 3 halogen)

In one embodiment of the invention, when present, $R^1$ is selected from the group consisting of —$NH_2$; —$NR^A(C_{1-6}alkyl)$; —$NR^A(C_{1-6}alkyl$ substituted by 1, 2 or 3 groups independently selected from the group consisting of OH, halogen, and O—$C_{1-3}alkyl$ optionally substituted by 1, 2 or 3 halogen); —$NR^A$ $(C(O)C_{1-6}alkyl$ optionally substituted by 1, 2 or 3 groups independently selected from the group consisting of OH, halogen and O—$C_{1-3}$ alkyl optionally substituted by 1, 2 or 3 halogen); —$NR^A(C_{0-3}alkyene$-$C_{3-6}cycloalkyl$, wherein said cycloalkyl is optionally substituted by 1, 2 or 3 groups independently selected from the group consisting of OH, halogen, $C_{1-3}alkyl$ optionally substituted by 1, 2 or 3 halogen, $C_{1-3}alkyl$-OH, and O—$C_{1-3}$ alkyl optionally substituted by 1, 2 or 3 halogen); —$NR^A$ ($C_{0-3}alkyene$-$C_{3-6}heterocycloalkyl$, wherein said heterocycloalkyl is optionally substituted by 1, 2 or 3 groups independently selected from the group consisting of OH, halogen, $C_{1-3}alkyl$ optionally substituted by 1, 2 or 3 halogen, $C_{1-3}alkyl$-OH, and O—$C_{1-3}$ alkyl optionally substituted by 1, 2 or 3 halogen); and —$NR^A(C(O)C_{3-6}cycloalkyl$ optionally substituted by 1, 2 or 3 groups independently selected from the group consisting of OH, halogen, $C_{1-3}alkyl$ optionally substituted by 1, 2 or 3 halogen, $C_{1-3}alkyl$-OH, and O—$C_{1-3}$ alkyl optionally substituted by 1, 2 or 3 halogen).

In one embodiment of the invention, when present, $R^1$ is selected from the group consisting of —$NH_2$; —$NR^A(C_{1-6}alkyl)$; —$NR^A(C_{1-6}alkyl$ substituted by 1, 2 or 3 groups independently selected from the group consisting of OH, halogen, and O—$C_{1-3}alkyl$ optionally substituted by 1, 2 or 3 halogen); —$NR^A(C_{0-3}alkyene$-$C_{3-6}cycloalkyl$, wherein said cycloalkyl is optionally substituted by 1, 2 or 3 groups independently selected from the group consisting of OH, halogen, $C_{1-3}alkyl$ optionally substituted by 1, 2 or 3 halogen, $C_{1-3}alkyl$-OH, and O—$C_{1-3}alkyl$ optionally substituted by 1, 2 or 3 halogen); and —$NR^A(C_{0-3}alkyene$-$C_{3-6}heterocycloalkyl$, wherein said heterocycloalkyl is optionally substituted by 1, 2 or 3 groups independently selected from the group consisting of OH, halogen, $C_{1-3}$ alkyl optionally substituted by 1, 2 or 3 halogen, $C_{1-3}alkyl$-OH, and O—$C_{1-3}$ alkyl optionally substituted by 1, 2 or 3 halogen).

In another embodiment of the invention, when present, $R^1$ is selected from the group consisting of —$NH_2$; —$NR^A(C_{1-6}alkyl)$ (for example —$NR^A(C_{1-3}alkyl)$); and —$NR^A(C_{1-6}alkyl$ substituted by 1, 2 or 3 groups independently selected from the group consisting of OH, halogen, and O—$C_{1-3}alkyl$ optionally substituted by 1, 2 or 3 halogen) (for example —$NR^A(C_{1-3}alkyl$ substituted by 1, 2 or 3 groups independently selected from the group consisting of OH, halogen, and O—$C_{1-3}alkyl$ optionally substituted by 1, 2 or 3 halogen)).

In one preferred embodiment of the invention, when present, $R^1$ is —$NH_2$.

In embodiments wherein $R^1$ may be —$NR^A(C_{1-6}alkyl)$; —$NR^A(C_{1-6}alkyl$ substituted by 1, 2 or 3 groups independently selected from the group consisting of OH, halogen, and O—$C_{1-3}alkyl$ optionally substituted by 1, 2 or 3 halogen); or —$NR^A(C(O)C_{1-6}alkyl$ optionally substituted by 1, 2 or 3 groups independently selected from the group consisting of OH, halogen and O—$C_{1-3}alkyl$ optionally substituted by 1, 2 or 3 halogen); the $C_{1-6}alkyl$ group may preferably be selected from the group consisting of methyl, ethyl, n-propyl, i-propyl, n-butyl, i-butyl, sec-butyl, t-butyl, pentyl, and hexyl.

In certain embodiments wherein $R^1$ may be —$NR^A(C_{1-6}alkyl)$; —$NR^A(C_{1-6}alkyl$ substituted by 1, 2 or 3 groups independently selected from the group consisting of OH, halogen, and O—$C_{1-3}alkyl$ optionally substituted by 1, 2 or 3 halogen); or —$NR^A(C(O)C_{1-6}alkyl$ optionally substituted by 1, 2 or 3 groups independently selected from the group consisting of OH, halogen and O—$C_{1-3}alkyl$ optionally substituted by 1, 2 or 3 halogen); the $C_{1-6}alkyl$ may be a $C_{1-4}alkyl$ group (for example a methyl, ethyl, n-propyl, i-propyl, n-butyl, i-butyl, sec-butyl, or t-butyl group), or a $C_{1-3}alkyl$ group (for example methyl, ethyl, n-propyl, or i-propyl group).

In embodiments wherein $R^1$ may be —$NR^A(C_{0-3}alkyene$-$C_{3-6}cycloalkyl$, wherein said cycloalkyl is optionally substituted by 1, 2 or 3 groups independently selected from the group consisting of OH, halogen, $C_{1-3}alkyl$ optionally substituted by 1, 2 or 3 halogen, $C_{1-3}alkyl$-OH, and O—$C_{1-3}alkyl$ optionally substituted by 1, 2 or 3 halogen); or —$NR^A(C(O)C_{3-6}cycloalkyl$ optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen), preferably the $C_{3-6}$cycloalkyl groups is a monocyclic $C_{3-6}$cycloalkyl, for example a $C_{3-6}$cycloalkyl group selected from the group consisting of cyclopropyl, cyclobutyl, cyclopentyl, and cyclohexyl.

In embodiments wherein $R^1$ may be —NR$^A$($C_{0-3}$alkyene-$C_{3-6}$heterocycloalkyl, wherein said heterocycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen), preferably the $C_{3-6}$heterocycloalkyl groups is a monocyclic $C_{3-6}$heterocycloalkyl, for example a $C_{3-6}$heterocycloalkyl group selected from the group consisting of aziridine, oxirane, pyrrolidine, imidazolidine, pyrazoladine, piperidine, dioxane, morpholine, dithiane, oxathiane, and thiomorpholine.

In embodiments wherein $R^1$ may be NR$^A$(5- or 6-membered heteroaryl group comprising at least 1 N heteroatom and optionally 1 or 2 further heteroatoms selected from the group consisting of N, S and O, wherein said 5- or 6-membered heteroaryl group is optionally substituted with 1 or 2 substituents independently selected from the group consisting of $C_{1-3}$alkyl optionally substituted by 1, 2 or 3 groups independently selected from the group consisting of halogen, OH and O—$C_{1-3}$alkyl optionally substituted by 1, 2 or 3 halogen; halogen; —O—$C_{1-3}$alkyl optionally substituted by 1, 2 or 3 groups independently selected from the group consisting of halogen, OH and O—$C_{1-3}$alkyl optionally substituted by 1, 2 or 3 halogen; OH; NH$_2$; NH($C_{1-6}$alkyl); N($C_{1-6}$alkyl)$_2$; cyano; $C_{3-6}$cycloalkyl optionally substituted by 1, 2, or 3 groups independently selected from the group consisting of OH, halogen, $C_{1-3}$alkyl optionally substituted by 1, 2 or 3 halogen, $C_{1-3}$alkyl-OH, and O—$C_{1-3}$alkyl optionally substituted by 1, 2 or 3 halogen), preferably the 5- or 6-membered heteroaryl group comprises at least 1 N heteroatom and optionally 1 or 2 further heteroatoms selected from the group consisting of N and S, and more preferably N. In another preferred embodiment, the 5- or 6-membered heteroaryl group is selected from the group consisting of pyridyl (i.e., pyridinyl), pyrimidinyl, pyrazinyl, pyridazinyl, triazinyl, imidazolyl, thiazolyl, indolyl, pyrryl, oxazolyl, isoxazolyl, pyrazolyl, triazolyl, 1,2,4-thiadiazolyl, and isothiazolyl.

In the compounds of the invention, when present, R$^A$ is selected from the group consisting of hydrogen; —$C_{1-6}$alkyl optionally substituted by 1, 2 or 3 groups independently selected from the group consisting of OH, halogen and O—$C_{1-3}$alkyl optionally substituted by 1, 2 or 3 halogen (for example, —$C_{1-3}$alkyl optionally substituted by 1, 2 or 3 groups independently selected from the group consisting of OH, halogen and O—$C_{1-3}$alkyl optionally substituted by 1, 2 or 3 halogen); —$C_{0-3}$alkyene-$C_{3-6}$cycloalkyl, wherein said cycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen; —$C_{0-3}$ alkyene-$C_{3-6}$heterocycloalkyl, wherein said heterocycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen; —C(O)$C_{3-6}$cycloalkyl optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen; —C(O)$C_{1-6}$alkyl optionally substituted by 1, 2 or 3 groups independently selected from the group consisting of OH, halogen and O—$C_{1-3}$ alkyl optionally substituted by 1, 2 or 3 halogen (for example, —C(O)$C_{1-3}$alkyl optionally substituted by 1, 2 or 3 groups independently selected from the group consisting of OH, halogen and O—$C_{1-3}$alkyl optionally substituted by 1, 2 or 3 halogen); —C(O)$C_{3-6}$cycloalkyl optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen; and 5- or 6-membered heteroaryl group comprising at least 1 N heteroatom and optionally 1 or 2 further heteroatoms selected from the group consisting of N, S and O, wherein said 5- or 6-membered heteroaryl group is optionally substituted with 1 or 2 substituents independently selected from the group consisting of $C_{1-3}$alkyl optionally substituted by 1, 2 or 3 groups independently selected from the group consisting of halogen, OH and O—$C_{1-3}$alkyl optionally substituted by 1, 2 or 3 halogen; halogen; —O—$C_{1-3}$alkyl optionally substituted by 1, 2 or 3 groups independently selected from the group consisting of halogen, OH and O—$C_{1-3}$alkyl optionally substituted by 1, 2 or 3 halogen; OH; NH$_2$; NH($C_{1-6}$alkyl); N($C_{1-3}$alkyl)$_2$; cyano; $C_{3-4}$cycloalkyl optionally substituted by 1, 2, or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen.

In one embodiment, when present, R$^A$ is selected from the group consisting of hydrogen; —$C_{1-6}$alkyl optionally substituted by 1, 2 or 3 groups independently selected from the group consisting of OH, halogen and O—$C_{1-3}$alkyl optionally substituted by 1, 2 or 3 halogen; —$C_{0-3}$alkyene-$C_{3-6}$cycloalkyl, wherein said cycloalkyl is optionally substituted by 1, 2 or 3 groups independently selected from the group consisting of OH, halogen, $C_{1-3}$alkyl optionally substituted by 1, 2 or 3 halogen, $C_{1-3}$alkyl-OH, and O—$C_{1-3}$alkyl optionally substituted by 1, 2 or 3 halogen; —$C_{0-3}$alkyene-$C_{3-6}$heterocycloalkyl, wherein said heterocycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen; —C(O)$C_{3-6}$cycloalkyl optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen; and —C(O)$C_6$cycloalkyl optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen.

In one embodiment, when present, R$^A$ is selected from the group consisting of hydrogen; —$C_{1-6}$alkyl optionally substituted by 1, 2 or 3 groups independently selected from the group consisting of OH, halogen and O—$C_{1-3}$alkyl optionally substituted by 1, 2 or 3 halogen; —$C_{0-3}$alkyene-$C_{3-6}$cycloalkyl, wherein said cycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen; and —$C_{0-3}$ alkyene-$C_{3-6}$heterocycloalkyl, wherein said heterocycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$ alkyl optionally substituted by 1, 2 or 3 halogen.

In one embodiment, when present, $R^4$ is selected from the group consisting of hydrogen; and —$C_{1-6}$alkyl optionally substituted by 1, 2 or 3 groups independently selected from the group consisting of OH, halogen and O—$C_{1-3}$alkyl optionally substituted by 1, 2 or 3 halogen (for example —$C_{1-3}$alkyl optionally substituted by 1, 2 or 3 groups independently selected from the group consisting of OH, halogen and O—$C_{1-3}$alkyl optionally substituted by 1, 2 or 3 halogen).

In one preferred embodiment, when present, $R^4$ is hydrogen.

In embodiments wherein $R^4$ may be —$C_{1-6}$alkyl optionally substituted by 1, 2 or 3 groups independently selected from the group consisting of OH, halogen and O—$C_{1-3}$alkyl optionally substituted by 1, 2 or 3 halogen; or —C(O)$C_{1-6}$alkyl optionally substituted by 1, 2 or 3 groups independently selected from the group consisting of OH, halogen and O—$C_{1-3}$alkyl optionally substituted by 1, 2 or 3 halogen; the $C_{1-6}$alkyl group may preferably be selected from the group consisting of methyl, ethyl, n-propyl, i-propyl, n-butyl, i-butyl, sec-butyl, t-butyl, pentyl, and hexyl.

In certain embodiments wherein $R^4$ may be —$C_{1-6}$alkyl optionally substituted by 1, 2 or 3 groups independently selected from the group consisting of OH, halogen and O—$C_{1-3}$alkyl optionally substituted by 1, 2 or 3 halogen; or —C(O)$C_{1-6}$alkyl optionally substituted by 1, 2 or 3 groups independently selected from the group consisting of OH, halogen and O—$C_{1-3}$alkyl optionally substituted by 1, 2 or 3 halogen; the $C_{1-6}$alkyl is a $C_{1-4}$alkyl group (for example a methyl, ethyl, n-propyl, i-propyl, n-butyl, i-butyl, sec-butyl, or t-butyl group), or a $C_{1-3}$alkyl group (for example methyl, ethyl, n-propyl, or i-propyl group).

In embodiments wherein $R^4$ may be —$C_{0-3}$alkyene-$C_{3-6}$cycloalkyl, wherein said cycloalkyl is optionally substituted by 1, 2 or 3 groups independently selected from the group consisting of OH, halogen, $C_{1-3}$ alkyl optionally substituted by 1, 2 or 3 halogen, $C_{1-3}$alkyl-OH, and O—$C_{1-3}$alkyl optionally substituted by 1, 2 or 3 halogen); or —C(O)$C_{3-6}$cycloalkyl optionally substituted by 1, 2 or 3 groups independently selected from the group consisting of OH, halogen, $C_{1-3}$alkyl optionally substituted by 1, 2 or 3 halogen, $C_{1-3}$alkyl-OH, and O—$C_{1-3}$ alkyl optionally substituted by 1, 2 or 3 halogen, preferably the $C_{3-6}$cycloalkyl groups is a monocyclic $C_{3-6}$cycloalkyl, for example a $C_{3-6}$cycloalkyl group selected from the group consisting of cyclopropyl, cyclobutyl, cyclopentyl, and cyclohexyl.

In embodiments wherein $R^4$ may be —$C_{0-3}$alkyene-$C_{3-6}$heterocycloalkyl, wherein said heterocycloalkyl is optionally substituted by 1, 2 or 3 groups independently selected from the group consisting of OH, halogen, $C_{1-3}$alkyl optionally substituted by 1, 2 or 3 halogen, $C_{1-3}$alkyl-OH, and O—$C_{1-3}$ alkyl optionally substituted by 1, 2 or 3 halogen, preferably the $C_{3-6}$heterocycloalkyl groups is a monocyclic $C_{3-6}$heterocycloalkyl, for example a $C_{3-6}$heterocycloalkyl group selected from the group consisting of aziridine, oxirane, pyrrolidine, imidazolidine, pyrazoladine, piperidine, dioxane, morpholine, dithiane, oxathiane, and thiomorpholine.

In embodiments wherein $R^4$ may be a 5- or 6-membered heteroaryl group comprising at least 1 N heteroatom and optionally 1 or 2 further heteroatoms selected from the group consisting of N, S and O, wherein said 5- or 6-membered heteroaryl group is optionally substituted with 1 or 2 substituents independently selected from the group consisting of $C_{1-3}$alkyl optionally substituted by 1, 2 or 3 groups independently selected from the group consisting of halogen, OH and O—$C_{1-3}$alkyl optionally substituted by 1, 2 or 3 halogen; halogen; —O—$C_{1-3}$alkyl optionally substituted by 1, 2 or 3 groups independently selected from the group consisting of halogen, OH and O—$C_{1-3}$alkyl optionally substituted by 1, 2 or 3 halogen; OH; $NH_2$; $NH(C_{1-6}alkyl)$; $N(C_{1-6}alkyl)_2$; cyano; $C_{3-4}$cycloalkyl optionally substituted by 1, 2, or 3 groups independently selected from the group consisting of OH, halogen, $C_{1-3}$alkyl optionally substituted by 1, 2 or 3 halogen, $C_{1-3}$alkyl-OH, and O—$C_{1-3}$alkyl optionally substituted by 1, 2 or 3 halogen, preferably the 5- or 6-membered heteroaryl group comprises at least 1 N heteroatom and optionally 1 or 2 further heteroatoms selected from the group consisting of N and S, and more preferably N. In another preferred embodiment, the 5- or 6-membered heteroaryl group is selected from the group consisting of pyridyl (i.e., pyridinyl), pyrimidinyl, pyrazinyl, pyridazinyl, triazinyl, imidazolyl, thiazolyl, indolyl, pyrryl, oxazolyl, isoxazolyl, pyrazolyl, triazolyl, 1,2,4-thiadiazolyl, and isothiazolyl.

In the compounds of the invention, when present, each $R^2$ is independently selected from the group consisting of $C_{1-6}$alkyl optionally substituted by 1, 2 or 3 groups independently selected from the group consisting of halogen, OH and O—$C_{1-3}$alkyl optionally substituted by 1, 2 or 3 halogen (for example $C_{1-3}$alkyl optionally substituted by 1, 2 or 3 groups independently selected from the group consisting of halogen, OH and O—$C_{1-3}$alkyl optionally substituted by 1, 2 or 3 halogen); halogen; —O—$C_{1-6}$alkyl optionally substituted by 1, 2 or 3 groups independently selected from the group consisting of halogen, OH and O—$C_{1-3}$alkyl optionally substituted by 1, 2 or 3 halogen (for example—O—$C_{1-3}$alkyl optionally substituted by 1, 2 or 3 groups independently selected from the group consisting of halogen, OH and O—$C_{1-3}$alkyl optionally substituted by 1, 2 or 3 halogen); OH; =O; $NH_2$; $NH(C_{1-6}alkyl)$ (for example NH $C_{1-3}alkyl$); $N(C_{1-6}alkyl)_2$ (for example $NC_{1-3}alkyl)_2$; cyano; and $C_{3-6}$cycloalkyl optionally substituted by 1, 2, or 3 groups independently selected from the group consisting of halogen, OH and O—$C_{1-3}$alkyl optionally substituted by 1, 2 or 3 halogen.

In one embodiment, when present, each $R^2$ is independently selected from the group consisting of oxo, $C_{1-6}$alkyl optionally substituted by 1, 2 or 3 groups independently selected from the group consisting of halogen, OH and O—$C_{1-3}$alkyl optionally substituted by 1, 2 or 3 halogen; halogen; —O—$C_{1-6}$alkyl optionally substituted by 1, 2 or 3 groups independently selected from the group consisting of halogen, OH and O—$C_{1-3}$alkyl optionally substituted by 1, 2 or 3 halogen; OH; and $C_{3-6}$cycloalkyl optionally substituted by 1, 2, or 3 groups independently selected from the group consisting of halogen, OH and O—$C_{1-3}$alkyl optionally substituted by 1, 2 or 3 halogen.

In one embodiment, when present, each $R^2$ is independently selected from the group consisting of $C_{1-6}$alkyl optionally substituted by 1, 2 or 3 groups independently selected from the group consisting of halogen, OH and O—$C_{1-3}$alkyl optionally substituted by 1, 2 or 3 halogen; halogen; —O—$C_{1-6}$alkyl optionally substituted by 1, 2 or 3 groups independently selected from the group consisting of halogen, OH and O—$C_{1-3}$alkyl optionally substituted by 1, 2 or 3 halogen; and OH.

In one embodiment, when present, each $R^2$ is independently selected from the group consisting of $C_{1-3}$alkyl optionally substituted by 1, 2 or 3 groups independently selected from the group consisting of halogen, OH and O—$C_{1-3}$alkyl optionally substituted by 1, 2 or 3 halogen; halogen; —O—$C_{1-3}$alkyl optionally substituted by 1, 2 or 3 groups independently selected from the group consisting of halogen, OH and O—$C_{1-3}$alkyl optionally substituted by 1, 2 or 3 halogen; and OH.

In one embodiment, Cy is an optionally substituted nitrogen containing 6-membered aromatic ring having the following formula:

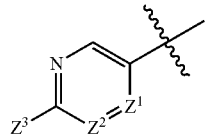

wherein $Z^1$ is a CH or N;
$Z^2$ is a CH or N;
$Z^3$ is a hydrogen or an optionally substituted amino group (for example, hydrogen, NH$_2$, or an amino group having 1 or 2 substituents selected from the group consisting or $C_{1-6}$alkyl group, a $C_{2-6}$alkenyl group, a $C_{3-10}$cycloalkyl group, a $C_{3-14}$aryl group, a $C_{7-26}$ aralkyl group, a $C_{1-6}$ alkyl-carbonyl group, a $C_{6-14}$aryl-carbonyl group, a $C_{1-6}$aralkyl-carbonyl group, a 5- to 14-membered aromatic heterocyclylcarbonyl group, a 3- to 14-membered non-aromatic heterocyclylcarbonyl group, a $C_{1-6}$alkoxy-carbonyl group, a 5- to 14-membered aromatic heterocyclic group, a carbamoyl group, a mono- or di-$C_{1-6}$alkyl-carbamoyl group, a mono- or di-$C_{7-16}$aralkyl-carbamoyl group, a $C_{1-6}$alkylsulfonyl group and a $C_{6-14}$ arylsulfonyl group, each of which optionally has 1 to 3 substituents selected from substituent group A:
(1) a halogen atom, (2) a nitro group, (3) a cyano group, (4) an oxo group, (5) a hydroxy group, (6) an optionally halogenated $C_{1-6}$ alkoxy group, (7) a $C_{6-14}$ aryloxy group (e.g., phenoxy, naphthoxy) (8) a $C_{7-16}$ aralkyloxy group (e.g., benzyloxy), (9) a 5- to 14-membered aromatic heterocyclyloxy group (e.g., pyridyloxy), (10) a 3- to 14-membered non-aromatic heterocyclyloxy group (e.g., morpholinyloxy, piperidinyloxy), (11) a $C_{1-6}$ alkyl-carbonyloxy group (e.g., acetoxy, propanoyloxy), (12) a $C_{6-14}$ aryl-carbonyloxy group (e.g., benzoyloxy, 1-naphthoyloxy, 2-naphthoyloxy), (13) a $C_{1-6}$alkoxy-carbonyloxy group (e.g., methoxycarbonyloxy, ethoxycarbonyloxy, propoxycarbonyloxy, butoxycarbonyloxy), (14) a mono- or di-$C_{1-6}$alkyl-carbamoyloxy group (e.g., methylcarbamoyloxy, ethylcarbamoyloxy, dimethylcarbamoyloxy, diethylcarbamoyloxy), (15) a $C_{6-14}$ aryl-carbamoyloxy group (e.g., phenylcarbamoyloxy, naphthylcarbamoyloxy), (16) a 5- to 14-membered aromatic heterocyclylcarbonyloxy group (e.g., nicotinoyloxy) (17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy), (19) a $C_{6-14}$ arylsulfonyloxy group optionally substituted by a $C_{1-6}$alkyl group (e.g., phenylsulfonyloxy, toluenesulfonyloxy), (20) an optionally halogenated $C_{1-6}$ alkylthio group, (21) a 5- to 14-membered aromatic heterocyclic group, (22) a 3- to 14-membered non-aromatic heterocyclic group, (23) a formyl group, (24) a carboxy group, (25) an optionally halogenated $C_{1-6}$alkyl-carbonyl group, (26) a $C_{6-14}$ aryl-carbonyl group, (27) a 5- to 14-membered aromatic heterocyclylcarbonyl group, (28) a 3- to 14-membered non-aromatic heterocyclylcarbonyl group, (29) a $C_{1-6}$ alkoxy-carbonyl group, (30) a $C_{6-14}$ aryloxy-carbonyl group (e.g., phenyloxycarbonyl, 1-naphthyloxycarbonyl, 2-naphthyloxycarbonyl), (31) a $C_{7-16}$ aralkyloxycarbonyl group (e.g., benzyloxycarbonyl, phenethyloxycarbonyl), (32) a carbamoyl group, (33) a thiocarbamoyl group, (34) a mono- or di-$C_{1-6}$ alkyl-carbamoyl group, (35) a $C_{6-14}$ aryl-carbamoyl group (e.g., phenylcarbamoyl), (36) a 5- to 14-membered aromatic heterocyclylcarbamoyl group (e.g., pyridylcarbamoyl, thienylcarbamoyl), (37) a 3- to 14-membered non-aromatic heterocyclylcarbamoyl group (e.g., morpholinylcarbamoyl, piperidinylcarbamoyl), (38) an optionally halogenated 01-6 alkylsulfonyl group, (39) a $C_{6-14}$ arylsulfonyl group, (40) a 5- to 14-membered aromatic heterocyclylsulfonyl group (e.g., pyridylsulfonyl, thienylsulfonyl), (41) an optionally halogenated $C_{1-6}$alkylsulfinyl group, (42) a $C_{6-14}$ arylsulfinyl group (e.g., phenylsulfinyl, 1-naphthylsulfinyl, 2-naphthylsulfinyl) (43) a 5- to 14-membered aromatic heterocyclylsulfinyl group (e.g., pyridylsulfinyl, thienylsulfinyl), (44) an amino group, (45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino), (46) a mono- or di-$C_{6-14}$ arylamino group (e.g., phenylamino), (47) a 5- to 14-membered aromatic heterocyclylamino group (e.g., pyridylamino), 30 (48) a $C_{7-16}$ aralkylamino group (e.g., benzylamino), (49) a formylamino group, (50) a $C_{1-6}$alkyl-carbonylamino group (e.g., acetylamino, propanoylamino, butanoylamino), (51) a ($C_{1-6}$alkyl)($C_{1-6}$alkyl-carbonyl) an amino group (e.g., N-acetyl-N-methylamino), (52) a $C_{6-14}$ aryl-carbonylamino group (e.g., phenylcarbonylamino, naphthylcarbonylamino), (53) a $C_{1-6}$alkoxy-carbonylamino group (e.g., methoxycarbonylamino, ethoxycarbonylamino, propoxycarbonylamino, butoxycarbonylamino, tert-butoxycarbonylamino), (54) a $C_{7-16}$ aralkyloxy-carbonylamino group (e.g., benzyloxycarbonylamino), (55) a $C_{1-6}$ alkylsulfonylamino group (e.g., methylsulfonylamino, ethylsulfonylamino), (56) a $C_{6-14}$ arylsulfonylamino group optionally substituted by a $C_{1-6}$alkyl group (e.g., phenylsulfonylamino, toluenesulfonylamino), (57) an optionally halogenated $C_{1-6}$alkyl group, (58) a $C_{2-6}$alkenyl group, (59) a $C_{2-4}$alkynyl group, (60) a $C_{3-10}$ cycloalkyl group, (61) a $C_{3-10}$cycloalkenyl group and (62) a $C_{6-14}$ aryl group;
or hydrogen or an R$^1$ group as described above),
or $Z^2$ and $Z^3$ are bonded to each other to form an optionally substituted ring (for example, a optionally substituted 4, 5, 6 or 7 ring, such as an optionally substituted 4, 5, 6 or 7 aryl, heteroaryl, non-aromatic carbocyclic, or non-aromatic heterocyclic ring; for example optionally substituted by 1, 2 or 3 groups independently selected from substituent group A; or optionally substituted by 1 R¹ group and/or 1 or 2 R² groups as described above).

In one embodiment, Cy is

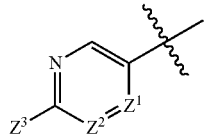

the combination of $Z^1$ and $Z^2$ ($Z^1$, $Z^2$) is (CH, N), (N, CH) or (N, N); and Cy is optionally further substituted by 1 to 3 substituents selected from (1) a $C_{1-6}$alkyl group and (2) an amino group (—$NH_2$); and $Z^3$ is an amino group (—$NH_2$) optionally substituted by 1-2 substituents selected from (1) a $C_{1-6}$alkyl group optionally substituted by 1, 2 or 3 substituents selected from OH and a 3- to 14-membered non-aromatic heterocyclic group, (2) a $C_{3-10}$cycloalkyl group optionally substituted by 1, 2 or 3 OH groups, (3) a 3- to 14-membered non-aromatic heterocyclic group and (4) a 5- to 14-membered aromatic heterocyclic group optionally substituted by 1 to 3 $C_{1-6}$alkyl groups; or $Z^2$ and $Z^3$ are bonded to each other to form a 5- to 14-membered aromatic heterocycle.

In such embodiments, Cy is

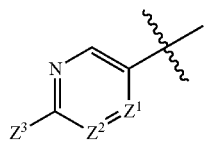

the combination of $Z^1$ and $Z^2$ ($Z^1$, $Z^2$) is (CH, N), (N, CH) or (N, N); and Cy is optionally further substituted by 1 to 3 $C_{1-6}$alkyl groups; and $Z^3$ is an amino group) —$NH_2$) optionally substituted by 1 or 2 substituents selected from (1) a $C_{1-6}$alkyl group optionally substituted by 1 to 3 OH groups, (2) a $C_{3-10}$ cycloalkyl group optionally substituted by 1 to 3 OH groups and (3) a 3- to 14-membered non-aromatic heterocyclic group; or $Z^2$ and $Z^3$ are bonded to each other to form a 5- to 14-membered aromatic heterocycle.

In such embodiments, Cy is

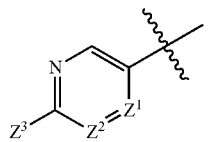

the combination of $Z^1$ and $Z^2$ ($Z^1$, $Z^2$) is (CH, N); and Cy is optionally further substituted by 1 to 3 $C_{1-6}$alkyl groups; and $Z^3$ is an amino group (—$NH_2$) optionally substituted by 1-2 substituents selected from (1) a $C_{1-6}$alkyl group optionally substituted by 1 to 3 OH groups, (2) a $C_{3-10}$cycloalkyl group optionally substituted by 1 to 3 hydroxy groups and (3) a 3- to 14-membered non-aromatic heterocyclic group.

In the compounds of the invention, A is selected from the group consisting of phenyl; naphthyl; and 5-, 6-, 7-, 8-, 9-, 10- or 11-membered heteroaryl group comprising 1 N heteroatom and optionally 1 or 2 further heteroatoms selected from the group consisting of N, S and O (preferably N and S, more preferably N).

In one embodiment, A is selected from the group consisting of 5-, 6-, 7-, 8-, 9-, 10- or 11-membered heteroaryl group comprising 1 N heteroatom and optionally 1 or 2 further heteroatoms selected from the group consisting of N, S and O (preferably N and S, more preferably N). For example A is selected from the group consisting of pyridyl (i.e., pyridinyl), pyrimidinyl, pyrazinyl, pyridazinyl, triazinyl, quinolyl, tetrahydroquinolyl, isoquinolyl, tetrahydroisoquinolyl, imidazolyl, thiazolyl, indolyl, pyrryl, oxazolyl, benzthiazolyl, isoxazolyl, pyrazolyl, triazolyl, indazolyl, 1,2,4-thiadiazolyl, isothiazolyl, benzimidazolyl, and indolinyl. In one especially preferred embodiment, A is pyridyl.

In one embodiment, A is selected from the group consisting of phenyl; naphthyl; and 6-, 7-, 8-, 9-, 10- or 11-membered heteroaryl group comprising 1 N heteroatom and optionally 1 or 2 further heteroatoms selected from the group consisting of N, S and O (preferably N and S, more preferably N).

In another embodiment, A is selected from the group consisting of 6-, 7-, 8-, 9-, 10- or 11-membered heteroaryl group comprising 1 N heteroatom and optionally 1 or 2 further heteroatoms selected from the group consisting of N, S and O (preferably N and S, more preferably N).

In one preferred embodiment, A is selected from the group consisting of pyridyl (i.e., pyridinyl), pyrimidinyl, pyrazinyl, pyridazinyl, indolyl, indazolyl, benzimidazolyl, and indolinyl.

In one preferred embodiment, A is selected from the group consisting of phenyl, pyridyl, pyrazinyl, pyridazinyl and pyrimidinyl.

In one especially preferred embodiment, A is a pyridyl group. In another preferred embodiment, A is a phenyl group or a pyridyl.

In one preferred embodiment, A is selected from the group consisting of:

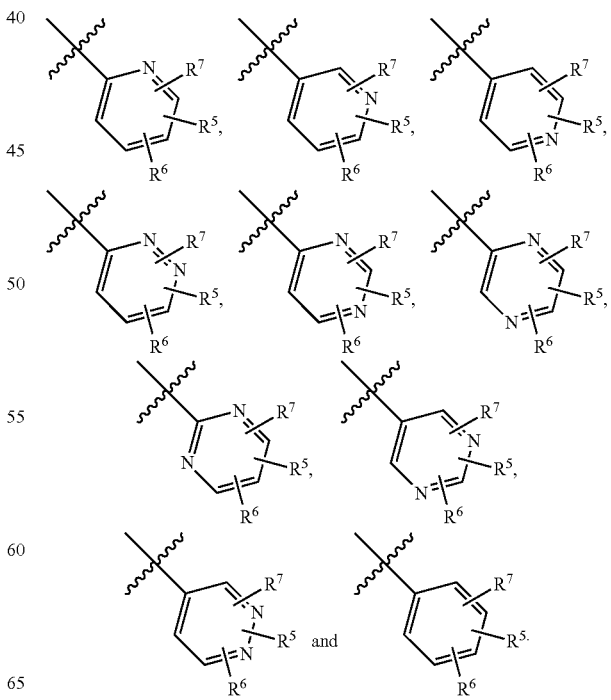

More preferably, A is selected from the group consisting of:

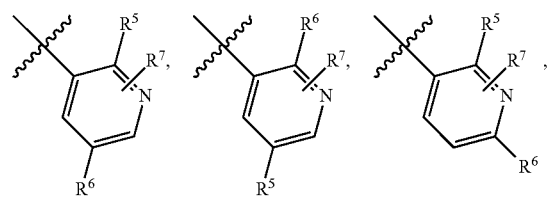

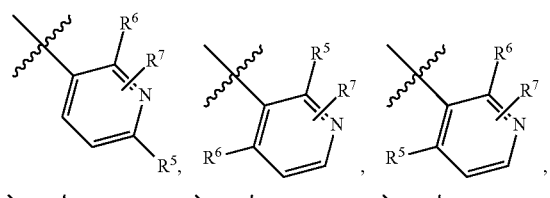

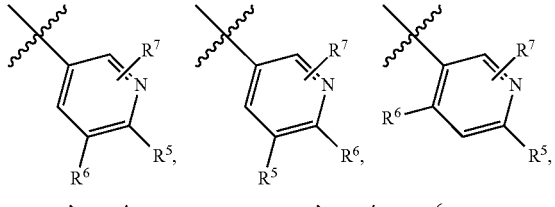

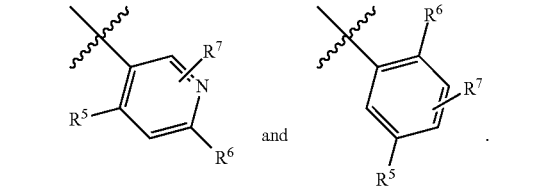

and

In one preferred embodiment, $R^7$ is hydrogen, and A is selected from the group consisting of:

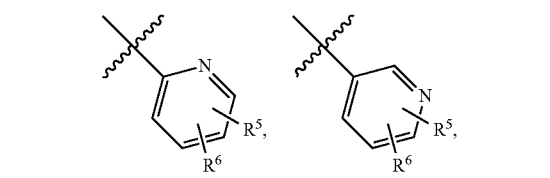

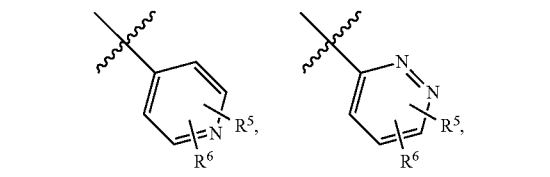

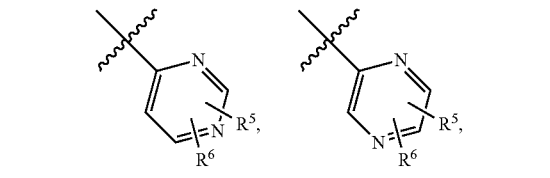

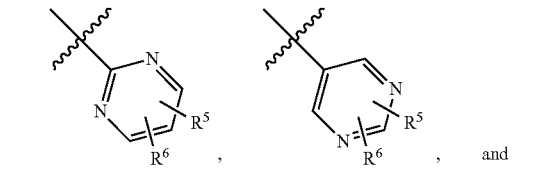

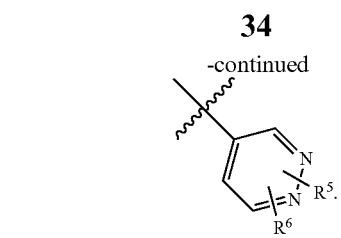

In another preferred embodiment, $R^7$ is hydrogen, and A is selected from the group consisting of:

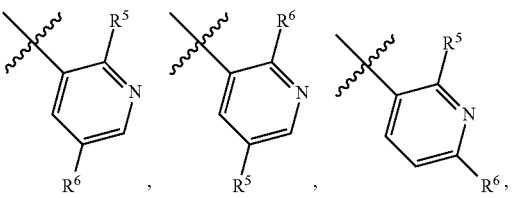

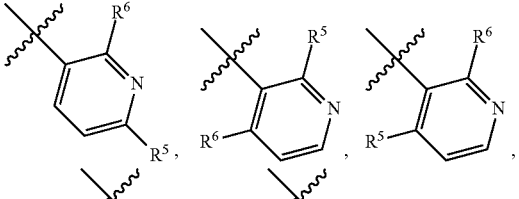

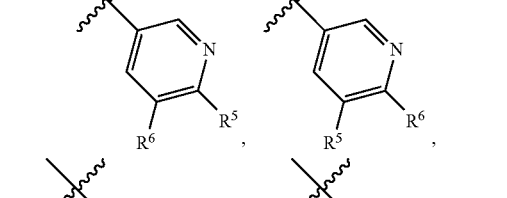

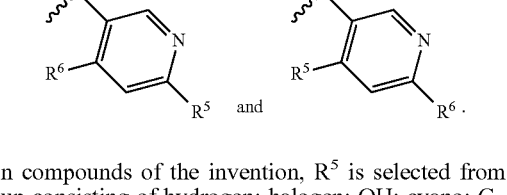

In compounds of the invention, $R^5$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; NH($C_{1-6}$alkyl); and N($C_{1-6}$alkyl)$_2$.

In one preferred embodiment, $R^5$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen.

In one preferred embodiment, $R^5$ is selected from the group consisting of hydrogen; halogen; OH; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen.

In one preferred embodiment, $R^5$ is selected from the group consisting of hydrogen; halogen; OH; $C_{1-3}$alkyl optionally substituted by 1, 2 or 3 groups independently selected from the group consisting of halogen, OH and O—$C_{1-3}$alkyl optionally substituted by 1, 2 or 3 halogen; and O—$C_{1-3}$alkyl optionally substituted by 1, 2 or 3 groups independently selected from the group consisting of halogen, OH and O—$C_{1-3}$alkyl optionally substituted by 1, 2 or 3 halogen.

In one embodiment, $R^5$ is selected from the group consisting of hydrogen; halogen; OH; $C_{1-6}$ alkyl optionally substituted by 1, 2 or 3 groups independently selected from the group consisting of halogen and O—$C_{1-3}$alkyl; and O—$C_{1-6}$alkyl optionally substituted by 1, 2 or 3 halogen groups.

In another embodiment, $R^5$ is selected from the group consisting of hydrogen; halogen; OH; $C_{1-6}$alkyl optionally substituted by 1, 2 or 3 groups independently selected from the group consisting of halogen and O—$C_{1-3}$alkyl; and O—$C_{1-6}$alkyl optionally substituted by 1, 2 or 3 halogen groups.

In compounds of the invention, $R^6$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; $NH(C_{1-6}alkyl)$; $N(C_{1-6}alkyl)_2$; optionally substituted phenyl; optionally substituted naphthyl; optionally substituted 5-, 6-, 7-, 8-, 9-, 10- or 11-membered heteroaryl group comprising 1 N heteroatom and optionally 1 or 2 further heteroatoms independently selected from the group consisting of N, S and O (preferably N and S); optionally substituted 5-, 6-, 7-, 8-, 9-, 10- or 11-membered non-aromatic heterocycle group comprising 1 N heteroatom and optionally 1 or 2 further heteroatoms independently selected from the group consisting of N, S and O (preferably N and S); and optionally substituted $C_{3-10}$cycloalkyl; wherein said phenyl, naphthyl, 5-, 6-, 7-, 8-, 9-, 10- or 11-membered heteroaryl group, 5-, 6-, 7-, 8-, 9-, 10- or 11-membered non-aromatic heterocycle group, and $C_{3-11}$cycloalkyl are optionally substituted with 1, 2 or 3 groups independently selected from the group consisting of halogen; OH; $C_{1-3}$alkyl optionally substituted by 1, 2 or 3 groups independently selected from the group consisting of halogen, OH and O—$C_{1-3}$alkyl optionally substituted by 1, 2 or 3 halogen; O—$C_{1-3}$alkyl optionally substituted by 1, 2 or 3 groups independently selected from the group consisting of halogen, OH and O—$C_{1-3}$alkyl optionally substituted by 1, 2 or 3 halogen.

In embodiments wherein $R^6$ is optionally substituted phenyl, optionally substituted naphthyl, optionally substituted 5-, 6-, 7-, 8-, 9-, 10- or 11-membered heteroaryl group, optionally substituted 5-, 6-, 7-, 8-, 9-, 10- or 11-membered non-aromatic heterocycle group, or optionally substituted $C_{3-11}$cycloalkyl, preferably said phenyl, naphthyl, 5-, 6-, 7-, 8-, 9-, 10- or 11-membered heteroaryl group, 5-, 6-, 7-, 8-, 9-, 10- or 11-membered non-aromatic heterocycle group, or $C_{3-11}$cycloalkyl is optionally substituted with 1, 2 or 3 groups independently selected from the group consisting of halogen; OH; $C_{1-3}$alkyl optionally substituted by 1, 2 or 3 groups independently selected from the group consisting of halogen; O—$C_{1-3}$alkyl optionally substituted by 1, 2 or 3 halogen. For example, said phenyl, naphthyl, 5-, 6-, 7-, 8-, 9-, 10- or 11-membered heteroaryl group, 5-, 6-, 7-, 8-, 9-, 10- or 11-membered non-aromatic heterocycle group, or $C_{3-11}$cycloalkyl is optionally substituted with 1 or 2 groups independently selected from the group consisting of halogen; OH; $C_{1-3}$alkyl optionally substituted by 1, 2 or 3 halogen; O—$C_{1-3}$alkyl optionally substituted by 1, 2 or 3 halogen. For example, said phenyl, naphthyl, 5-, 6-, 7-, 8-, 9-, 10- or 11-membered heteroaryl group, 5-, 6-, 7-, 8-, 9-, 10- or 11-membered non-aromatic heterocycle group, or $C_{3-11}$cycloalkyl is optionally substituted with 1 group selected from the group consisting of halogen; OH; $C_{1-3}$alkyl optionally substituted by 1, 2 or 3 groups independently selected from the group consisting of halogen; O—$C_{1-3}$alkyl optionally substituted by 1, 2 or 3 halogen.

In one preferred embodiment, $R^6$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; $NH(C_{1-6}alkyl)$; and $N(C_{1-6}alkyl)_2$.

In one preferred embodiment, $R^6$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen.

In one preferred embodiment, $R^6$ is selected from the group consisting of hydrogen; halogen; OH; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen.

In another preferred embodiment, $R^6$ is selected from the group consisting of hydrogen; halogen; OH; $C_{1-6}$alkyl optionally substituted by 1, 2 or 3 groups independently selected from the group consisting of halogen, OH and O—$C_{1-3}$alky optionally substituted by 1, 2 or 3 halogen I; and O—$C_{1-6}$alkyl optionally substituted by 1, 2 or 3 groups independently selected from the group consisting of halogen, OH and O—$C_{1-3}$alkyl optionally substituted by 1, 2 or 3 halogen.

In another preferred embodiment, $R^6$ is selected from the group consisting of hydrogen; halogen; OH; $C_{1-3}$alkyl optionally substituted by 1, 2 or 3 groups independently selected from the group consisting of halogen, OH and O—$C_{1-3}$alky optionally substituted by 1, 2 or 3 halogen I; and O—$C_{1-3}$alkyl optionally substituted by 1, 2 or 3 groups independently selected from the group consisting of halogen, OH and O—$C_{1-3}$alkyl optionally substituted by 1, 2 or 3 halogen.

In one embodiment, $R^6$ is selected from the group consisting of hydrogen; halogen; OH; $C_{1-6}$alkyl optionally substituted by 1, 2 or 3 groups independently selected from the group consisting of halogen and O—$C_{1-3}$alkyl optionally substituted by 1, 2 or 3 halogen; and O—$C_{1-6}$alkyl optionally substituted by 1, 2 or 3 halogen groups.

In another embodiment, $R^6$ is selected from the group consisting of hydrogen; halogen; OH; $C_{1-6}$alkyl optionally substituted by 1, 2 or 3 groups independently selected from the group consisting of halogen and O—$C_{1-3}$alkyl optionally substituted by 1, 2 or 3 halogen; and O—$C_{1-6}$alkyl optionally substituted by 1, 2 or 3 halogen groups.

In compounds of the invention, $R^7$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; $NH(C_{1-6}$alkyl); and $N(C_{1-6}$alkyl$)_2$.

In one preferred embodiment, $R^7$ is hydrogen.

In one embodiment, $R^7$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen.

In another embodiment, $R^7$ is selected from the group consisting of hydrogen; halogen; OH; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen.

In another embodiment, $R^7$ is selected from the group consisting of hydrogen; halogen; OH; $C_{1-3}$alkyl optionally substituted by 1, 2 or 3 groups independently selected from the group consisting of halogen, OH and O—$C_{1-3}$alkyl optionally substituted by 1, 2 or 3 halogen; and O—$C_{1-3}$alkyl optionally substituted by 1, 2 or 3 groups independently selected from the group consisting of halogen, OH and O—$C_{1-3}$alkyl optionally substituted by 1, 2 or 3 halogen.

In one embodiment, $R^7$ is selected from the group consisting of hydrogen; halogen; OH; $C_{1-6}$alkyl optionally substituted by 1, 2 or 3 groups independently selected from the group consisting of halogen and O—$C_{1-3}$alkyl optionally substituted by 1, 2 or 3 halogen; and O—$C_{1-6}$alkyl optionally substituted by 1, 2 or 3 halogen groups.

In another embodiment, $R^7$ is selected from the group consisting of halogen; OH; $C_{1-6}$alkyl optionally substituted by 1, 2 or 3 groups independently selected from the group consisting of halogen and O—$C_{1-3}$alkyl optionally substituted by 1, 2 or 3 halogen; and O—$C_{1-6}$alkyl optionally substituted by 1, 2 or 3 halogen groups.

In one especially preferred embodiment $R^5$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; $NH(C_{1-6}$alkyl); and $N(C_{1-6}$alkyl$)_2$;

$R^6$ is selected from the group consisting of hydrogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; $NH(C_{1-6}$ alkyl); $N(C_{1-6}$alkyl$)_2$; optionally substituted phenyl; optionally substituted naphthyl; optionally substituted 5-, 6-, 7-, 8-, 9-, 10- or 11-membered heteroaryl group comprising 1 N heteroatom and optionally 1 or 2 further heteroatoms independently selected from the group consisting of N, S and O (preferably N and S); optionally substituted 5-, 6-, 7-, 8-, 9-, 10- or 11-membered non-aromatic heterocycle group comprising 1 N heteroatom and optionally 1 or 2 further heteroatoms independently selected from the group consisting of N, S and O (preferably N and 5); and optionally substituted $C_{3-10}$cycloalkyl; wherein said phenyl, naphthyl, 5-, 6-, 7-, 8-, 9-, 10- or 11-membered heteroaryl group, 5-, 6-, 7-, 8-, 9-, 10- or 11-membered non-aromatic heterocycle group, and $C_{3-11}$cycloalkyl are optionally substituted with 1, 2 or 3 groups independently selected from the group consisting of halogen; OH; $C_{1-3}$alkyl optionally substituted by 1, 2 or 3 groups independently selected from the group consisting of halogen, OH and O—$C_{1-3}$alkyl optionally substituted by 1, 2 or 3 halogen; O—$C_{1-3}$alkyl optionally substituted by 1, 2 or 3 groups independently selected from the group consisting of halogen, OH and O—$C_{1-3}$alkyl optionally substituted by 1, 2 or 3 halogen; and $R^7$ is selected from the group consisting of hydrogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; $NH(C_{1-6}$alkyl); and $N(C_{1-6}$alkyl$)_2$. More preferably, $R^7$ is hydrogen.

In another especially preferred embodiment, $R^5$ is selected from the group consisting of hydrogen; halogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; $NH(C_{1-6}$alkyl); and $N(C_{2-6}$alkyl$)_2$;

$R^6$ is selected from the group consisting of hydrogen; OH; cyano; $C_{1-6}$alkyl optionally substituted by 1, 2 or 3 groups independently selected from the group consisting of halogen, OH and O—$C_{2-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; $NH(C_{1-6}$alkyl); and $N(C_{1-6}$alkyl$)_2$; and $R^7$ is selected from the group consisting of hydrogen; OH; cyano; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen; $NH_2$; $NH(C_{1-6}$alkyl); and $N(C_{1-6}$alkyl$)_2$. More preferably, $R^7$ is hydrogen.

In another especially preferred embodiment, $R^5$ is selected from the group consisting of hydrogen; halogen; OH; $C_{1-6}$alkyl optionally substituted by 1, 2 or 3 groups independently selected from the group consisting of halogen and O—$C_{1-3}$alkyl; and O—$C_{1-6}$alkyl optionally substituted by 1, 2 or 3 halogen groups;

$R^6$ is selected from the group consisting of hydrogen; OH; $C_{1-6}$alkyl optionally substituted by 1, 2 or 3 groups independently selected from the group consisting of halogen and O—$C_{1-3}$alkyl optionally substituted by 1, 2 or 3 halogen; and O—$C_{1-6}$alkyl optionally substituted by 1, 2 or 3 halogen groups; and $R^7$ is selected from the group consisting of hydrogen; OH; $C_{1-6}$alkyl optionally substituted by 1, 2 or 3 groups independently selected from the group consisting of halogen and O—$C_{1-3}$alkyl optionally substituted by 1, 2 or 3 halogen; and O—$C_{1-6}$alkyl optionally substituted by 1, 2 or 3 halogen groups. More preferably, $R^7$ is hydrogen.

In one preferred embodiment A is selected from the group consisting of:

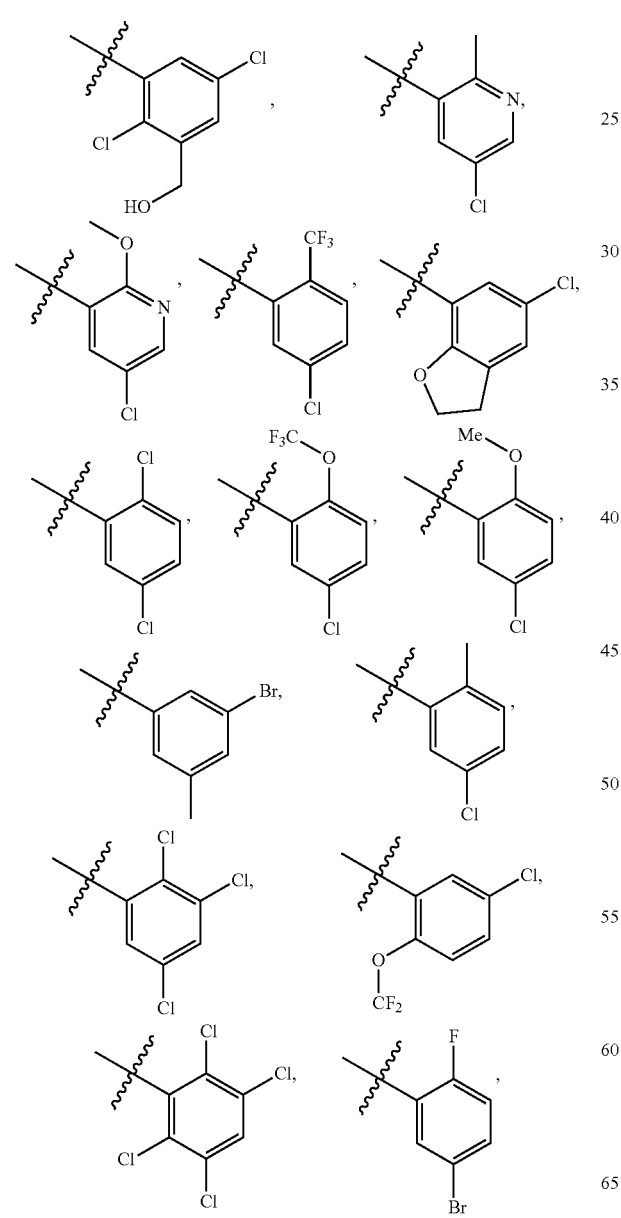

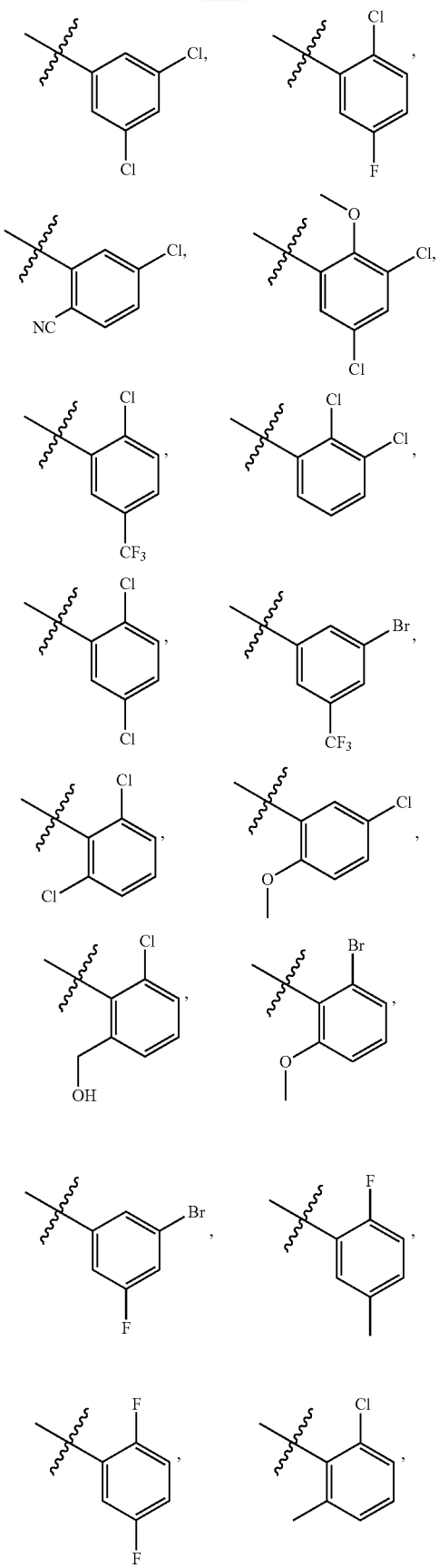

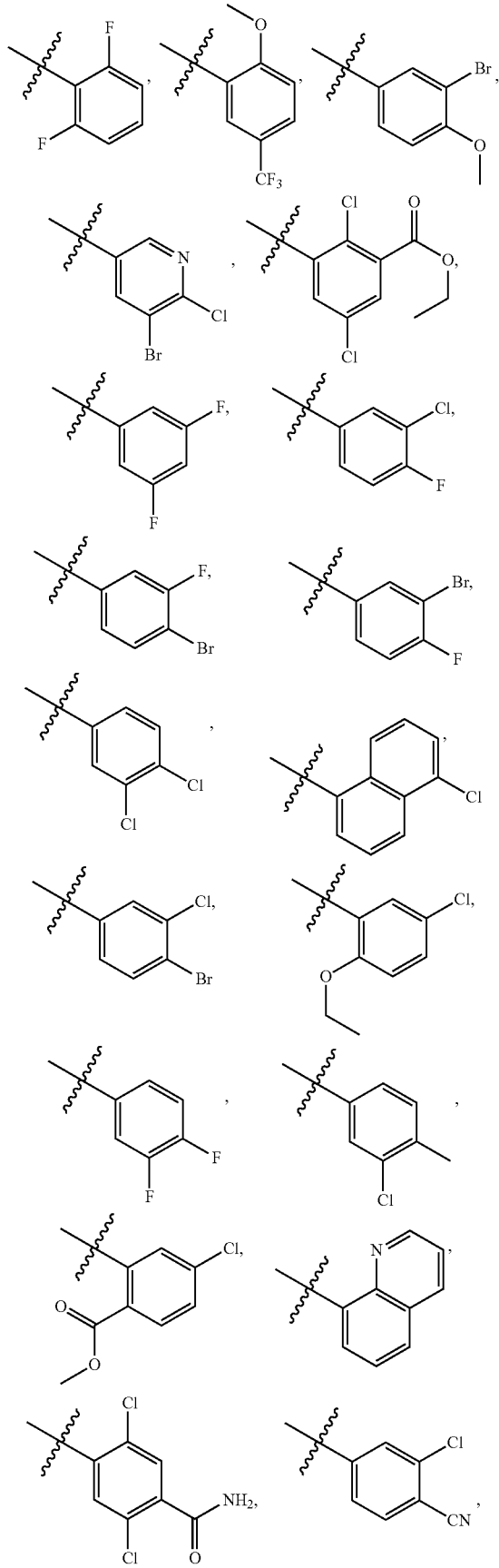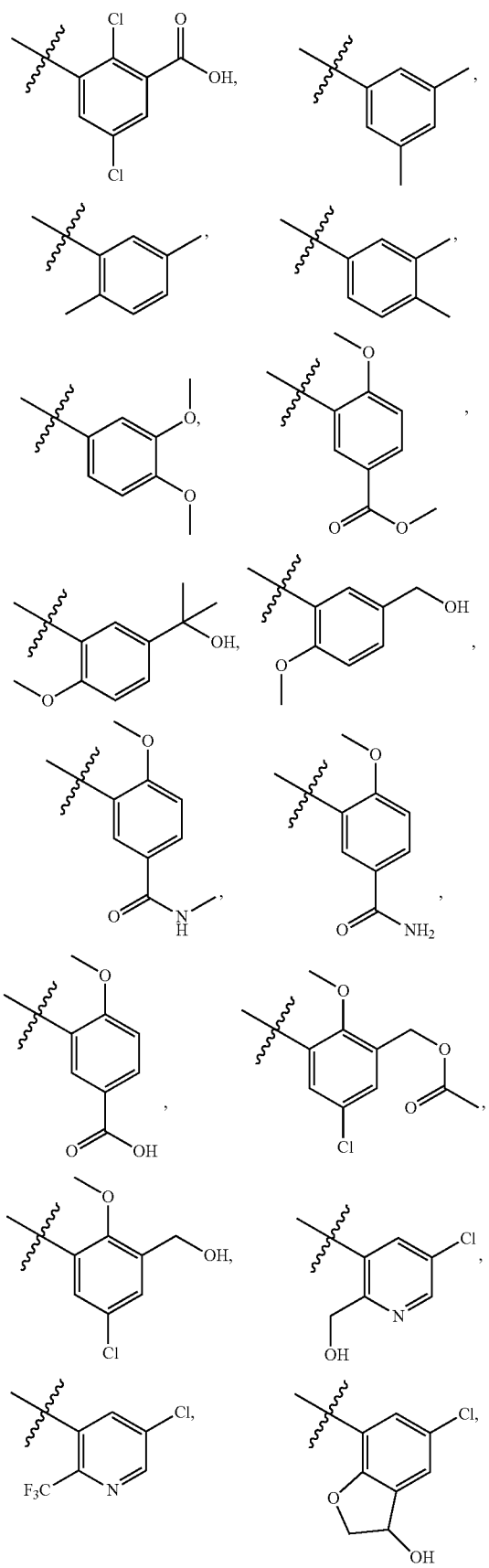

-continued

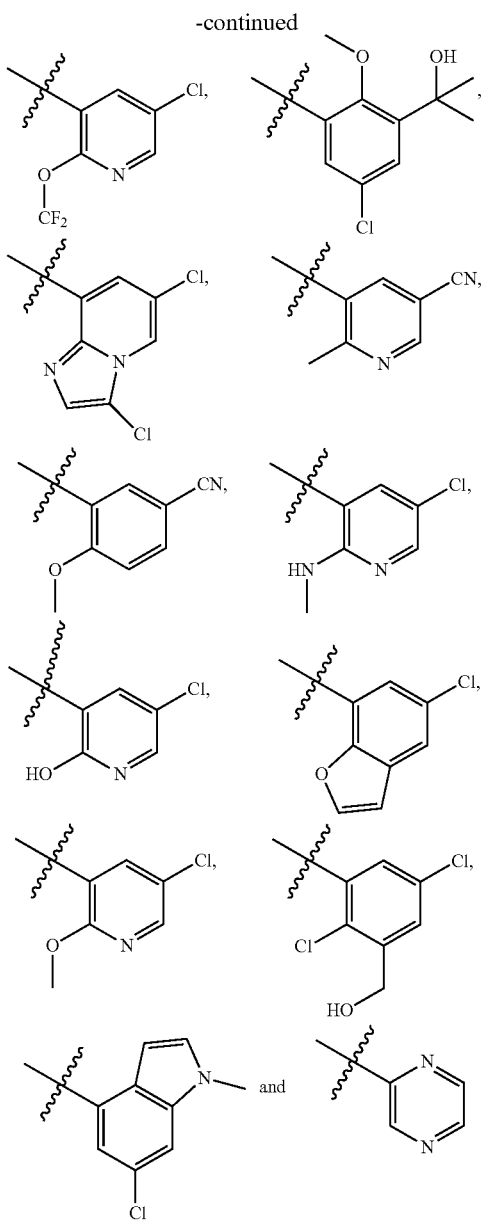

In certain embodiments, A is an optionally substituted 6-membered aryl or heteroaryl ring of formula B:

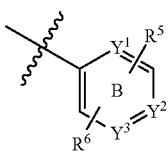

wherein two of $Y^1$, $Y^2$ and $Y^3$ are CH and the remaining one is a CH or N;

$R^5$ is selected from the group consisting of halogen; OH; $C_{1-3}$alkyl optionally substituted by 1, 2 or 3 groups independently selected from the group consisting of halogen, OH and O—$C_{1-3}$alkyl; and O—$C_{1-3}$alkyl optionally substituted by 1, 2 or 3 groups independently selected from the group consisting of halogen, OH and O—$C_{1-3}$alkyl;

$R^6$ is selected from the group consisting of halogen; OH; $C_{1-3}$alkyl optionally substituted by 1, 2 or 3 groups independently selected from the group consisting of halogen, OH and O—$C_{1-3}$alkyl; O—$C_{1-3}$alkyl optionally substituted by 1, 2 or 3 groups independently selected from the group consisting of halogen, OH and O—$C_{1-3}$alkyl; and a ring for formula:

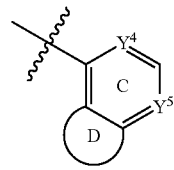

wherein ring C is an optionally substituted 6-membered aromatic ring; and ring D is an optionally further substituted 5-, 6- or 7-membered ring;

one of $Y^4$ and $Y^4$ is a CH, and the other one is CH or a N;

wherein said C ring is optionally substituted with a halogen; OH; $C_{1-3}$alkyl optionally substituted by 1, 2 or 3 groups independently selected from the group consisting of halogen, OH and O—$C_{1-3}$alkyl; O—$C_{1-3}$alkyl optionally substituted by 1, 2 or 3 groups independently selected from the group consisting of halogen, OH and O—$C_{1-3}$alkyl; and wherein said D ring is optionally substituted with a halogen; OH; $C_{1-3}$alkyl optionally substituted by 1, 2 or 3 groups independently selected from the group consisting of halogen, OH and O—$C_{1-3}$alkyl; O—$C_{1-3}$alkyl optionally substituted by 1, 2 or 3 groups independently selected from the group consisting of halogen, OH and O—$C_{1-3}$alkyl.

In certain embodiments, A is (1) the formula:

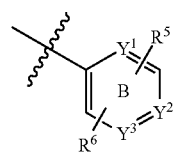

wherein the combination of $Y^1$, $Y^2$ and $Y^3$ ($Y^1$, $Y^2$, $Y^3$) is (CH, CH, CH) or (CH, CH, N);

$R^5$ is (1) a fluorine atom, a chlorine atom, a bromine atom, (2) methyl, trifluoromethyl, or (3) a hydroxy group optionally substituted by methyl, difluoromethyl or trifluoromethyl;

$R^6$ is (1) a halogen atom, (2) a cyano group, (3) a $C_{1-6}$alkyl group optionally substituted by 1 to 3 substituents selected from a halogen atom and a hydroxy group, (4) a $C_{1-6}$alkoxy group optionally substituted by 1 to 3 halogen atoms or (5) a mono- or di-$C_{1-6}$alkylamino group;

and ring B is optionally further substituted by 1 to 3 substituents selected from (1) a halogen atom, (2) a $C_{1-6}$alkyl group optionally substituted by 1 to 3 hydroxy groups and (3) a $C_{1-6}$alkoxy group, or (2) the formula:

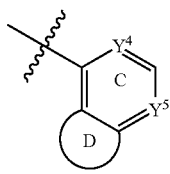

wherein the combination of $Y^4$ and $Y^5$ ($Y^4$, $Y^5$) is (CH, CH);
ring C is optionally further substituted by 1 to 3 halogen atoms;
ring D is a 5- to 7-membered aromatic heterocycle or a 5- to 7-membered non-aromatic heterocycle;
ring D is optionally further substituted by 1 to 3 substituents selected from (1) a halogen atom and (2) a hydroxy group.

In such embodiments, $R^4$ may be a hydrogen atom, a fluorine atom or a chlorine atom.

In such embodiments, $R^3$ may be a fluorine atom or a chlorine atom.

In such embodiments, Cy may be

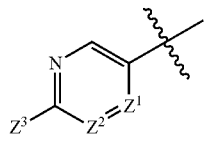

the combination of $Z^1$ and $Z^2$ ($Z^1$, $Z^2$) is (CH, N), (N, CH) or (N, N);
Cy is optionally further substituted by 1 to 3 substituents selected from (1) a $C_{1-6}$alkyl group and (2) an amino group; and $Z^3$ is an amino group optionally substituted by 1-2 substituents selected from (1) a $C_{1-6}$alkyl group optionally substituted by 1 to 3 substituents selected from a hydroxy group and a 3- to 14-membered non-aromatic heterocyclic group, (2) a $C_{3-10}$cycloalkyl group optionally substituted by 1 to 3 hydroxy groups, (3) a 3- to 14-membered non-aromatic heterocyclic group and (4) a 5- to 14-membered aromatic heterocyclic group optionally substituted by 1 to 3 $C_{1-6}$alkyl groups; or $Z^2$ and $Z^3$ are bonded to each other to form a 5- to 14-membered aromatic heterocycle.

In certain embodiments, A is (1) the formula:

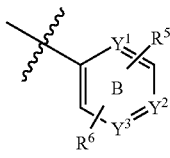

wherein the combination of $Y^1$, $Y^2$ and $Y^3$ ($Y^1$, $Y^2$, $Y^3$) is (CH, CH, CH) or (CH, CH, N); $R^5$ is (1) a chlorine atom, a bromine atom, (2) methyl, trifluoromethyl, or (3) a hydroxy group substituted by methyl or trifluoromethyl;
$R^6$ is (1) a halogen atom, (2) a $C_{1-6}$alkyl group optionally substituted by 1 to 3 substituents selected from a halogen atom and a hydroxy group or (3) a $C_{1-6}$alkoxy group optionally substituted by 1 to 3 halogen atoms;

ring B is optionally further substituted by 1 to 3 substituents selected from (1) a halogen atom and (2) a $C_{1-6}$alkyl group optionally substituted by 1 to 3 hydroxy groups, or (2) the formula:

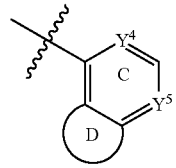

wherein the combination of $Y^4$ and $Y^5$ ($Y^4$, $Y^5$) is (carbon atom, carbon atom);
ring C is optionally further substituted by 1 to 3 halogen atoms;
ring D is a 5- to 7-membered non-aromatic heterocycle;

In such embodiments, $R^4$ may be a hydrogen atom, a fluorine atom or a chlorine atom.

In such embodiments, $R^3$ may be a fluorine atom or a chlorine atom.

In such embodiments, Cy may be

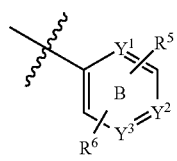

the combination of $Z^1$ and $Z^2$ ($Z^1$, $Z^2$) is (carbon atom, nitrogen atom), (nitrogen atom, carbon atom) or (nitrogen atom, nitrogen atom); and Cy is optionally further substituted by 1 to 3 $C_{1-6}$alkyl groups; and $Z^3$ is an amino group optionally substituted by 1-2 substituents selected from (1) a $C_{1-6}$alkyl group optionally substituted by 1 to 3 hydroxy groups, (2) a $C_{1-10}$cycloalkyl group optionally substituted by 1 to 3 hydroxy groups and (3) a 3- to 14-membered non-aromatic heterocyclic group; or $Z^2$ and $Z^3$ are bonded to each other to form a 5- to 14-membered aromatic heterocycle.

In certain embodiments, A is (1) the formula:

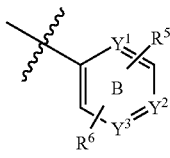

wherein the combination of $Y^1$, $Y^2$ and $Y^3$ ($Y^1$, $Y^2$, $Y^3$) is (CH, CH, CH) or (CH, CH, N);
$R^5$ is (1) a chlorine atom, a bromine atom, (2) methyl, trifluoromethyl, or (3) a hydroxy group substituted by methyl or trifluoromethyl;
$R^6$ is (1) a halogen atom, (2) a $C_{1-6}$alkyl group optionally substituted by 1 to 3 substituents selected from a halogen atom and a hydroxy group or (3) a $C_{1-6}$alkoxy group optionally substituted by 1 to 3 halogen atoms;
ring B is optionally further substituted by 1 to 3 substituents selected from (1) a halogen atom and (2) a $C_{1-6}$alkyl group optionally substituted by 1 to 3 hydroxy groups.

In such embodiments, R⁴ may be a hydrogen atom, a fluorine atom or a chlorine atom.

In such embodiments, R³ may be a fluorine atom or a chlorine atom.

In such embodiments, Cy may be

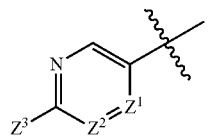

the combination of $Z^1$ and $Z^2$ ($Z^1$, $Z^2$) is (carbon atom, nitrogen atom);

and Cy is optionally further substituted by 1 to 3 $C_{1-6}$alkyl groups; and $Z^3$ is an amino group optionally substituted by 1-2 substituents selected from (1) a $C_{1-6}$alkyl group optionally substituted by 1 to 3 hydroxy groups, (2) a $C_{3-30}$cycloalkyl group optionally substituted by 1 to 3 hydroxy groups and (3) a 3- to 14-membered non-aromatic heterocyclic group, or a salt thereof.

In one preferred embodiment, the compound of the invention is a compound of formula (IA):

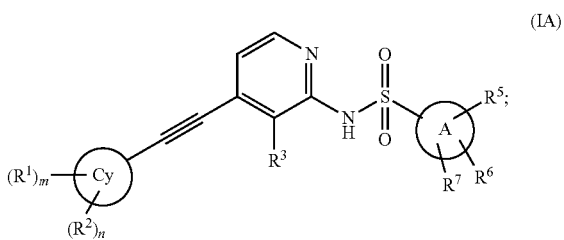

(IA)

Cy is a 5- or 6-membered heteroaryl group comprising at least 1 N heteroatom and optionally 1 or 2 further heteroatoms selected from the group consisting of N and S (preferably N); or Cy is a 9- or 10-membered heteroaryl group comprising at least 1 N heteroatom and optionally 1 or 2 further heteroatoms selected from the group consisting of N and S (preferably N);

$R^1$ is selected from the group consisting of —NH₂; —NR^A(C_{1-6}alkyl); and —NR^A(C_{1-6}alkyl substituted by 1, 2 or 3 groups independently selected from the group consisting of OH, halogen, and O—$C_{1-3}$alkyl optionally substituted by 1, 2 or 3 halogen);

$R^A$ is hydrogen;

A is selected from the group consisting of 5-, 6-, 7-, 8-, 9-, 10- or 11-membered heteroaryl group comprising 1 N heteroatom and optionally 1 or 2 further heteroatoms selected from the group consisting of N, S and O (preferably N and S, more preferably N);

$R^5$ is selected from the group consisting of hydrogen; halogen; OH; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen;

$R^6$ is selected from the group consisting of hydrogen; halogen; OH; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen; and $R^7$ is selected from the group consisting of hydrogen; halogen; OH; $C_{1-6}$alkyl optionally substituted by 1, 2 or 3 groups independently selected from the group consisting of halogen, OH and O—$C_{1-3}$alkyl optionally substituted by 1, 2 or 3 halogen; and O—$C_{1-6}$alkyl optionally substituted by 1, 2 or 3 groups independently selected from the group consisting of halogen, OH and O—$C_{1-3}$alkyl optionally substituted by 1, 2 or 3 halogen.

In such embodiments, preferably R³ is F or Cl. Most preferably, R³ is F.

In such embodiments, preferably m is 1; and n is 0, 1 or 2 (more preferably n is 0 or 1).

In certain preferred embodiments, the compound of the invention is a compound of the invention described in the Examples section below, or a pharmaceutically acceptable ester, amide, carbamate or salt thereof, including a pharmaceutically acceptable salt of such an ester, amide or carbamate. In particular, the compound of the invention may be a compound selected from the group consisting of:

N-{4-[2-(2-aminopyrimidin-5-yl)ethynyl]-3-fluoropyridin-2-yl}-5-chloro-2-methoxypyridine-3-sulfonamide (example 1);

N-{4-[2-(2-aminopyrimidin-5-yl)ethynyl]-3-chloropyridin-2-yl}-5-chloro-2-methoxypyridine-3-sulfonamide (example 2);

5-chloro-N-[3-fluoro-4-(2-{1H-pyrazolo[3,4-b]pyridin-5-yl}ethynyl)pyridin-2-yl]-2-methoxypyridine-3-sulfonamide (example 3);

N-{4-[2-(8-amino-1,7-naphthyridin-5-yl)ethynyl]-3-fluoropyridin-2-yl}-5-chloro-2-methoxypyridine-3-sulfonamide (example 4);

5-chloro-N-{4-[2-(pyrido[3,4-b]pyrazin-8-yl)ethynyl]-3-fluoropyridin-2-yl}-2-methoxypyridine-3-sulfonamide (example 5);

5-chloro-N-{4-[2-(1,6-naphthyridin-8-yl)ethynyl]-3-fluoropyridin-2-yl}-2-methoxypyridine-3-sulfonamide (example 6);

N-{4-[2-(7-aminopyrazolo[1,5-a]pyrimidin-3-yl)ethynyl]-3-fluoropyridin-2-yl}-5-chloro-2-methoxypyridine-3-sulfonamide (example 7);

N-{4-[2-(8-aminoimidazo[1,2-a]pyridin-3-yl)ethynyl]-3-fluoropyridin-2-yl}-5-chloro-2-methoxypyridine-3-sulfonamide (example 8);

5-chloro N-{4-[2-(quinoxalin-2-yl)ethynyl]-3-fluoropyridin-2-yl}-2-methoxypyridine-3-sulfonamide (example 9);

N-{4-[2-(2-aminopyrimidin-5-yl)ethynyl]-3,5-difluoropyridin-2-yl}-5-chloro-2-methoxypyridine-3-sulfonamide (example 10);

N-{4-[2-(8-aminoimidazo[1,2-a]pyrazin-3-yl)ethynyl]-3-fluoropyridin-2-yl}-5-chloro-2-methoxypyridine-3-sulfonamide (example 11);

5-chloro-N-[3-fluoro-4-(2-{1H-pyrazolo[3,4-b]pyridin-5-yl}ethynyl)pyridin-2-yl]-2-methoxybenzene-1-sulfonamide (example 12);

N-{4-[2-(2-aminopyrimidin-5-yl)ethynyl]-3-fluoropyridin-2-yl}-5-chloro-2-methoxybenzene-1-sulfonamide (example 13);

2,5-dichloro-N-[3-fluoro-4-(2-{1H-pyrazolo[3,4-b]pyridin-5-yl}ethynyl)pyridin-2-yl]benzene-1-sulfonamide (example 14);

N-{4-[2-(2-aminopyrimidin-5-yl)ethynyl]-3-fluoropyridin-2-yl}-2,5-dichlorobenzene-1-sulfonamide (example 15);

N-{4-[2-(2-aminopyrimidin-5-yl)ethynyl]-3-fluoropyridin-2-yl}-2,5-dichloro-3-(hydroxymethyl)benzene-1-sulfonamide (example 16);

2,5-dichloro-N-[3-fluoro-4-(2-{1H-pyrazolo[3,4-b]pyridin-5-yl}ethynyl)pyridin-2-yl]-3-(hydroxymethyl)benzene-1-sulfonamide (example 17);

5-chloro-N-[3-fluoro-4-(2-{1-methyl-1H-imidazo[4,5-c]pyridin-7-yl}ethynyl)pyridin-2-yl]-2-methoxypyridine-3-sulfonamide (example 18);

5-chloro-N-[3-fluoro-4-(2-{[1,3]thiazolo[4,5-c]pyridin-7-yl}ethynyl)pyridin-2-yl]-2-methoxypyridine-3-sulfonamide (example 19);

5-chloro-N-[3-fluoro-4-(2-{1-methyl-1H-pyrazolo[3,4-c]pyridin-4-yl}ethynyl)pyridin-2-yl]-2-methoxypyridine-3-sulfonamide (example 20);

5-chloro-N-[3-fluoro-4-(2-{1H-pyrazolo[3,4-c]pyridin-4-yl}ethynyl)pyridin-2-yl]-2-methoxypyridine-3-sulfonamide (example 21);

5-chloro-N-[3-fluoro-4-(2-{2-methyl-2H-pyrazolo[3,4-c]pyridin-4-yl}ethynyl)pyridin-2-yl]-2-methoxypyridine-3-sulfonamide (example 22);

5-chloro-N-[3-fluoro-4-(2-{1H-pyrazolo[4,3-c]pyridin-4-yl}ethynyl)pyridin-2-yl]-2-methoxypyridine-3-sulfonamide (example 23);

5-chloro-N-[3-fluoro-4-(2-{1-methyl-1H-pyrazolo[4,3-c]pyridin-7-yl}ethynyl)pyridin-2-yl]-2-methoxypyridine-3-sulfonamide (example 24);

5-chloro-N-(3-fluoro-4-{2-[2-(methylamino)pyrimidin-5-yl]ethynyl}pyridin-2-yl)-2-methoxypyridine-3-sulfonamide (example 25);

5-chloro-N-[3-fluoro-4-(2-{2-oxo-1H,2H,3H-imidazo[4,5-b]pyridin-6-yl}ethynyl)pyridin-2-yl]-2-methoxypyridine-3-sulfonamide (example 26);

5-chloro-N-[3-fluoro-4-(2-{1H-pyrazolo[3,4-b]pyrazin-5-yl}ethynyl)pyridin-2-yl]-2-methoxypyridine-3-sulfonamide (example 27);

5-chloro-N-[3-fluoro-4-(2-{2-oxo-1H,2H,3H-imidazo[4,5-b]pyrazin-5-yl}ethynyl)pyridin-2-yl]-2-methoxypyridine-3-sulfonamide (example 28);

5-chloro-N-[3-fluoro-4-(2-{3H-imidazo[4,5-b]pyridin-6-yl}ethynyl)pyridin-2-yl]-2-methoxypyridine-3-sulfonamide (example 29);

5-chloro-N-[3-fluoro-4-(2-{pyrazolo[1,5-a]pyrimidin-6-yl}ethynyl)pyridin-2-yl]-2-methoxypyridine-3-sulfonamide (example 30);

5-chloro-N-[3-fluoro-4-(2-{pyrazolo[1,5-a]pyrimidin-3-yl}ethynyl)pyridin-2-yl]-2-methoxypyridine-3-sulfonamide (example 31);

5-chloro-N-[3-fluoro-4-(2-{2-oxo-1H,2H,3H-imidazo[4,5-b]pyridin-6-yl}ethynyl)pyridin-2-yl]-2-methoxypyridine-3-sulfonamide (example 32);

5-chloro-N-[3-fluoro-4-(2-{3-methyl-1H-pyrazolo[3,4-b]pyridin-5-yl}ethynyl)pyridin-2-yl]-2-methoxypyridine-3-sulfonamide (example 33);

N-{4-[2-(2-amino-4-methylpyrimidin-5-yl)ethynyl]-3-fluoropyridin-2-yl}-5-chloro-2-methoxypyridine-3-sulfonamide (example 34);

N-{4-[2-(2-amino-4-methoxypyrimidin-5-yl)ethynyl]-3-fluoropyridin-2-yl}-5-chloro-2-methoxypyridine-3-sulfonamide (example 35);

5-chloro-N-[3-fluoro-4-(2-{1-methyl-2-oxo-1H,2H,3H-imidazo[4,5-b]pyridin-6-yl}ethynyl)pyridin-2-yl]-2-methoxypyridine-3-sulfonamide (example 36);

5-chloro-N-[3-fluoro-4-(2-{3-methoxy-1H-pyrazolo[3,4-b]pyridin-5-yl}ethynyl)pyridin-2-yl]-2-methoxypyridine-3-sulfonamide (example 37); and N-[4-(2-{5-aminopyrido[3,4-b]pyrazin-8-yl}ethynyl)-3-fluoropyridin-2-yl]-5-chloro-2-methoxypyridine-3-sulfonamide (example 38), or a pharmaceutically acceptable ester, amide, carbamate or salt thereof, including a pharmaceutically acceptable salt of such an ester, amide or carbamate.

In further preferred embodiments, the compound of the invention is a compound selected from:

5-chloro-N-[3-fluoro-4-(2-{imidazo[1,2-a]pyrazin-3-yl}ethynyl)pyridin-2-yl]-2-methoxypyridine-3-sulfonamide (example 26);

N-[4-(2-{8-aminoimidazo[1,2-b]pyridazin-3-yl}ethynyl)-3-fluoropyridin-2-yl]-5-chloro-2-methoxypyridine-3-sulfonamide;

N-[4-(2-{5-aminopyrido[3,4-b]pyrazin-8-yl)ethynyl}-3-fluoropyridin-2-yl]-5-chloro-2-methoxypyridine-3-sulphonamide (example 38);

5-chloro-N-[3-fluoro-4-(2-{1H-imidazo[4,5-b]pyrazin-5-yl}ethynyl)pyridin-2-yl]-2-methoxypyridine-3-sulfonamide;

5-chloro-N-(3-fluoro-4-{2-[2-(methylamino)pyrimidin-5-yl]ethynyl}pyridin-2-yl)-2-methoxypyridine-3-sulfonamide (example 25);

5-chloro-N-[3-fluoro-4-(2-{2-oxo-1H,2H,3H-imidazo[4,5-b]pyrazin-5-yl}ethynyl)pyridin-2-yl]-2-methoxypyridine-3-sulfonamide (example 28);

5-chloro-N-[3-fluoro-4-(2-{3-methyl-2-oxo-1H,2H,3H-imidazo[4,5-b]pyrazin-5-yl}ethynyl)pyridin-2-yl]-2-methoxypyridine-3-sulfonamide;

5-chloro-N-[3-fluoro-4-(2-{3H-imidazo[4,5-b]pyridin-6-yl}ethynyl)pyridin-2-yl]-2-methoxypyridine-3-sulfonamide (example 29);

5-chloro-N-{3-fluoro-4-[2-(2-methylpyrimidin-5-yl)ethynyl]pyridin-2-yl)-2-methoxypyridine-3-sulfonamide;

5-chloro-N-[3-fluoro-4-(2-{2-oxo-1H,2H,3H-imidazo[4,5-b]pyridin-6-yl}ethynyl)pyridin-2-yl]-2-methoxypyridine-3-sulfonamide (example 32);

5-chloro-N-[3-fluoro-4-(2-(1-methyl-2-oxo-1H,2H,3H-imidazo[4,5-b]pyridin-6-yl]ethynyl)pyridin-2-yl]-2-methoxypyridine-3-sulfonamide (example 36);

5-chloro-N-[3-fluoro-4-(2-{imidazo[1,2-b]pyridazin-3-yl}ethynyl)pyridin-2-yl]-2-methoxypyridine-3-sulfonamide;

N-{4-[2-(2-aminopyrimidin-5-yl)ethynyl]-3-fluoropyridin-2-yl}-5-chloro-2-methoxybenzene-1-sulfonamide (example 13);

5-chloro-N-[3-fluoro-4-(2-{imidazo[1,2-b]pyridazin-7-yl}ethynyl)pyridin-2-yl]-2-methoxypyridine-3-sulfonamide;

5-chloro-N-[3-fluoro-4-(2-{pyrazolo[1,5-a]pyrimidin-3-yl}ethynyl)pyridin-2-yl]-2-methoxypyridine-3-sulfonamide (example 31);

5-chloro-N-[3-fluoro-4-(2-{pyrazolo[1,5-a]pyrimidin-6-yl}ethynyl)pyridin-2-yl]-2-methoxypyridine-3-sulfonamide (example 30);

N-{4-[2-(5-amino-1,6-naphthyridin-8-yl)ethynyl]-3-fluoropyridin-2-yl}-5-chloro-2-methoxypyridine-3-sulfonamide;

N-[4-(2-{7-aminopyrazolo[1,5-a]pyridin-3-yl}ethynyl)-3-fluoropyridin-2-yl]-5-chloro-2-methoxypyridine-3-sulfonamide;

5-chloro-N-[3-fluoro-4-(2-{5H-pyrrolo[2,3-b]pyrazin-2-yl}ethynyl)pyridin-2-yl]-2-methoxypyridine-3-sulfonamide;

5-chloro-N-[3-fluoro-4-(2-{1H-pyrazolo[3,4-b]pyridin-5-yl}ethynyl)pyridin-2-yl]-2-methoxybenzene-1-sulfonamide (example 12);

N-{4-[2-(2-aminopyrimidin-5-yl)ethynyl]-3-fluoropyridin-2-yl}-2,5-dichlorobenzene-1-sulfonamide (example 15); and 2,5-dichloro-N-[3-fluoro-4-(2-(1H-pyrazolo[3,4-b]pyridin-5-yl}ethynyl)pyridin-2-yl]benzene-1-sulfonamide (example 14).

Depending upon the substituents present in the compounds of the invention, the compounds may form esters, amides, carbamates and/or salts. Salts of compounds of the invention which are suitable for use in medicine are those wherein a counterion is pharmaceutically acceptable. Such pharmaceutically acceptable salts are described in standard texts on salt formation, see for example: P. Stahl, et al., Handbook of Pharmaceutical Salts: Properties, Selection and Use (VCHA/Wiley-VCH, 2002), or S. M. Berge, et al., "Pharmaceutical Salts", *J. Pharm. Sci.*, 1977, 66, 1-19. However, salts having non-pharmaceutically acceptable counterions are within the scope of the present invention, for example, for use as intermediates in the preparation of the compounds of the invention and their pharmaceutically acceptable salts, and physiologically functional derivatives. By the term "physiologically functional derivative" is meant a chemical derivative of a compound of the invention having the same physiological function as the free compound of the invention, for example, by being convertible in the body thereto. Esters, amides and carbamates are examples of physiologically functional derivatives.

Suitable salts according to the invention include those formed with organic or inorganic acids. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_{1-4}$) alkyl or aryl sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutically acceptable acid addition salts.

Suitable salts according to the invention also include those formed with organic or inorganic bases. Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine.

Compounds of the invention may have an appropriate group converted to an ester, an amide or a carbamate. Typical ester and amide and carbamate groups formed from an —OH or —NHR$^G$ group in the compounds of the invention include OC(O)R$^G$, NR$^G$C(O)R$^G$, NR$^G$CO$_2$R$^G$, OSO$_2$R$^G$, and NR$^G$SO$_2$R$^G$, where R$^G$ is selected from the group consisting of $C_{1-8}$alkyl, $C_{2-8}$alkenyl, $C_{2-8}$alkynyl, $C_{3-8}$cycloalkyl and $C_{3-8}$cycloalkylC$_{1-8}$alkyl, haloC$_{1-8}$alkyl, dihaloC$_{1-8}$alkyl, trihaloC$_{1-8}$alkyl, phenyl and phenylC$_{1-4}$alkyl; more preferably R$^G$ is selected from the group consisting of $C_{1-8}$alkyl, $C_{2-6}$alkenyl, $C_{2-6}$alkynyl, $C_{3-8}$cycloalkyl and $C_{3-8}$cycloalkylC$_{1-8}$alkyl.

Those skilled in the art of organic chemistry will appreciate that many organic compounds can form complexes with solvents in which they are reacted, or from which they are precipitated or crystallized. These complexes are known as "solvates". A "pharmaceutically acceptable solvate" means a molecular complex comprising the compound of the invention and one or more pharmaceutically acceptable solvent molecules, for example, water or ethanol. For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al., Pharmaceutical Research, 12(7), 1995, 954-954, and Water-insoluble Drug Formulation, $2^{nd}$ edn, R. Liu, CRC Press, page 553, which are incorporated herein by reference. Accordingly, it will be understood by the skilled person that the compounds of the invention, as well as esters, amides, carbamates and/or salts thereof may therefore be present in the form of solvates, and these are also included within the scope of the present invention. Solvates of compounds of the invention, which are suitable for use in medicine, are those wherein the associated solvent is pharmaceutically acceptable. For example, as mentioned above, a hydrate is an example of a pharmaceutically acceptable solvate. However, solvates having non-pharmaceutically acceptable associated solvents may find use as intermediates in the preparation of the compounds of the invention and their pharmaceutically acceptable esters, amides, carbamates and/or salts thereof.

A compound which, upon administration to the recipient, is capable of being converted into a compound of the invention as described above, or an active metabolite or residue thereof, is known as a "prodrug". A prodrug may, for example, be converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the ACS Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

Definitions

In the context of the present application and invention, the following definitions apply: As used herein, the term "halogen" means fluorine, chlorine, bromine, or iodine. Fluorine, chlorine or bromine are preferred. Fluorine and chlorine are particularly preferred.

As used herein, "alkyl" used alone or as a suffix or prefix, is intended to include both branched and straight chain saturated aliphatic hydrocarbon groups of the specified number of carbon atoms. For example, "$C_{1-6}$alkyl" denotes alkyl having 1, 2, 3, 4, 5 or 6 carbon atoms. Examples of alkyl groups include, but are not limited to, methyl, ethyl, n-propyl, i-propyl, n-butyl, i-butyl, sec-butyl, t-butyl, pentyl, and hexyl.

As used herein, "alkylenyl" or "alkylene" used alone or as a suffix or prefix, is intended to include straight chain saturated aliphatic hydrocarbon groups of the specified number of carbon atoms. For example, "$C_{1-6}$alkylenyl" or "$C_{1-6}$alkylene" denotes alkylenyl or alkylene having 1, 2, 3, 4, 5 or 6 carbon atoms. When the specific number denoting the alkylenyl or alkylene group is the integer 0 (zero), a bond is intended to link the groups onto which the alkylenyl or alkylene group is substituted. For example, "—$C_0$alkyleneOH" is equivalent to "—OH" (hydroxyl). As used herein, the groups linked by an alkylene or alkylenyl group are intended to be attached to the first and to the last carbon of the alkylene or alkylenyl group. In the case of methylene, the first and the last carbon is the same. Examples of alkylene or alkylenyl include, but are not limited to, methylene, ethylene, propylene, butylene, pentylene, hexylene, heptylene and octylene.

As used herein, the term "aryl" means phenyl or naphthyl.

As used herein, the term "cycloalkyl" means a saturated group in a ring system of the specified number of carbon atoms. For example, "$C_{3-6}$cycloalkyl" denotes a cycloalkyl group having 3, 4, 5 or 6 carbon atoms. A cycloalkyl group can be monocyclic, spirocyclic or bicyclic. A cycloalkyl group may have a bridge in the cyclic structure. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bridged cycloalkyl groups include bicyclo[2.2.1]hept-2-yl and adamantanyl. Examples of spirocyclic cycloalkyl groups include spiro[5.5]undecanyl and spiro[5.4]decanyl. Preferably, the cycloalkyl group is monocyclic or spirocyclic and the monocyclic or spirocyclic cycloalkyl groups may optionally be bridged.

As used herein, the term "non-aromatic heterocyclyl" group or "non-aromatic heterocycle" group means a non-aromatic cyclic group of carbon atoms wherein from one to three of the carbon atoms is/are replaced by one or more heteroatoms independently selected from nitrogen, oxygen or sulfur. A non-aromatic heterocycle group may, for example, be monocyclic, spirocyclic, or bicyclic. A non-aromatic heterocycle group may, for example, have a bridge in the cyclic structure. In a bicyclic heterocyclyl group there may be one or more heteroatoms in each ring, or only in one of the rings. As mentioned above, the heteroatom(s) in the non-aromatic heterocycle may be selected from the group consisting of S, O and N and are preferably selected from the group consisting of O and N. Heterocyclyl groups containing a suitable nitrogen atom include the corresponding N-oxides. A non-aromatic heterocyclyl group may be partially saturated, i.e. contain one of more double bonds, but an insufficient number of bond to form a fully delocalized ring of electrons.

Examples of monocyclic non-aromatic heterocyclic groups (also referred to as monocyclic heterocycloalkyl rings) include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl.

Examples of bridged non-aromatic heterocyclyl groups include morphanyl and 1,4-diazabicyclo[2.2.2]octanyl.

Examples of spirocyclic non-aromatic heterocyclic groups include 1,4-dioxaspiro[4.5]decanyl, 6-azaspiro[3.3]heptanyl, 1,6-diazaspiro[3.3]heptanyl, 2-azaspiro[3.4]octanyl, 1,1-dimethylethyl ester and 1,4,6-triazaspiro[4.4]nonane.

As used herein, the term "heteroaryl" group means an aromatic cyclic group of carbon atoms wherein from one to three of the carbon atoms is/are replaced by one or more heteroatoms (for example 1, 2, 3, or 4; preferably 1, 2 or 3) independently selected from nitrogen, oxygen or sulfur. A heteroaryl group may, for example, be monocyclic or bicyclic. In a bicyclic heteroaryl group there may be one or more heteroatoms in each ring, or only in one of the rings. In a bicyclic heteroaryl group both rings may be aromatic, or only one of the rings. As mentioned above, the heteroatom(s) in the heteroaryl may be selected from the group consisting of S, O and N, and are preferably selected from the group consisting of N and S.

Examples of monocyclic aromatic heterocyclyl groups (also referred to as monocyclic heteroaryl groups) include furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl and pyrimidinyl groups.

Examples of bicyclic heterocyclyl groups in which one of the rings is non-aromatic include dihydrobenzofuranyl, indanyl, indolinyl, isoindolinyl, tetrahydroisoquinolinyl, tetrahydroquinolyl and benzoazepanyl groups.

Examples of bicyclic aromatic heterocyclyl groups (also referred to as bicyclic heteroaryl groups) include quinoxalinyl, quinazolinyl, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridiyl, pyridopyrimidinyl, isoquinolinyl and benzodroxazolyl groups Preferred examples of heteroaryl groups of the present invention include pyridyl (i.e., pyridinyl), pyrimidinyl, pyrazinyl, pyridazinyl, triazinyl, quinolyl, tetrahydroquinolyl, isoquinolyl, tetrahydroisoquinolyl, imidazolyl, thiazolyl, indolyl, pyrryl, oxazolyl, benzthiazolyl, isoxazolyl, pyrazolyl, triazolyl, indazolyl, 1,2,4-thiadiazolyl, isothiazolyl, benzimidazolyl, indolinyl, and the like.

As mentioned above, the compounds of the invention have activity as inhibitors for GCN2, and are inhibitors of GCN2. As such, the invention also provides a compound of the invention, or a composition comprising a compound of the invention, for use as a medicament, or for use in therapy. For example, the invention provides a compound of the invention, or a composition comprising a compound of the invention, together with a pharmaceutically acceptable carrier, for use as a medicament, or for use in therapy.

For the avoidance of doubt, as used herein the terms "therapy", "treatment" and "treating" include both preventative and curative treatment of a condition, disease or disorder. It also includes slowing, interrupting, controlling or stopping the progression of a condition, disease or disorder. It also includes preventing, curing, slowing, interrupting, controlling or stopping the symptoms of a condition, disease or disorder. For example, it includes preventing the metastasis of cancer wherein the disease or disorder is cancer.

A compound of the invention, or a composition comprising a compound of the invention, may be used in the treatment of a disease or disorder in which the inhibition of GCN2 provides a therapeutic effect. As such, the compounds of the invention may be used in the treatment or prophylaxis of diseases or disorders for which inhibitors of GCN2 are indicated.

The compounds of the invention find particular application in the treatment or prophylaxis of a disease or disorder in which the inhibition of GCN2 provides a therapeutic effect, for example a disease or disorder selected from the group consisting of: cancer (for example solid cancers and hematological cancers).

The invention also provides a method of treating a subject suffering from a medical disorder or disease. The method comprises administering to the subject a therapeutically effective amount of a compound of the invention or a composition as described herein, to treat the disorder or disease. As mentioned above, a number of diseases or disorders in which the inhibition of GCN2 provides a therapeutic effect can be treated using the compounds of the invention. For example, the compounds described herein can be used to treat cancer (for example solid cancers and hematological cancers).

When a compound of the invention, or a composition comprising a compound of the invention, is used in therapy as a medicament for the treatment or prophylaxis of a disease or disorder, for example in the therapeutic uses and methods described herein, the use or method may comprise the step of administering, to a mammal, including a human, in need of such treatment or prophylaxis, a therapeutically effective amount of a compound of the invention.

The compounds of the invention find particular application in the treatment or prophylaxis of cancer. In certain embodiments, the cancer is a solid tumor or a hematological cancer (for example leukemia or multiple myeloma). In certain embodiments, the cancer is a cancer with a MYC mutation.

Examples of cancers that the compounds of the invention find particular application in the treatment or prophylaxis of include, but are not limited to: colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer, castration-resistant prostate cancer), liver cancer (e.g., hepatoma, primary liver cancer, extrahepatic bile duct cancer), thyroid cancer (e.g., medullary thyroid carcinoma), renal cancer (e.g., renal cell carcinoma (e.g., clear cell renal cell carcinoma), transitional cell carcinoma of renal pelvis and ureter), uterine cancer (e.g., cervixcancer, uterine body cancer, uterus sarcoma), gestational choriocarcinoma, brain tumor (e.g., medulloblastoma, glioma, glioblastoma, pineal astrocytoma, pilocytic astrocytoma, diffuse astrocytoma, anaplastic astrocytoma, hypophyseal adenoma), retina blastoma, skin cancer (e.g., basal cell carcinoma, malignant melanoma (melanoma)), sarcoma (e.g., rhabdomyosarcoma, leiomyosarcoma, soft tissue sarcoma, spindle cell sarcoma, osteosarcoma), malignant bone tumor, urinary bladder cancer, and hematologic cancer (e.g., multiple myeloma, smouldering myeloma, plasmacytoma, leukemia (e.g., acute myeloid leukemia, acute lymphocytic leukemia (including blast crisis of chronic leukemia)), non-Hodgkin's lymphoma, malignant lymphoma, Hodgkin's disease, chronic myeloproliferative disease), and cancer of unknown primary nucleus).

The compounds of the invention also find application as cancer growth inhibitors, cancer metastasis inhibitors, apoptosis promoters, and for the prophylaxis or treatment of precancerous lesions (e.g., bone marrow myelodysplastic syndrome, monoclonal gammopathy of undetermined significance).

In one embodiment, the compounds of the invention find particular application in the treatment or prophylaxis of osteosarcoma, acute myeloid leukemia, acute lymphocytic leukemia, multiple myeloma, pancreatic cancer, colorectal cancer, melanoma, and malignant lymphoma.

Examples of solid cancers that the compounds of the invention find particular application in the treatment or prophylaxis of include, but are not limited to: colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer, castration-resistant prostate cancer), liver cancer (e.g., hepatoma, primary liver cancer, extrahepatic bile duct cancer), thyroid cancer (e.g., medullary thyroid carcinoma), renal cancer (e.g., renal cell carcinoma (e.g., clear cell renal cell carcinoma), transitional cell carcinoma of renal pelvis and ureter), uterine cancer (e.g., cervixcancer, uterine body cancer, uterus sarcoma), gestational choriocarcinoma, brain tumor (e.g., medulloblastoma, glioma, glioblastoma, pineal astrocytoma, pilocytic astrocytoma, diffuse astrocytoma, anaplastic astrocytoma, hypophyseal adenoma), retina blastoma, skin cancer (e.g., basal cell carcinoma, malignant melanoma (melanoma)), sarcoma (e.g., rhabdomyosarcoma, leiomyosarcoma, soft tissue sarcoma, spindle cell sarcoma, osteosarcoma), malignant bone tumor, and urinary bladder cancer.

Examples of hematological cancers that the compounds of the invention find particular application in the treatment or prophylaxis of include, but are not limited to: multiple myeloma, smouldering myeloma, plasmacytoma, leukemia (e.g., acute myeloid leukemia, acute lymphocytic leukemia (including blast crisis of chronic leukemia)), non-Hodgkin's lymphoma, malignant lymphoma, Hodgkin's disease, and chronic myeloproliferative disease.

In one embodiment, the compounds of the invention find particular application in the treatment or prophylaxis of a cancer with high levels of MYC (i.e. a cancer in which the MYC gene or protein are expressed at high levels). Examples of cancers having a MYC mutation that the compounds of the invention find particular application in the treatment or prophylaxis of include, but are not limited to: prostate cancer, breast cancer (for example triple negative breast cancer), lung cancer (for example small cell lung cancer), ovarian cancer, neuroblastomas and leukemia (for example acute lymphoblastic leukemia and mixed-lineage leukemia).

The compounds of the invention also find application in conditions selected from: diabetic retinopathy, myocardial ischemia, diabetic cardiomyopathy, allergic airway inflammation, doxorubicin-induced cardiotoxicity and nonalcoholic fatty liver disease (NAFLD).

The invention also provides a method for the treatment or prophylaxis of a disease or disorder in which the inhibition of GCN2 provides a therapeutic effect in a mammal, which comprises administering to the mammal a therapeutically effective amount of a compound according to the invention, or a composition comprising a compound according to the invention. Diseases and disorders that may be treated by this method of the invention are preferably those described above.

The invention also provides the use of a compound according to the invention, for the manufacture of a medicament for the treatment or prophylaxis of a disease or disorder in which the inhibition of GCN2 provides a therapeutic effect. Diseases and disorders that may be treated by this use of the invention are preferably those described above.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the invention may be administered in a single daily dose, or the total daily dosage may be administered in divided doses of two, three or four times daily. Furthermore, compounds for the invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

While it is possible for the active ingredient to be administered alone, it is preferable for it to be present in a pharmaceutical formulation or composition. Accordingly, the invention provides a pharmaceutical formulation or composition comprising a compound according to the invention, and a pharmaceutically acceptable diluent, excipient or carrier (collectively referred to herein as "carrier" materials). Pharmaceutical compositions and formulations of the invention may take the form of a pharmaceutical composition or formulation as described below.

Pharmaceutical compositions according to the invention include those suitable for oral, parenteral (including subcutaneous, intradermal, intramuscular, intravenous [bolus or infusion], and intraarticular), inhalation (including fine particle dusts or mists which may be generated by means of various types of metered dose pressurized aerosols), nebulizers or insufflators, rectal, intraperitoneal and topical (including dermal, buccal, sublingual, and intraocular) administration, although the most suitable route may depend upon, for example, the condition and disorder of the recipient.

The compositions may conveniently be presented in unit dosage form and may be prepared by any of the methods well known in the art of pharmacy. All methods include the step of bringing the active ingredient into association with the carrier, which constitutes one or more accessory ingredients. In general, the compositions are prepared by uniformly and intimately bringing into association the active ingredient with liquid carriers or finely divided solid carriers or both and then, if necessary, shaping the product into the desired composition.

Compositions of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so to provide slow or controlled release of the active ingredient therein. The compounds of the invention can, for example, be administered in a form suitable for immediate release or extended release. Immediate release or extended release can be achieved by the use of suitable pharmaceutical compositions comprising a compound of the present invention, or, particularly in the case of extended release, by the use of devices such as subcutaneous implants or osmotic pumps.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of the invention can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such compositions may be high molecular weight excipients such as celluloses (avicel) or polyethylene glycols (PEG). Such compositions can also include an excipient to aid mucosal adhesion such as hydroxypropyl cellulose (HPC), hydroxypropyl methylcellulose (HPMC), sodium carboxymethyl cellulose (SCMC), maleic anhydride copolymer (e.g. Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidykholine (lecithin).

Compositions for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor®.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Compositions for rectal administration may be presented as a suppository with the usual carriers such as cocoa butter, synthetic glyceride esters or polyethylene glycol. Such carriers are typically solid at ordinary temperatures but liquefy and/or dissolve in the rectal cavity to release the drug.

Compositions for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase® (mineral oil gelled with polyethylene).

Preferred unit dosage compositions are those containing an effective dose, as hereinbefore recited, or an appropriate fraction thereof, of the active ingredient.

It should be understood that in addition to the ingredients particularly mentioned above, the compositions of this invention may include other agents conventional in the art having regard to the type of composition in question, for example, those suitable for oral administration may include flavouring agents.

Whilst a compound of the invention may be used as the sole active ingredient in a medicament, it is also possible for the compound to be used in combination with one or more further therapeutic agents. Thus, the invention also provides a compound according to the invention together with a further therapeutic agent, for simultaneous, sequential or separate administration. Such further therapeutic agents may be further compounds according to the invention, or they may be different therapeutic agents, for example another GCN2 inhibitor. The further therapeutic agent may also be a therapeutic agent for use in the treatment or prophylaxis of a disease or disorder in which the inhibition of GCN2 provides a therapeutic effect, for example a disease or disorder selected from the group consisting of cancer (for example solid cancers and hematological cancers), and autoimmune diseases, and in particular cancer.

Therefore, in one embodiment, the further therapeutic agent may be a different therapeutic agent for use in the treatment or prophylaxis of cancer, for example it may be a chemotherapeutic agent selected from the group consisting of L-asparaginase (ASNase), a proteasome inhibitor (for example bortezomib, carfilzomib, ixazomib, or marizomib), immunomodulatory drugs (for example, thalidomide, lenalidomide and pomalidomide), SINE compounds (for example selinexor), monocolonal antibodies (for example, such as rituximab, daratumumab, isatuximab, herceptin and avastin), alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, antimetabolites, erlotinib, vemurafenib, crizotinib, sorafenib, ibrutinib, enzalutamide, folic acid analogues, purine analogs, androgens, anti-adrenals, folic acid replenisher such as folinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid 2-ethylhydrazide, procarbazine, PSK® polysaccharide complex (JHS Natural Products, Eugene, OR), razoxane, rhizoxin, sizofiran, spirogermanium, tenuazonic acid, triaziquone; 2,2',2"-trichlorotriethylamine, trichothecenes (especially T-2 toxin, verracurin A, roridin A and anguidine), urethan, vindesine, dacarbazine, mannomustine, mitobronitol, mitolactol, pipobroman, gacytosine, arabinoside ("Ara-C"), cyclophosphamide, thiotepa, taxoids, chloranbucil, gemcitabine, 6-thioguanine, mercaptopurine, methotrexate, platinum analogs, vinblastine, platinum, etoposide (VP-16), ifosfamide, mitoxantrone, vincristine, vinorelbine, novantrone, teniposide, edatrexate, daunomycin, aminopterin, xeloda, ibandronate, irinotecan (Camptosar, CPT-11), topoisomerase inhibitor RFS 2000, difluorometlhylornithine, asparaginase, retinoids, capecitabine, combretastatin, leucovorin, oxaliplatin, inhibitors of PKC-alpha, Raf, H-Ras, EGFR and VEGF-A that reduce cell proliferation, and pharmaceutically acceptable salts, acids or derivatives thereof, and combinations thereof.

In another embodiment, the further therapeutic agent may be a checkpoint inhibitor, for example an agent or antibody that inhibits one or more of CTLA4, PD-1, PD-L1, LAG-3, B7-H3, B7-H4, TIM3, VISTA and KIR.

In certain embodiments the compound of the invention is administered in combination with L-asparaginase (ASNase). Such a combination treatment may be used for the treatment of cancer, and in particular for the treatment of a acute lymphocytic leukemia (including blast crisis of chronic leukemia) and non-Hodgkin's lymphoma. Such a combination treatment may also be used for the treatment of cancer tumor resistant or tolerant to asparaginase, for example a cancer selected from the group consisting of acute lymphocytic leukemia (including blast crisis of chronic leukemia) and non-Hodgkin's lymphoma.

In certain embodiments the compound of the invention is administered in combination with a proteasome inhibitor, for example bortezomib, carfilzomib, ixazomib, marozomib or oprozomib. Such a combination treatment may be used for the treatment of cancer, and in particular for the treatment of a hematological cancer, for example Hodgkin's lymphoma, multiple myeloma, smouldering myeloma, and the premalignant condition, monoclonal gammopathy of undetermined significance.

In embodiments where the compounds of the invention are used in combination with other agent(s) for use in the treatment or prophylaxis of a disease or disorder in which the inhibition of GCN2 provides a therapeutic effect, the individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the compounds of this invention with other agents for use in the treatment or prophylaxis of a disease or disorder in which the inhibition of GCN2 provides a therapeutic effect includes in principle any combination with any pharmaceutical composition useful for treating a disease or disorder in which the inhibition of GCN2 provides a therapeutic effect.

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the invention as described above also find use in combination with radiation therapy for the treatment of cancer.

Furthermore, the compound of the present invention may be used in combination with a non-drug therapy. Specifically, the compound of the present invention or the combination agent of the present invention can be used in combination with, for example, a non-drug therapy such as (1) operation, (2) hypertensive chemical therapy using angiotensin II and the like, 30 (3) gene therapy, (4) hyperthermic therapy, (5) cryotherapy; (6) laser ablation method; (7) radiation therapy; (8) diet therapy (e.g., amino acid restriction diet) and the like.

For example, using the compound of the present invention or the combination agent of the present invention before or after the aforementioned surgery and the like, or before or after the treatment of two or three kinds of these in combination, effects such as inhibition of expression of resistance, prolongation of disease-free survival, suppression of cancer metastasis or recurrence, prolongation of life and the like can be achieved.

In addition, the treatment with the compound of the present invention or the combination agent of the present invention can be combined with a supporting therapy, for example (i) administration of antibiotics (for example, P-lactam system such as pansporin and the like, macrolide system such as clarithromycin and the like) for complications of various infectious diseases, (ii) administration of intravenous hyperalimentation, amino acid preparation, multiple vitamin preparation for improving malnutrition, (iii) morphine administration for pain relief, (iv) administration of medicament for improving side effects such as nausea, vomiting, anorexia, diarrhea, leucopenia, thrombocytopenia, hemoglobin concentration reduction, hair loss, hepatopathy, renopathy, DIC, fever and the like and (v) administration of medicament for suppressing multiple drug resistance of cancer and the like.

The compounds of the invention as described above also find use, optionally in labelled form, as a diagnostic agent for the diagnosis of conditions associated with a disease or disorder in which the inhibition of GCN2 provides a therapeutic effect. For example, such a compound may be radioactively labelled.

In addition to their use in therapeutic medicine, compounds according to the invention may also be useful as pharmacological tools in the development and standardization of in vitro and in vivo test systems for the evaluation of other compounds with similar activity. Furthermore, compounds of the invention may be used as molecular probes to identify and/or locate the target of their action, such as a target within the airways, as well as employed as a diagnostic tool for diagnosis of a disease or condition in vivo, ex vivo or in vitro, or as synthetic precursors to such probes. Molecular probes of the invention may include reactive, labeled (i.e. compounds of the invention wherein one or several of the composing atoms have been enriched with a radioactive or by other means detectable isotope), and fluorescent compounds as well known to the one skilled in the art.

The following Examples illustrate the invention.

List of Abbreviations anh.—anhydrous
ACN—acetonitrile
Boc—tert-butoxycarbonyl
$CDCl_3$—deuterated chloroform CD$_3$OD—deuterated methanol
DCM—dichloromethane
DIPEA—N,N-diisopropylethylamine
DMAP—4-dimethylaminopyridine
DMSO—dimethylsulfoxide
DMSO-d$_6$—deuterated dimethylsulfoxide
EA—ethyl acetate
eq. or Equiv—equivalent
FC—flash chromatography
$^1$H NMR—proton nuclear magnetic resonance
HPLC—high performance liquid chromatography
MeOH—methanol
MS—mass spectrometry
NCS—N-chlorosuccinimide
r.t.—room temperature
RT—retention time
sat.—saturated
TEA—triethylamine
THF—tetrahydrofuran
TMS—trimethylsilyl
Y—yield Analytical Methods Description:
All $^1$H NMR spectra were measured on Bruker Avance III HD 400 MHz or Bruker Fourier 300 MHz NMR spectrometer, exchangeable protons may or may not be observed LCMS (Method A)
   Apparatus: Dionex UHPLC Ultimate 3000 with DAD detector/Thermo Scientific MSQ Plus
   Column: Kinetex® 2.6 μm XB-C18 (4.6×50 mm), 110 A, column no. 008-4496-E0.
   Reagents:
      Formic acid≥98%, Sigma-Aldrich
      Acetonitrile for HPLC UV/gradient grade, Baker
      μQ-water for LCMS
   HPLC Conditions:
      Wavelength range: (190-340) nm±4 nm
      Flow: 1.0 ml/min
      Column temperature: 25° C.
      Autosampler temperature: 20° C.
      Analysis time: 6 min
      Elution: gradient

| Time [min] | Mobile phase A [%] | Mobile phase B [%] | Flow [ml/min] |
|---|---|---|---|
| 0.0 | 70 | 30 | 1.0 |
| 3.35 | 45 | 55 | 1.0 |
| 3.75 | 45 | 55 | 1.0 |
| 3.90 | 5 | 95 | 1.0 |
| 4.75 | 5 | 95 | 1.0 |
| 5.00 | 70 | 30 | 1.0 |
| 6.00 | 70 | 30 | 1.0 |

Mobile phase A: 0.1% v/v water solution of formic acid
Mobile phase B: 0.1% v/v acetonitrile solution of formic acid
Solution for syringe washing: 20% MeOH
MS Conditions:
   Mass range: 100-1000 m/z
   Ionization: alternate
   Scan speed: 12 000 amu/sec LCMS (Method B):
   Apparatus: Dionex UHPLC Ultimate 3000 with DAD detector/Thermo Scientific MSQ Plus
   Column: Kinetex® 2.6 μm XB-C18 (4.6×50 mm), 110 A, column no. 00B-4496-E0.
   Reagents:
      Formic acid≥98%, Sigma-Aldrich
      Acetonitrile for HPLC UV/gradient grade, Baker
      μQ-water for LCMS
   HPLC Conditions:
      Wavelength range: (190-340) nm±4 nm
      Flow: 1.0 ml/min
      Column temperature: 25° C.
      Autosampler temperature: 20° C.
      Injection volume: 2.0 μl
      Analysis time: 6 min
      Elution: gradient

| Time [min] | Mobile phase A [%] | Mobile phase B [%] | Flow [ml/min] |
|---|---|---|---|
| 0.0 | 70 | 30 | 1.0 |
| 3.35 | 20 | 80 | 1.0 |
| 3.75 | 20 | 80 | 1.0 |
| 3.90 | 5 | 95 | 1.0 |
| 4.75 | 5 | 95 | 1.0 |
| 5.00 | 70 | 30 | 1.0 |
| 6.00 | 70 | 30 | 1.0 |

Mobile phase A: 0.1% v/v water solution of formic acid
Mobile phase B: 0.1% v/v acetonitrile solution of formic acid
Solution for syringe washing: 20% MeOH
MS Conditions:
   Mass range: 100-1000 m/z
   Ionization: alternate
   Scan speed: 12 000 amu/sec LCMS (Method C):
   Apparatus: Dionex UHPLC Ultimate 3000 with DAD detector/Thermo Scientific MSQ Plus
   Column: Kinetex® 2.6 μm XB-C18 (4.6×50 mm), 110 A, column no. 00B-4496-E0.
   Reagents:
      Formic acid≥98%, Sigma-Aldrich
      Acetonitrile for HPLC UV/gradient grade, Baker
      μQ-water for LCMS
   HPLC Conditions:
      Wavelength range: (190-340) nm±4 nm
      Flow: 1.0 ml/min
      Column temperature: 25° C.
      Autosampler temperature: 20° C.
      Injection volume: 2.0 μl
      Analysis time: 6 min
      Elution: gradient

| Time [min] | Mobile phase A [%] | Mobile phase B [%] | Flow [ml/min] |
|---|---|---|---|
| 0.0 | 80 | 20 | 1.0 |
| 3.35 | 20 | 80 | 1.0 |
| 3.75 | 20 | 80 | 1.0 |
| 3.90 | 5 | 95 | 1.0 |
| 4.75 | 5 | 95 | 1.0 |
| 5.00 | 80 | 20 | 1.0 |
| 6.00 | 80 | 20 | 1.0 |

Mobile phase A: 0.1% v/v water solution of formic acid
Mobile phase B: 0.1% v/v acetonitrile solution of formic acid
Solution for syringe washing: 20% MeOH MS Conditions:
  Mass range: 100-1000 m/z
  Ionization: alternate
  Scan speed: 12 000 amu/sec
LCMS (Method D):
  Apparatus: Dionex UHPLC Ultimate 3000 with DAD detector/Thermo Scientific MSQ Plus
  Column: Kinetex® 2.6 μm XB-C18 (4.6×50 mm), 110 A, column no. 00B-4496-E0.
  Reagents:
    Formic acid≥98%, Sigma-Aldrich
    Acetonitrile for HPLC UV/gradient grade, Baker
    μQ-water for LCMS
  HPLC Conditions:
    Wavelength range: (190-340) nm±4 nm
    Flow: 1.0 ml/min
    Column temperature: 25° C.
    Autosampler temperature: 20° C.
    Injection volume: 2.0 μl
    Analysis time: 6 min
    Elution: gradient

| Time [min] | Mobile phase A [%] | Mobile phase B [%] | Flow [ml/min] |
| --- | --- | --- | --- |
| 0.0 | 60 | 40 | 1.0 |
| 3.35 | 20 | 80 | 1.0 |
| 3.75 | 20 | 80 | 1.0 |
| 3.90 | 5 | 95 | 1.0 |
| 4.75 | 5 | 95 | 1.0 |
| 5.00 | 60 | 40 | 1.0 |
| 6.00 | 60 | 40 | 1.0 |

Mobile phase A: 0.1% v/v water solution of formic acid
Mobile phase B: 0.1% v/v acetonitrile solution of formic acid
Solution for syringe washing: 20% MeOH
MS Conditions:
  Mass range: 100-1000 m/z
  Ionization: alternate
  Scan speed: 12 000 amu/sec
LCMS (Method E)
  Apparatus: Dionex UHPLC Ultimate 3000 with DAD detector/Thermo Scientific MSQ Plus
  Column: Kinetex® 2.6 μm XB-C18 (4.6×50 mm), 110 A, column no. 00B-4496-E0, internal column no. 019
  Reagents:
    Formic acid≥98%, Sigma-Aldrich
    Acetonitrile for HPLC UV/gradient grade, Baker
    μQ-water for LCMS
  HPLC Conditions:
    Wavelength range: (190-340) nm±4 nm
    Flow: 1.0 ml/min
    Column temperature: 25° C.
    Autosampler temperature: 20° C.
    Analysis time: 6 min
    Elution: gradient

| Time [min] | Mobile phase A [%] | Mobile phase B [%] | Flow [ml/min] |
| --- | --- | --- | --- |
| 0.0 | 70 | 30 | 1.0 |
| 3.35 | 40 | 60 | 1.0 |
| 3.75 | 40 | 60 | 1.0 |
| 3.90 | 5 | 95 | 1.0 |
| 4.75 | 5 | 95 | 1.0 |
| 5.00 | 70 | 30 | 1.0 |
| 6.00 | 70 | 30 | 1.0 |

Mobile phase A: 0.1% v/v water solution of formic acid
Mobile phase B: 0.1% v/v acetonitrile solution of formic acid
Solution for syringe washing: 20% MeOH
MS Conditions:
  Mass range: 100-1000 m/z
  Ionization: alternate
  Scan speed: 12 000 amu/sec
LCMS (Method F)
  Apparatus: Dionex UHPLC Ultimate 3000 with DAD detector/Thermo Scientific ISQ EC-Mass Spectrometer
  Column: Kinetex® 2.6 μm XB-C18 (4.6×50 mm), 110 A, column no. 00B-4496-E0, internal column no. 036
  Reagents:
    Ammonium Hydroxide solution 28-30%, Sigma-Aldrich
    Acetonitrile for HPLC UV/gradient grade, Baker
    μQ-water for LCMS
  HPLC Conditions:
    Wavelength range: (190-350) nm±4 nm
    Flow: 1.0 ml/min
    Column temperature: 25° C.
    Autosampler temperature: 20° C.
    Analysis time: 6 min
    Elution: gradient

| Time [min] | Mobile phase A [%] | Mobile phase B [%] | Flow [ml/min] |
| --- | --- | --- | --- |
| 0.00 | 80 | 20 | 1.0 |
| 3.35 | 40 | 60 | 1.0 |
| 3.75 | 40 | 60 | 1.0 |
| 3.90 | 5 | 95 | 1.0 |
| 4.75 | 5 | 95 | 1.0 |
| 5.00 | 80 | 20 | 1.0 |
| 6.00 | 80 | 20 | 1.0 |

Mobile phase C: 0.05% water solution of ammonium hydroxide (28.0-30.0% NH$_3$ basis)
Mobile phase D: acetonitrile
Solution for syringe washing: 20% MeOH
MS Conditions:
  Mass range: 100-1000 m/z
  Ionization: alternate
  Scan speed: 12 000 amu/sec
LCMS (Method 6)
  Apparatus: Dionex UHPLC Ultimate 3000 with DAD detector/Thermo Scientific ISQ EC-Mass Spectrometer
  Column: Kinetex® 2.6 μm XB-C18 (4.6×50 mm), 110 A, column no. 00B-4496-E0, internal column no. 036
  Reagents:
    Ammonium Hydroxide solution 28-30%, Sigma-Aldrich
    Acetonitrile for HPLC UV/gradient grade, Baker
    μQ-water for LCMS HPLC Conditions:
  Wavelength range: (190-350) nm±4 nm
  Flow: 1.0 ml/min
  Column temperature: 25° C.
  Autosampler temperature: 20° C.
  Analysis time: 6 min
  Elution: gradient

| Time [min] | Mobile phase A [%] | Mobile phase B [%] | Flow [ml/min] |
|---|---|---|---|
| 0.00 | 90 | 10 | 1.0 |
| 3.35 | 60 | 40 | 1.0 |
| 3.75 | 60 | 40 | 1.0 |
| 3.90 | 5 | 95 | 1.0 |
| 4.75 | 5 | 95 | 1.0 |
| 5.00 | 90 | 10 | 1.0 |
| 6.00 | 90 | 10 | 1.0 |

Mobile phase C: 0.05% water solution of ammonium hydroxide (28.0-30.0% NH$_3$ basis)
Mobile phase D: acetonitrile
Solution for syringe washing: 20% MeOH
MS Conditions:
  Mass range: 100-1000 m/z
  Ionization: alternate
  Scan speed: 12 000 amu/sec
LCMS (Method H)
  Apparatus: Dionex UHPLC Ultimate 3000 with DAD detector/Thermo Scientific MSQ Plus
  Column: Kinetex® 2.6 μm XB-C18 (4.6×50 mm), 110 A, column no. 00B4496-E0, internal column no. 019
  Reagents:
    Formic acid≥98%, Sigma-Aldrich
    Acetonitrile for HPLC UV/gradient grade, Baker
    μQ-water for LCMS
  HPLC Conditions:
    Wavelength range: (190-340) nm±4 nm
    Flow: 1.0 ml/min
    Column temperature: 25° C.
    Autosampler temperature: 20° C.
    Injection volume: 2.0 μl
    Analysis time: 6 min
    Elution: gradient

| Time [min] | Mobile phase A [%] | Mobile phase B [%] | Flow [ml/min] |
|---|---|---|---|
| 0.00 | 60 | 40 | 1.0 |
| 3.35 | 40 | 60 | 1.0 |
| 3.75 | 40 | 60 | 1.0 |
| 3.90 | 5 | 95 | 1.0 |
| 4.75 | 5 | 95 | 1.0 |
| 5.00 | 60 | 40 | 1.0 |
| 6.00 | 60 | 40 | 1.0 |

Mobile phase A: 0.1% v/v water solution of formic acid
Mobile phase B: 0.1% v/v acetonitrile solution of formic acid
Solution for syringe washing: 20% MeOH
MS Conditions:
  Mass range: 100-1000 m/z
  Ionization: alternate
  Scan speed: 12 000 amu/sec Example 1: N-{4-[2-(2-aminopyrimidin-5-yl)ethynyl]-3-fluoropyridin-2-yl}-5-chloro-2-methoxypyridine-3-sulfonamide

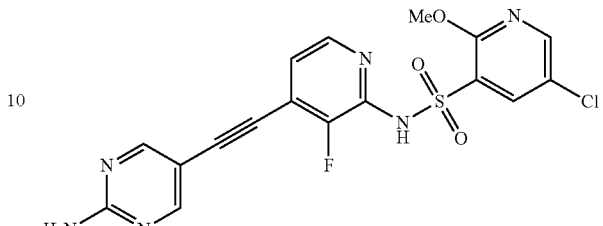

Step 1: tert-butyl N-(5-bromopyrimidin-2-yl)-N-[(tert-butoxy)carbonyl]carbamate

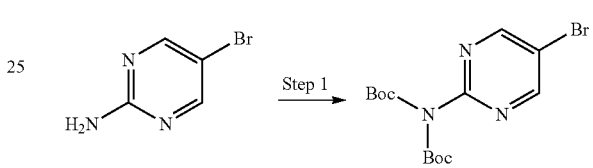

To a stirred solution of 2-amino-5-bromopyrimidine (5.1 g, 0.029 mol, 1 eq.) and DMAP (0.72 g, 0.006 mol, 0.2 eq.) in anh. THF (204 ml) was added di-tert-butyl dicarbonate (15.99 g, 0.073 mol, 2.5 eq.). The mixture was stirred at r.t. overnight and quenched with water (150 ml). The resulting mixture was extracted with EA (3×100 ml). Combined organic layers were washed with water (100 ml) and brine (100 ml), dried over Na$_2$SO$_4$, filtered and evaporated to obtain a crude product (11.62 g) as a brown solid, which was used for the next step without purification.

$^1$H NMR (300 MHz, CDCl$_3$) δ: 8.80 (s, 2H), 1.49 (s, 18H)
MS m/z: [M+H]$^+$ 373.85

Step 2: tert-butyl N-[(tert-butoxy)carbonyl]-N-{5-[2-(trimethylsilyl)ethynyl]pyrimidin-2-yl}carbamate

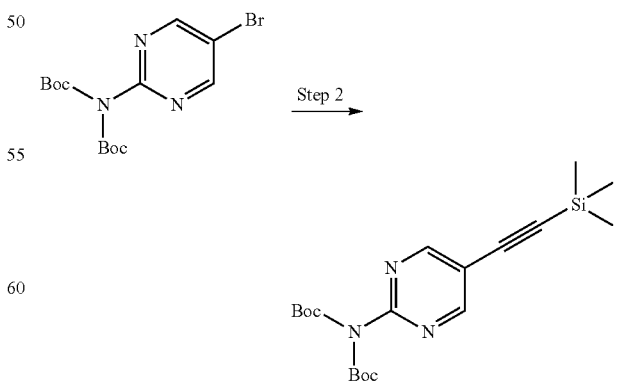

To a stirred solution of crude tert-butyl N-(5-bromopyrimidin-2-yl)-N-[(tert-butoxy)carbonyl]carbamate (Step 1, 11.62 g, 0.031 mol, 1 eq.) in ACN (140 ml) in a glass pressure reactor was added TMS acetylene (13.26 ml, 9.15 g, 0.093 mol, 3 eq.), copper (I) iodide (1.18 g, 0.006 mol, 0.2 eq.) and TEA (13 ml, 9.43 g, 0.093 mol, 3 eq.). Argon was bubbled through the mixture for 15 minutes and $PdCl_2$ $(PPh_3)_2$ (2.18 g, 0.003 mol, 0.1 eq.) was added. The reactor was sealed and the mixture was stirred at 80° C. overnight. The mixture was filtered through a pad of Celite and volatiles were evaporated under reduced pressure. The residue was dissolved in EA (200 ml) and washed with water (100 ml). Phases were separated, the aqueous phase was extracted with EA (100 ml). Celite pad was additionally washed with EA (4×100 ml). Combined organic phases were dried over $Na_2SO_4$, filtered and evaporated to give a crude product (16.7 g) as a brown solid, which was used further without purification.

$^1$H NMR (300 MHz, $CDCl_3$) δ: 8.78 (s, 2H), 1.47 (s, 18H), 0.30 (s, 9H)

MS m/z: [M+H]$^+$ 392.10

Step 3: tert-butyl
N-(5-ethynylpyrimidin-2-yl)carbamate

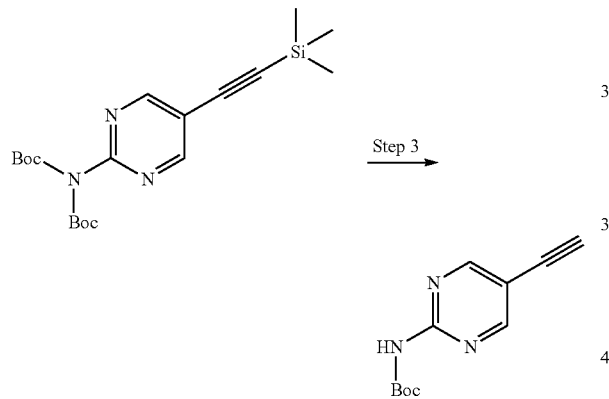

To a solution of crude tert-butyl N-[(tert-butoxy)carbonyl]-N-{5-[2-(trimethylsilyl)ethynyl]pyrimidin-2-yl}carbamate (Step 2, 14.0 g, 0.036 mol, 1 eq.) in anh. MeOH (210 ml) was added $K_2CO_3$ (14.82 g, 0.107 mol, 3 eq.). The mixture was stirred at r.t. for 1 hour. The reaction mixture was diluted with EA (300 ml) and concentrated under reduced pressure. Purification of the residue by FC ($SiO_2$, hexane/EA 100:0-0:100) afforded the product (1.48 g, Y: 23% over 3 steps) as a tan solid.

$^1$H NMR (300 MHz, $CDCl_3$) δ: 8.71 (s, 2H), 8.20 (s, 1H), 3.31 (s, 1H), 1.58 (s, 9H)

MS m/z: [M+H]$^+$ 219.95

Step 4:
3-(benzylsulfanyl)-5-chloro-2-methoxypyridine

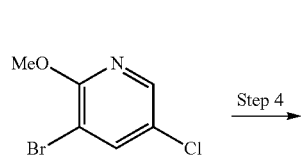

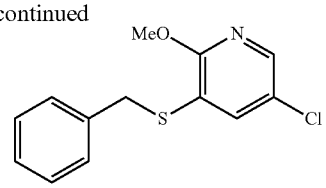

5-chloro-2-methoxy-3-bromopyridine (8.0 g, 35 mmol, 1 eq.), benzyl mercaptan (8.5 ml, 71 mmol, 2 eq.) and DIPEA (15.7 ml, 89 mmol, 2.5 eq.) were dissolved in dioxane (160 ml). After degassing with argon for 10 min, Xantphos (4.2 g, 7.1 mmol, 0.2 eq.) and $Pd_2(dba)_3$ (3.29 g, 3.6 mmol, 0.1 eq.) were added and the resulting mixture was heated at 100° C. overnight. Afterward, insolubilities were filtered off, the solvent was evaporated in vacuo and the residue was diluted with EA and washed with water. The organic phase was dried with $MgSO_4$, filtered and evaporated under reduced pressure. The crude product was purified by FC ($SiO_2$, 5% EA in hexane) affording the crystalline product (6.1 g, Y: 62%).

$^1$H NMR (300 MHz, $CDCl_3$) δ: 7.91 (d, J=2.4 Hz, 1H), 7.40 (d, J=2.4 Hz, 1H), 7.36-7.27 (m, 5H), 4.13 (s, 2H), 4.02 (s, 3H)

MS m/z: [M+H]$^+$ 265.90

Step 5: 5-chloro-2-methoxypyridine-3-sulfonyl
chloride

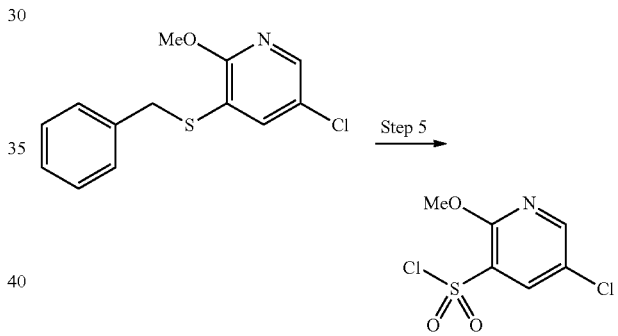

NCS (15 g, 112 mmol, 6 eq.) was added slowly for 30 min. to a pre-cooled (5° C.) solution of 3-(benzylsulfanyl)-5-chloro-2-methoxypyridine (Step 4, 5 g, 18.8 mmol, 1 eq.) in water (20 ml) and acetic acid (40 ml). The mixture was stirred 2 h at 5-10° C. and 1 h at room temperature. Afterward, the mixture was diluted with water, ethyl acetate was added and basified with sodium bicarbonate to pH=7. The organic layer was washed with brine, dried over magnesium sulfate and concentrated to give a crude residue. The product was extracted with warm hexane, filtered off from chilled solution to give the title product (3.64 g, Y: 73.1%).

$^1$H NMR (300 MHz, $CDCl_3$) δ: 8.45 (d, J=2.5 Hz, 1H), 8.24 (d, J=2.5 Hz, 1H), 4.21 (s, 3H)

Step 6: 3-fluoro-4-iodopyridin-2-amine

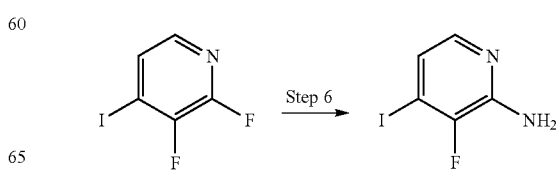

2,3-Difluoro-4-iodopyridine (1.14 g, 4.74 mmol, 1 eq.) and acetamidine hydrochloride (0.538 g, 5.69 mmol, 1.2 eq.) were combined and an aqueous solution of NaOH (0.474 g, 11.9 mmol, 2.5 eq. in 2 mL of $H_2O$) and DMSO (11.5 mL) was added. The reaction mixture was stirred overnight at 130° C. After 22 h reaction mixture was filtered through the pad of silica gel, the filtrate was concentrated under vacuum and purified by FC ($SiO_2$, hexane/EA 100:0→50:50) to give the desired product (0.307 g, Y: 27.2%) as a solid.

$^1$H NMR (300 MHz, $CDCl_3$) δ: 7.52 (d, J=5.4 Hz, 1H), 7.03 (dd, J=5.4, 3.9 Hz, 1H), 4.83 (s, 2H)

MS m/z: $[M+H]^+$ 238.65

Step 7: 5-chloro-N-(3-fluoro-4-iodopyridin-2-yl)-2-methoxypyridine-3-sulfonamide

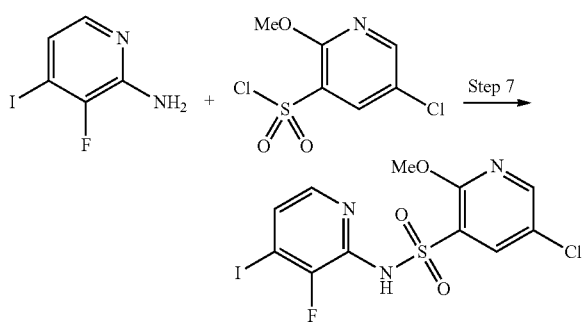

To a suspension of NaH (60% in oil, 1.02 g, 2.52 mmol, 4 eq.) in anh. THF (4.5 ml) was added 3-fluoro-4-iodopyridin-2-amine (Step 6, 150 mg, 0.63 mmol, 1 eq.) at 0° C. and the reaction mixture was stirred at r.t. for 1 h. Then it was cooled down to 0° C., and 5-chloro-2-methoxypyridine-3-sulfonyl chloride (Step 5, 168 mg, 0.69 mmol, 1.1 eq.) was added and the reaction mixture was stirred overnight at r.t. The reaction mixture was quenched with methanol and concentrated. The residue was dissolved in EA (15 ml) and washed with sat. $NaHCO_3$ solution (10 ml). The combined organic layers were dried over $MgSO_4$, filtered and concentrated under vacuum to give desired product as a brown solid (234 mg, Y: 84.0%).

$^1$H NMR (300 MHz, DMSO-$d_6$) δ: 12.03 (br, s, 1H), 8.43 (s, 1H), 8.20 (d, J=2.6 Hz, 1H), 7.53 (s, 1H), 7.37 (s, 1H), 3.86 (s, 3H)

MS m/z: $[M+H]^+$ 443.70

Step 8: N-{4-[2-(2-aminopyrimidin-5-yl)ethynyl]-3-fluoropyridin-2-yl}-5-chloro-2-methoxypyridine-3-sulfonamide

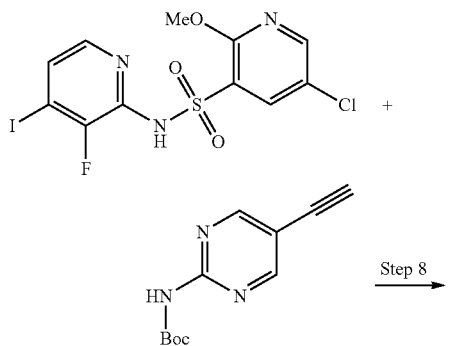

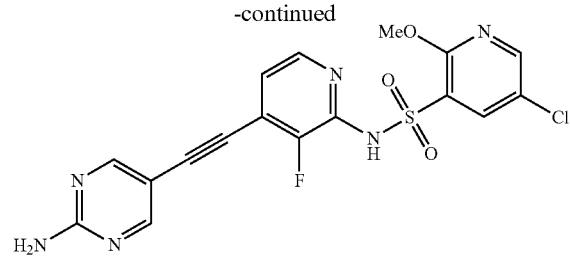

To a stirred solution of 5-chloro-N-(3-fluoro-4-iodopyridin-2-yl)-2-methoxypyridine-3-sulfonamide (Step 7, 100 mg, 0.230 mmol, 1 eq.), t-butyl N-(5-ethynylpyrimidin-2-yl)carbamate (Step 3, 59 mg, 0.27 mmol, 1.2 eq.) and $Cs_2CO_3$ (294 mg, 0.900 mmol, 4 eq.) in anhydrous DMSO (3 mL), under argon atmosphere, $PdCl_2[P(Cy)_3]_2$ (12 mg, 0.020 mmol, 0.07 Equiv.) was added and the reaction mixture was stirred in microwave for 1 h at 120° C. first and then for 1 h at 150° C. The reaction mixture was filtered through celite, the filtrate was concentrated under vacuum and purified by prep-HPLC to give 20.5 mg of beige solid. The solid product was treated with saturated solution of $NaHCO_3$ (4 mL), washed with $H_2O$ (4 mL) and dried under vacuum to give a beige solid product as a free base (15.8 mg, Y: 16.1%).

$^1$H NMR (400 MHz, DMSO-ds) δ: 8.44 (s, 2H), 8.19 (s, 1H), 8.07 (d, J=2.6 Hz, 1H), 7.52 (d, J=5.0 Hz, 1H), 7.23 (s, 2H), 6.47 (s, 1H), 3.83 (s, 3H)

LCMS (Method A) RT: 2.653 min

MS m/z: $[M-H]^-$ 432.77

Example 2: N-{4-[2-(2-aminopyrimidin-5-yl)ethynyl]-3-chloropyridin-2-yl}-5-chloro-2-methoxypyridine-3-sulfonamide

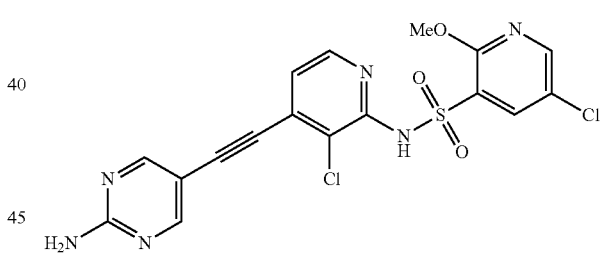

Step 1: 5-chloro-N-(3-chloro-4-iodopyridin-2-yl)-2-methoxypyridine-3-sulfonamide

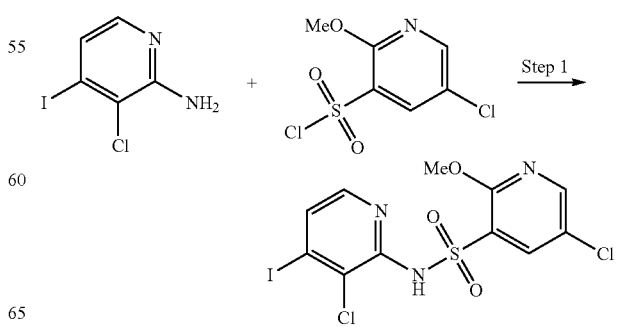

To a suspension of NaH (60% in mineral oil, 44 mg, 1.1 mmol, 4 eq.) in anh. THF (4.2 ml) cooled to 0° C., 3-chloro-4-iodopyridin-2-amine (70 mg, 0.28 mmol, 1 eq.) was added. The mixture was stirred at r.t. for 1 h and 5-chloro-2-methoxypyridine-3-sulfonyl chloride (Example 1, Step 5; 70 mg, 0.29 mmol, 1.05 eq.) was added. The reaction was continued overnight at r.t. MeOH (4 ml) was added and the mixture was evaporated to give a crude which was purified by FC (SiO$_2$, DCM/MeOH 100:0→90:10) to afford the desired product (59 mg, Y: 47%) as a light-yellow solid.

$^1$H NMR (300 MHz, CD$_3$OD) δ: 8.34 (d, J=2.6 Hz, 1H), 8.29 (d, J=2.6 Hz, 1H), 7.61 (d, J=5.7 Hz, 1H), 7.52 (d, J=5.6 Hz, 1H), 3.94 (s, 3H)

MS m/z: [M+H]$^+$ 459.70

Step 2: N-{4-[2-(2-aminopyrimidin-5-yl)ethynyl]-3-chloropyridin-2-yl}-5-chloro-2-methoxypyridine-3-sulfonamide

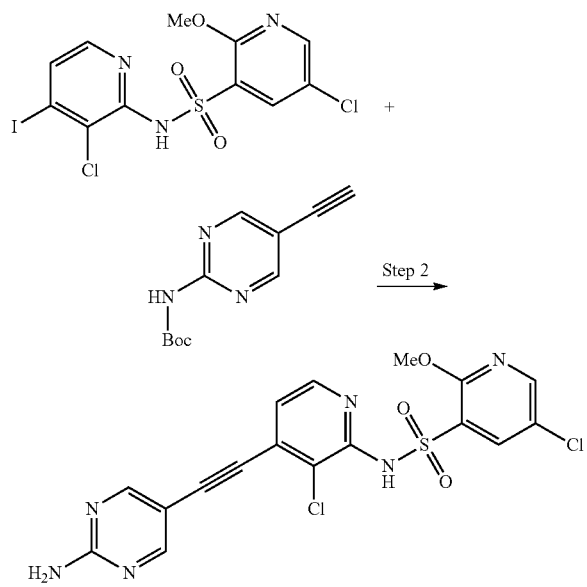

To a stirred solution of 5-chloro-N-(3-chloro-4-iodopyridin-2-yl)-2-methoxypyridine-3-sulfonamide (Step 1, 59 mg, 0.13 mmol, 1 eq.), t-butyl N-(5-ethynylpyrimidin-2-yl)carbamate (Example 1, Step 3; 34 mg, 0.15 mmol, 1.2 Equiv.) and Cs$_2$CO$_3$ (167 mg, 0.510 mmol, 4 Equiv.) in anhydrous DMSO (2 mL), under argon atmosphere, PdCl$_2$[P(Cy)$_3$]$_2$ (7 mg, 0.01 mmol, 0.07 Equiv.) was added and the reaction mixture was stirred in a microwave for 1 h at 120° C. first and then for 1 h at 150° C. The reaction mixture was filtered through celite, the filtrate was concentrated under vacuum and purified by prep-HPLC to give 13 mg of brown solid. The solid product was treated with a saturated solution of NaHCO$_3$ (2 mL), washed with H$_2$O (2 mL) and dried under vacuum to give a brown solid product as a free base (5.2 mg, Y: 9.0%).

$^1$H NMR (300 MHz, DMSO-ds) δ: 8.47 (s, 2H), 8.31 (s, 1H), 8.12 (s, 1H), 7.79 (s, 1H), 7.36 (s, 2H), 3.82 (s, 3H)

LCMS (Method A) RT: 2.793 min

MS m/z: [M−H]$^-$ 448.66

Example 3: 5-chloro-N-[3-fluoro-4-(2-{1H-pyrazolo[3,4-b]pyridin-5-yl}ethynyl)pyridin-2-yl]-2-methoxypyridine-3-sulfonamide

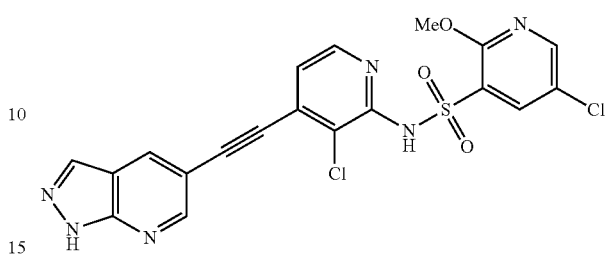

Step 1: 5-[2-(trimethylsilyl)ethynyl]-1H-pyrazolo[3,4-b]pyridine

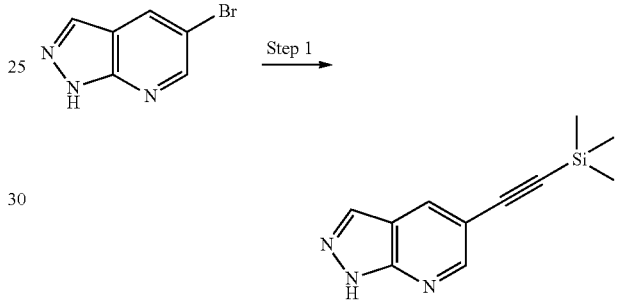

To a stirred solution of 3-bromo-1H-pyrazolo[3,4-b]pyridine (0.5 g, 2.32 mmol, 1 eq.) in ACN (25 ml) in a glass pressure reactor was added TMS acetylene (0.72 ml, 5.1 mmol, 2.2 eq.), copper (1) iodide (0.09 g, 0.46 mmol, 0.2 eq.) and TEA (1.31 ml, 13.9 mmol, 6 eq.). Argon was passed through the mixture for 15 minutes and PdCl$_2$(PPh$_3$)$_2$ (0.16 g, 0.23 mmol, 0.1 eq.) was added. The reactor was sealed and the mixture was stirred at 80° C. overnight. Afterward, the mixture was filtered through celite and ACN was evaporated to give a crude residue, which was dissolved in EA (25 ml) and washed with water (30 ml). The aqueous phase was additionally back-extracted with EA (15 ml). Combined organic layers were dried over Na$_2$SO$_4$, filtered and evaporated. The obtained residue was purified by column chromatography (SiO$_2$, EA/hexane 2:8) to afford the title product as a yellow solid (0.29 g, 59%).

$^1$H NMR (300 MHz, CDCl$_3$) δ: 8.79 (s, 1H), 8.28 (s, 1H), 7.28 (s, 1H), 0.31 (s, 9H)

MS m/z: [M+H]$^+$ 215.95

Step 2: 5-ethynyl-1H-pyrazolo[3,4-b]pyridine

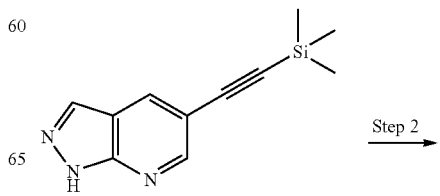

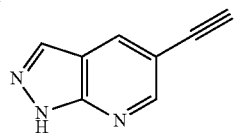

To a solution of the 5-[2-(trimethylsilyl)ethynyl]-1H-pyrazolo[3,4-b]pyridine (Step 1, 0.29 g, 1.3 mmol, 1 eq.) in methanol (6 ml) was added K₂CO₃ (0.55 g, 4 mmol, 3 eq.) and the resulting mixture was stirred at r.t. for 1.5 h under argon atmosphere. Methanol was evaporated in vacuo and the residue was triturated with water. The formed crystalline product was filtered and washed with water to give the desired product (0.126 g, Y: 68%).

$^{1}$H NMR (300 MHz, DMSO-$d_6$) δ: 13.76 (br. s, 1H), 8.59 (d, J=2.0 Hz, 1H), 8.42 (d, J=2.0 Hz, 1H), 8.18 (s, 1H), 4.29 (s, 1H)

MS m/z: [M+H]$^+$ 144.00

Step 3: 5-chloro-N-[3-fluoro-4-(2-{1H-pyrazolo[3,4-b]pyridin-5-yl}ethynyl)pyridin-2-yl]-2-methoxy-pyridine-3-sulfonamide

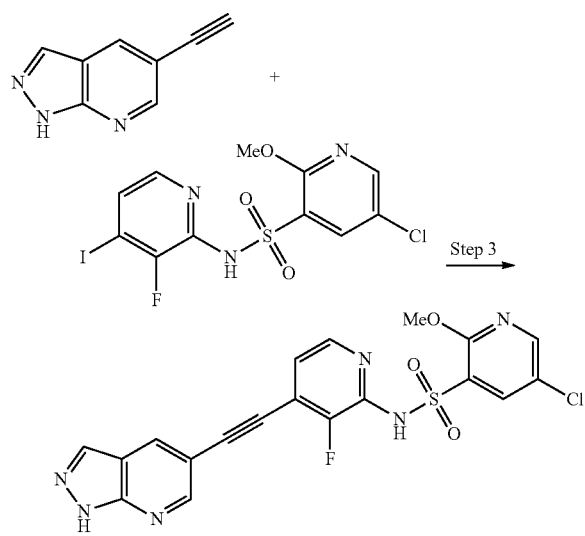

To a stirred solution of 5-chloro-N-(3-fluoro-4-iodopyridin-2-yl)-2-methoxypyridine-3-sulfonamide (Example 1, Step 7, 50 mg, 0.11 mmol, 1 eq.), 5-ethynyl-1H-pyrazolo[3,4-b]pyridine (Step 2, 19 mg, 0.14 mmol, 1.2 eq.) and Cs₂CO₃ (147 mg, 0.450 mmol, 4 eq.) in anh. DMSO (2 mL), under argon atmosphere, PdCl₂[P(Cy)₃]₂ (6 mg, 0.01 mmol, 0.07 eq.) was added and the reaction mixture was heated in a microwave for 1 h at 120° C. The reaction mixture was filtered through celite, the filtrate concentrated under vacuum and purified by prep-HPLC to give 15.8 mg of beige solid. The solid product was treated with sat. NaHCO₃ solution (3 mL), washed with H₂O (3 mL) and dried in vacuum to give the product as a beige solid (14.1 mg, Y: 27.3%).

$^{1}$H NMR (300 MHz, CD₃OD) δ: 14.02 (s, 1H), 8.74 (m, 1H), 8.60 (d, J=1.9 Hz, 1H), 8.45 (d, J=1.9 Hz, 1H), 8.22 (d, J=2.6 Hz, 1H), 8.17 (d, J=2.5 Hz, 2H), 7.68 (d, J=5.3 Hz, 1H), 6.77 (t, J=4.9 Hz, 1H), 3.95 (s, 3H)

LCMS (Method B) RT: 2.443 min

MS m/z: [M−H]$^-$ 456.74

Intermediate Synthesis for Example 10: N-{4-[2-(2-aminopyrimidin-5-yl)ethynyl]-3,5-difluoropyridin-2-yl}-5-chloro-2-methoxypyridine-3-sulfonamide

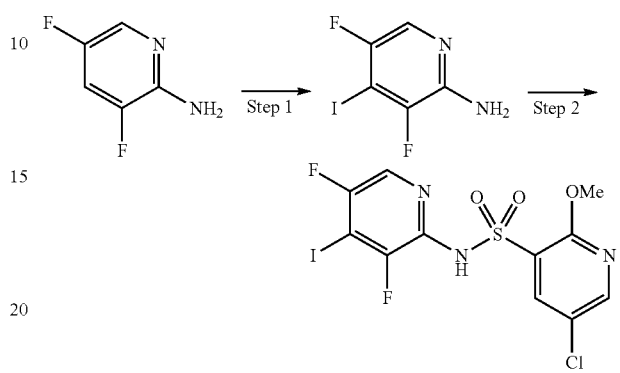

Step 1: 3,5-difluoro-4-Iodopyridin-2-amine n-Butyllithium (36 ml, 1.6 M solution in hexanes, 57 mmol, 2.5 eq.) was added dropwise to a solution of 2-amino-3,5-difluoropyridine (3.8 g, 23 mmol, 1 eq.) in THF (87 ml) at −78° C. The mixture was allowed to stir at that temperature for 1.5 hr, then a solution of iodine (17.4 g, 69 mmol, 3 eq.) in THF (27 ml) was added. The mixture was stirred at −78° C. for 15 min, then it was allowed to warm to rt. Saturated aqueous sodium thiosulfate was added, and the mixture was extracted with ethyl acetate. The combined organic layers were dried over sodium sulfate, filtered, and concentrated. The residue was purified by flash silica gel chromatography (0-15% ethyl acetate in hexane) to provide the title compound (3.4 g, 62% yield).

$^{1}$H NMR (300 MHz, CDCl₃) δ: 7.71 (s, 1H), 4.56 (s, 2H)

MS m/z: [M+H]$^+$ 256.90

Step 2: 5-chloro-N-(3,5-difluoro-4-iodopyridin-2-yl)-2-methoxypyridine-3-sulfonamide To a solution of 2-amino-3,5-difluoro-4-iodopyridine (1 g, 4.0 mmol, 1 eq.) in anhydrous pyridine (15 ml) in portions, the 2-methoxy-3-sulfonylchloro-5-chloropyridine (1.2 g, 4.6 mmol, 1.2 eq.) was added at 0-5° C. and the resulting mixture was stirred overnight at ambient temperature. Reaction progress was monitored by UPLC. Then the MeOH and all volatiles were evaporated in vacuo. The crude residue was purified by FC using 5 or 10% MeOH in DCM as an eluent to give the desired compound. (0.11 g, 24% yield).

$^{1}$H NMR (300 MHz, DMSO-d) δ: 11.49 (s, 1H), 8.52 (d, J=2.6 Hz, 1), 8.21 (d, J=2.6 Hz, 1), 8.03 (s, 1H), 3.93 (s, 3H)

MS m/z: [M+H]*461.70

Examples 4-11

Examples 4-11 were synthesized using methods analogous to those described above for Examples 1-3.

| Example | Structure | ¹HNMR (400 MHz, DMSO-d₆) δ | LCMS |
|---|---|---|---|
| 4 | 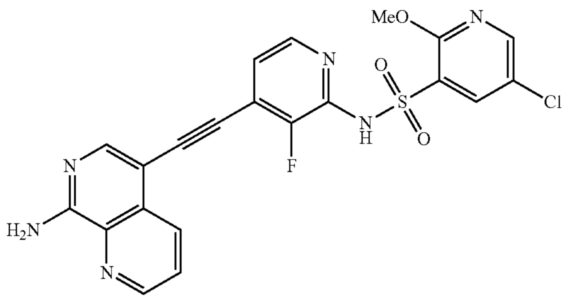 [SMILES: COc1ncc(Cl)cc1S(=O)(=O)Nc1nccc(C#Cc2cnc(N)c3ncccc23)c1F] | 12.06 (bs, 1H), 8.90 (dd, J = 4.2, 1.5 Hz, 1H), 8.47-8.35 (m, 2H), 8.27 (s, 1H), 8.21 (s, 1H), 7.91-7.80 (m, 2H), 7.75 (bs, 2H), 7.11 (bs, 1H), 3.87 (s, 3H) | Method C RT: 2.200 min m/z [M − H]⁻ 482.82 |
| 5 | 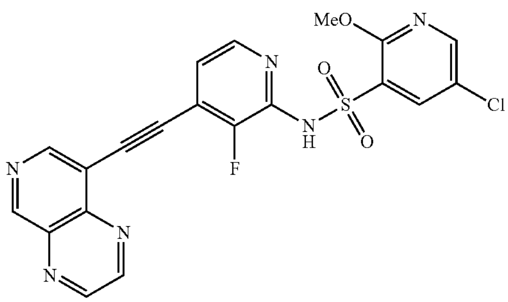 | 12.09 (bs, 1H), 9.58 (s, 1H), 9.31 (d, J = 1.6 Hz, 1H), 9.21 (d, J = 1.6 Hz, 1H), 9.15 (s, 1H), 8.35 (bs, 1H), 8.18 (bs, 1H), 7.79 (bs, 1H), 6.92 (bs, 1H), 3.88 (s, 3H) | Method B RT: 2.500 min m/z [M − H]⁻ 468.88 |
| 6 | 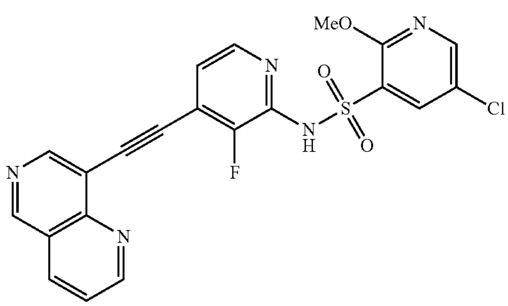 [SMILES: COc1ncc(Cl)cc1S(=O)(=O)Nc1nccc(C#Cc2cncc3cccnc23)c1F] | 12.04 (bs, 1H), 9.51 (s, 1H), 9.28 (dd, J = 4.3, 1.8 Hz, 1H), 9.07 (s, 1H), 8.71 (dd, J = 8.3, 1.8 Hz, 1H), 8.47 (bs, 1H), 8.25 (d, J = 2.1 Hz, 1H), 7.95 (bs, 1H), 7.85 (dd, J = 8.3, 4.3 Hz, 1H), 7.22 (bs, 1H), 3.91 (s, 3H) | Method B RT: 2.470 min m/z [M − H]⁻ 467.86 |
| 7 | 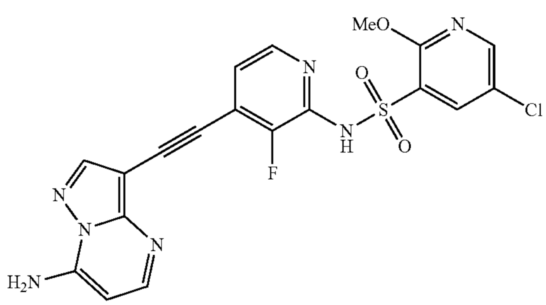 [SMILES: COc1ncc(Cl)cc1S(=O)(=O)Nc1nccc(C#Cc2cnn3c(N)ccnc23)c1F] | 12.01 (bs, 1H), 8.46 (s, 1H), 8.43 (s, 1H), 8.26-8.17 (m, 2H), 8.17-8.05 (m, 2H), 7.82 (bs, 1H), 6.99 (bs, 1H), 6.27 (d, J = 5.3 Hz, 1H), 3.87 (s, 3H) | Method C RT: 2.437 min m/z [M − H]⁻ 471.88 |
| 8 | 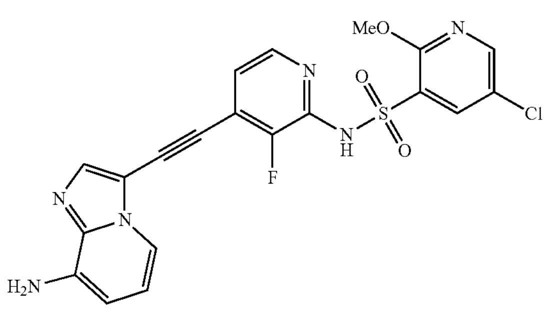 [SMILES: COc1ncc(Cl)cc1S(=O)(=O)Nc1nccc(C#Cc2cnc3c(N)cccn23)c1F] | 12.65 (bs, 1H), 8.33 (bs, 1H), 8.18-8.14 (m, 1H), 7.97 (s, 1H), 7.83 (d, J = 6.7 Hz, 1H), 7.73 (bs, 1H), 6.96-6.89 (m, 2H), 6.47 (d, J = 7.5 Hz, 1H), 5.90 (s, 2H), 3.86 (s, 3H) | Method C RT: 2.637 min m/z [M − H]⁻ 470.95 |

| Example | Structure | ¹HNMR (400 MHz, DMSO-d₆) δ | LCMS |
|---|---|---|---|
| 9 | 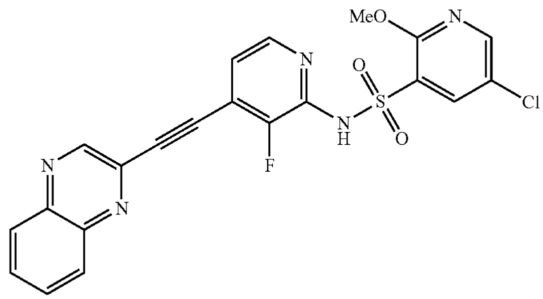 [SMILES: COc1ncc(Cl)cc1S(=O)(=O)Nc1nccc(C#Cc2cnc3ccccc3n2)c1F] | 12.01 (bs, 1H), 9.19 (s, 1H), 8.50 (d, J = 2.0 Hz, 1H), 8.27 (d, J = 2.4 Hz, 1H), 8.22-8.13 (m, 2H), 8.05-8.01 (m, 1H), 7.98 (dt, J = 6.2, 3.4 Hz, 2H), 7.36 (s, 1H), 3.92 (s, 3H) | Method D RT: 2.940 min m/z [M − H]⁻ 467.89 |
| 10 | 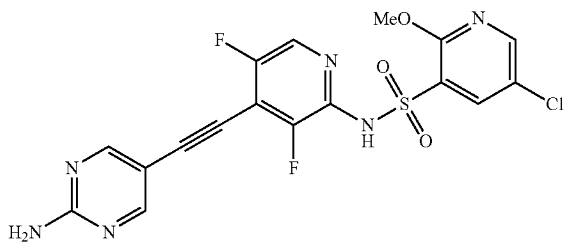 [SMILES: COc1ncc(Cl)cc1S(=O)(=O)Nc1ncc(F)c(C#Cc2cnc(N)nc2)c1F] | 11.52 (bs, 1H), 8.58-8.44 (m, 3H), 8.22 (d, J = 2.5 Hz, 2H), 7.46 (s, 2H), 3.93 (s, 3H) | Method D RT: 2.313 min m/z [M − H]⁻ 450.39 |
| 11 | 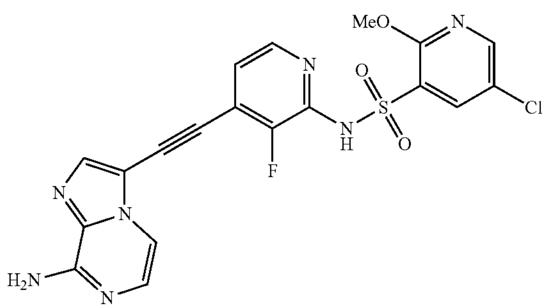 [SMILES: COc1ncc(Cl)cc1S(=O)(=O)Nc1nccc(C#Cc2cnc3c(N)nccn23)c1F] | 12.06 (bs, 1H), 8.43 (s, 1H), 8.22 (d, J = 2.5 Hz, 1H), 8.06 (s, 1H), 7.95-7.85 (m, 1H), 7.83 (d, J = 4.5 Hz, 1H), 7.47 (d, J = 4.5 Hz, 1H), 7.28-7.16 (m, 3H), 3.88 (s, 3H) | Method C RT: 1.940 min m/z [M − H]⁻ 471.93 |

Examples 12-17 were also synthesized using methods analogous to those described above for Examples 1-3.

| Example | Structure | ¹HNMR (400 MHz, DMSO-d₆) δ | LCMS |
|---|---|---|---|
| 12 | 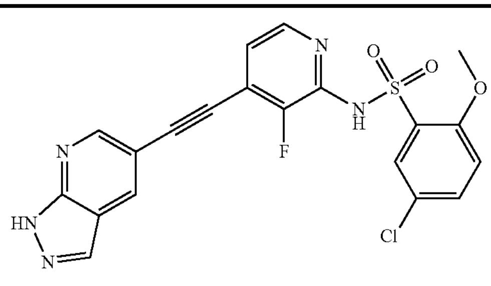 | 14.02 (s, 1H), 11.37 (s, 1H), 8.73 (d, J = 1.9 Hz, 1H), 8.59 (s, 1H), 8.25 (s, 1H), 7.92 (s, 1H), 7.81 (d, J = 2,4 Hz, 1H), 7.63 (s, 1H), 7.21 (d, J = 8.7 Hz, 2H), 3.79 (s, 3H) | Method C RT: 2.820 min m/z: [M + H]+ 458.00 |
| 13 | 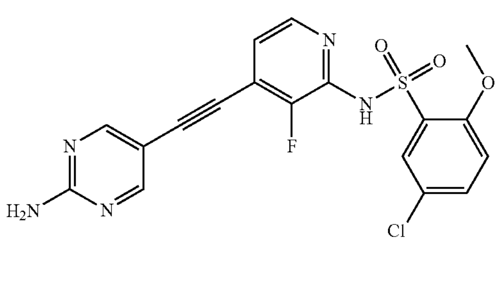 | 8.44 (s, 2H), 8.18 (s, 1H), 7.75 (d, J = 2.7 Hz, 1H), 7.54 (d, J = 5.0 Hz, 1H), 7.38 (dd, J = 8.7, 2.8 Hz, 1H), 7.24 (s, 2H), 7.01 (d, J = 8.8 Hz, 1H), 6.53-6.44 (m, 1H), 3.72 (s, 3H) | Method C RT: 2.587 min m/z: [M + H]+ 433.70 |

| Example | Structure | ¹HNMR (400 MHz, DMSO-d₆) δ | LCMS |
|---|---|---|---|
| 14 | 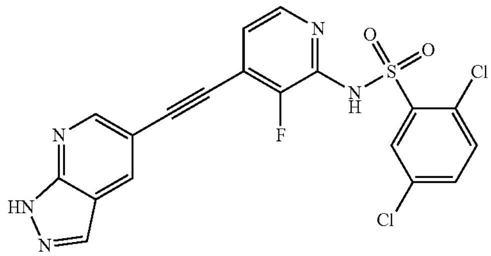 [SMILES: O=S(=O)(Nc1nccc(C#Cc2cnc3[nH]ncc3c2)c1F)c1cc(Cl)ccc1Cl] | 14.02 (s, 1H), 11.37 (s, 1H), 8.73 (d, J = 1.9 Hz, 1H), 8.59 (s, 1H), 8.25 (s, 1H), 7.92 (s, 1H), 7.81 (d, J = 2.4 Hz, 1H), 7.63 (s, 1H), 7.21 (d, J = 8.7 Hz, 2H), 3.79 (s, 3H) | Method C RT: 3.070 min m/z: [M − H]− 459.82 |
| 15 | 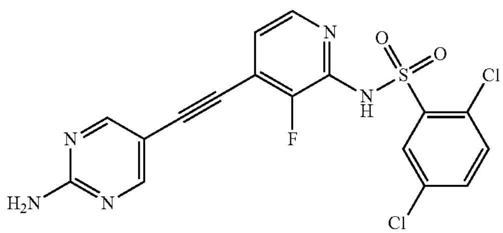 [SMILES: Nc1ncc(C#Cc2ccnc(NS(=O)(=O)c3cc(Cl)ccc3Cl)c2F)cn1] | 12.69 (s, 1H), 8.46 (s, 2H), 8.14 (s, 1H), 8.01 (d, J = 2.4 Hz, 1H), 7.67-7.57 (m, 1H), 7.55-7.46 (m, 2H), 7.30 (s, 2H), 6.69 (s, 1H) | Method B RT: 2.430 min m/z: [M + H]+ 437.98 |
| 16 | 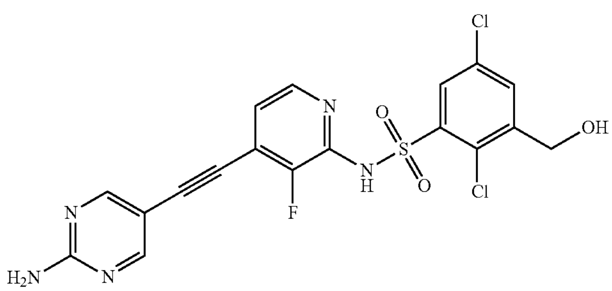 [SMILES: Nc1ncc(C#Cc2ccnc(NS(=O)(=O)c3cc(Cl)cc(CO)c3Cl)c2F)cn1] | 12.63 (s, 1H), 8.46 (s, 2H), 8.14 (s, 1H), 7.93 (d, J = 2.5 Hz, 1H), 7.59 (s, 2H), 7.29 (s, 2H), 6.64 (s, 1H), 5.59 (t, J = 5.6 Hz, 1H), 4.54 (d, J = 5.4 Hz, 2H) | Method C RT: 2.323 min m/z: [M + H]+ 467.93 |
| 17 | 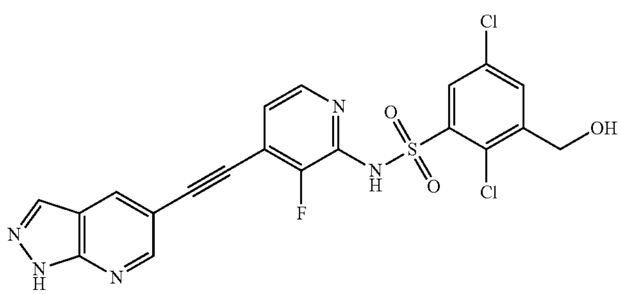 [SMILES: O=S(=O)(Nc1nccc(C#Cc2cnc3[nH]ncc3c2)c1F)c1cc(Cl)cc(CO)c1Cl] | 8.67 (s, 1H), 8.51 (s, 1H), 8.21 (s, 1H), 7.91 (d, J = 2.8 Hz, 1H), 7.52 (t, J = 3.9 Hz, 2H), 6.59-6.48 (m, 1H), 5.54 (s, 1H), 4.52 (s, 2H) | Method F RT: 2.637 min m/z: [M + H]+ 492.02 |

Example 18: S-chloro-N-[3-fluoro-4-(2-{1-methyl-1H-imidazo[4,5-c]pyridin-7-yl}ethynyl)pyridin-2-yl]-2-methoxypyridine-3-sulfonamide Step 1: S-chloro-N-{2-fluoro-3-[2-(trimethylsilyl)ethynyl]phenyl}-2-methoxypyridine-3-sulfonamide

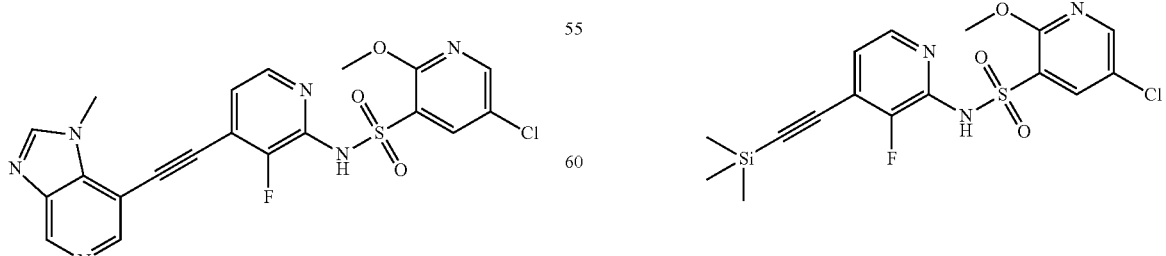

5-chloro-N-(3-fluoro-4-iodopyridin-2-yl)-2-methoxypyridine-3-sulfonamide (Example 1, step 7, 4.103 g, 8.971 mmol, 1.0 eq.), ethynyl(trimethyl)silane (2.481 ml, 17.946 mmol, 2.0 eq.), CuI (0.342 g, 1.796 mmol, 0.2 eq.) and triethylamine (6.878 ml, 49.347 mmol, 5.5 eq.) were mixed with anh. dimethylformamide (39.8 ml, 10.0 vol) in a 200 ml glass pressure reactor. Argon was bubbled through the mixture for 15 minutes and bis(triphenylphosphine)palladium(II)dichloride (0.316 g, 0.449 mmol, 0.05 eq.) was added. The mixture was stirred at 80° C. overnight. Reaction mixture was cooled to r.t. and filtered through a pad of Celite, and washed with MeOH. Filtrate was concentrated and the residue purified by FC (silica, hexane/ethyl acetate, 100:0 to 80:20) to afford 5-chloro-N-{3-fluoro-4-[2-(trimethylsilyl)ethynyl]pyridin-2-yl}-2-methoxypyridine-3-sulfonamide (2.79 g, 6.74 mmol, 71%) as a yellow solid.

$^1$H NMR (300 MHz, DMSO-d6) δ: 11.65 (s, 1H), 8.49 (s, 1H), 8.31-8.13 (m, 1H), 7.90 (s, 1H), 7.15 (s, 1H), 3.88 (s, 3H), 0.26 (s, 9H)

MS m/z: [M+H]$^+$ 413.85

Step 2: 5-chloro-N-(3-ethynyl-2-fluorophenyl)-2-methoxypyridine-3-sulfonamide

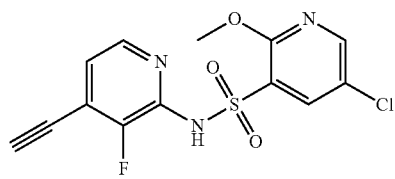 [SMILES: C#Cc1ccnc(NS(=O)(=O)c2cc(Cl)cnc2OC)c1F]

To a solution of 5-chloro-N-{3-fluoro-4-[2-(trimethylsilyl)ethynyl]pyridin-2-yl}-2-methoxypyridine-3-sulfonamide (2.79 g, 6.403 mmol, 0.95 eq.) in methanol anhydrous (22.32 ml, 8.0 vol) and anh. tetrahydrofuran (11.16 ml, 4.0 vol) at r.t. was added potassium fluoride (0.43 g, 7.402 mmol, 1.098 eq.). The mixture was stirred at r.t. for 1 hour and volatiles were evaporated. Residue was triturated with diethyl ether and dried to obtain 5-chloro-N-(4-ethynyl-3-fluoropyridin-2-yl)-2-methoxypyridine-3-sulfonamide (2.34 g, 6.847 mmol, 97%) as a light brown solid.

$^1$H NMR (300 MHz, DMSO-d$_6$) δ: 8.19 (d, J=2.7 Hz, 1H), 8.06 (d, J=2.7 Hz, 1H), 7.49 (d, J=5.1 Hz, 1H), 6.43 (dd, J=5.0, 4.2 Hz, 1H), 4.54 (d, J=0.8 Hz, 1H), 3.83 (s, 3H).

MS m/z: [M+H]$^+$ 341.85

Step 3: 5-chloro-N-[3-fluoro-4-(2-{1-methyl-1H-imidazo[4,5-c]pyridin-7-yl}ethynyl)pyridin-2-yl]-2-methoxypyridine-3-sulfonamide

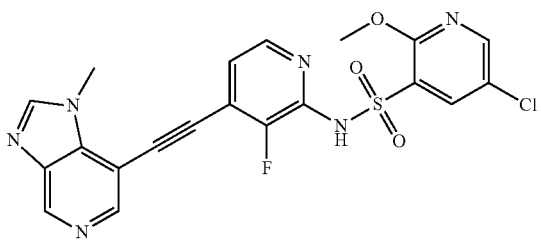 [SMILES: COc1ncc(Cl)cc1S(=O)(=O)Nc1nccc(C#Cc2cncc3ncn(C)c23)c1F]

5-chloro-N-(4-ethynyl-3-fluoropyridin-2-yl)-2-methoxypyridine-3-sulfonamide (84 mg, 0.25 mmol, 1 eq.) was dissolved in DMF (4 ml), then was added 7-bromo-1-methyl-1H-imidazo[4,5-c]pyridine (55 mg, 0.26 mmol, 1.05 eq.), CuI (9 mg, 0.05 mmol, 0.2 eq.) and triethylamine (0.19 ml, 1.35 mmol, 5.5 eq.). The solution was degassed with argon for 15 min and Pd(P(Cy)$_3$)$_2$Cl$_2$ (18 mg, 0.025 mmol, 0.1 eq.) was added. The vial was sealed and heated to 80° C. overnight. The reaction mixture was filtered through Celite, the filtrate concentrated under vacuum and purified by prep-HPLC to afford the title compound as a white solid (33 mg, 27%).

$^1$H NMR (400 MHz, DMSO-d6) δ: 11.99 (s, 1H), 9.06 (s, 1H), 8.61 (s, 1H), 8.52-8.41 (i, 2H), 8.25 (d, J=2.5 Hz, 1H), 7.98 (s, 1), 7.28 (s, 1H), 4.16 (s, 3H), 3.90 (s, 3H)

LCMS (Method C) RT: 2.097 min, MS m/z: [M+H]$^+$ 472.97

Examples 19-38 were synthesized using methods analogous to those described above for Example 18.

| Example | Structure | $^1$HNMR (400 MHz, DMSO-d$_6$) δ | LCMS |
|---|---|---|---|
| 19 | 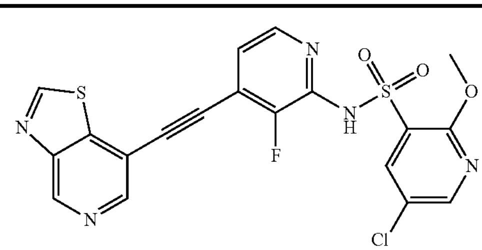 | 12.03 (s, 1H), 9.66 (s, 1H), 9.46 (s, 1H), 8.86 (s, 1H), 8.41 (s, 1H), 8.22 (s, 1H), 7.89 (s, 1H), 7.09 (s, 1H), 3.89 (s, 3H) | Method B RT: 2.737 min m/z: [M + H]+ 475.92 |
| 20 | 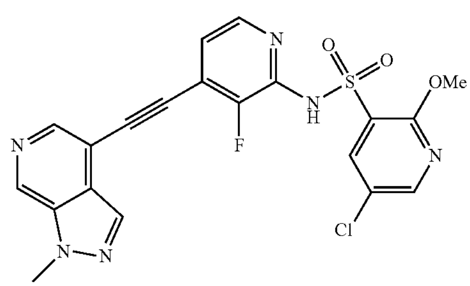 [SMILES: COc1ncc(Cl)cc1S(=O)(=O)Nc1nccc(C#Cc2cncc3c2cnn3C)c1F] | 9.25 (s, 1H), 8.46 (s, 1H), 8.33 (br, 2H), 8.29 (s, 1H), 8.20 (d, J = 2.6 Hz, 1H), 8.08 (d, J = 2.5 Hz, 1H), 7.58 (d, J = 5.1 Hz, 1H), 6.71-6.55 (m, 1H), 4.23 (s, 3H), 3.84 (s, 3H) | Method B RT: 2.643 min m/z: [M − H]− 470.93 |

-continued

| Example | Structure | ¹HNMR (400 MHz, DMSO-d₆) δ | LCMS |
|---|---|---|---|
| 21 | 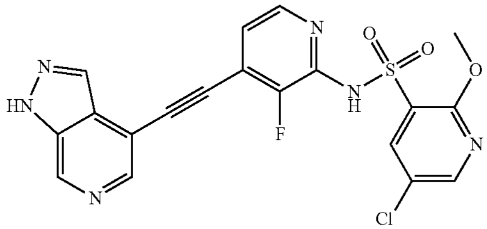 [SMILES: COc1ncc(Cl)cc1S(=O)(=O)Nc1nccc(C#Cc2cncc3[nH]ncc23)c1F] | 14.07 (s, 1H), 11.84 (s, 1H), 9.18 (s, 1H), 8.52 (s, 1H), 8.49 (s, 1H), 8.39 (s, 1H), 8.26 (s, 1H), 7.99 (s, 1H), 7.35 (s, 1H), 3.91 (s, 3H) | Method C RT: 2.620 min m/z: [M + H]+ 459.02 |
| 22 | 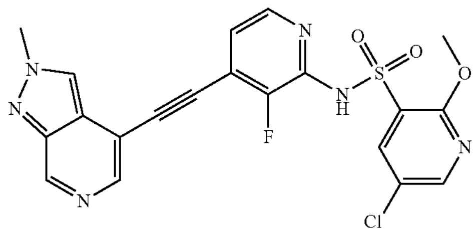 [SMILES: COc1ncc(Cl)cc1S(=O)(=O)Nc1nccc(C#Cc2cncc3nn(C)cc23)c1F] | 9.20 (s, 1H), 8.69 (s, 1H), 8.33 (s, 1H), 8.21 (d, J = 2.6 Hz, 1H), 8.09 (d, J = 2.7 Hz, 1H), 7.59 (d, J = 5.1 Hz, 1H), 6.67-6.56 (m, 1H), 4.30 (s, 3H), 3.85 (s, 3H) 2.607 min, MS m/z: [M + H]+ 472.98 | Method C RT: 2.607 min m/z: [M + H]+ 472.98 |
| 23 | 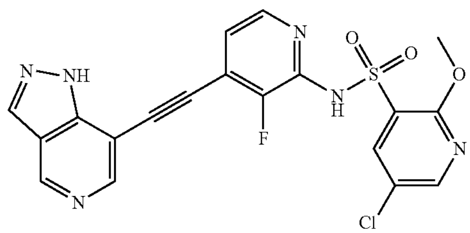 [SMILES: COc1ncc(Cl)cc1S(=O)(=O)Nc1nccc(C#Cc2cncc3cn[nH]c23)c1F] | 9.13 (s, 1H), 8.52 (s, 1H), 8.42 (s, 1H), 8.20 (d, J = 2.7 Hz, 1H), 8.09 (d, J = 2.7 Hz, 1H), 7.59 (d, J = 5.1 Hz, 1H), 6.71 (t, J = 4.6 Hz, 1H), 3.84 (s, 3H) | Method C RT: 2.030 min m/z: [M + H]+ 458.97 |
| 24 | 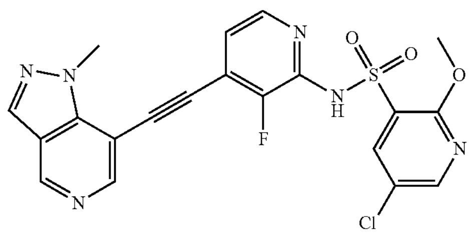 [SMILES: COc1ncc(Cl)cc1S(=O)(=O)Nc1nccc(C#Cc2cncc3cnn(C)c23)c1F] | 9.23 (s, 1H), 8.69 (s, 1H), 8.50 (d, J = 2.5 Hz, 1H), 8.45 (s, 1H), 8.26 (d, J = 2.6 Hz, 1H), 8.01 (s, 1H), 7.37 (d, J = 30.4 Hz, 1H), 4.38 (s, 3H), 3.91 (s, 3H) | Method C RT: 2.527 min m/z: [M + H]+ 473.01 |
| 25 | 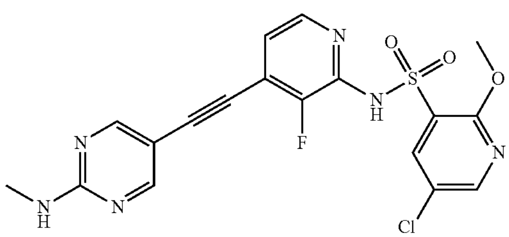 [SMILES: CNc1ncc(C#Cc2ccnc(NS(=O)(=O)c3cc(Cl)cnc3OC)c2F)cn1] | 8.56 (s, 1H), 8.49 (s, 1H), 8.41 (s, 1H), 8.23-8.15 (m, 1H), 7.88-7.74 (m, 2H), 6.96 (s, 1H), 3.86 (s, 3H), 2.85 (d, J = 4.8 Hz, 3H) | Method B RT: 2.563 min m/z: [M + H]+ 448.99 |
| 26 | 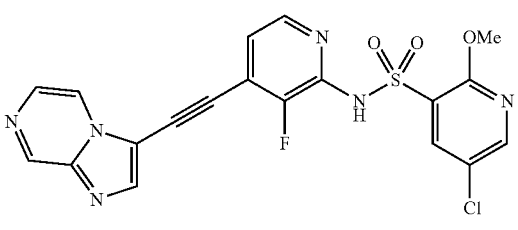 [SMILES: COc1ncc(Cl)cc1S(=O)(=O)Nc1nccc(C#Cc2cnc3cnccn23)c1F] | 11.93 (br, 1H), 9.26 (d,J = 1.4 Hz, 1H), 8.72 (dd, J = 4.5, 1.5 Hz, 1H), 8.49 (d, 1H), 8.38 (s, 1H), 8.25 (d, J = 2.5 Hz, 1H), 8.20 (d, J = 4.5 Hz, 1H), 7.98 (br s, 1H), 7.37 (br s, 1H), 3.90 (s, 3H) | Method C RT: 2.700 min m/z: [M + H]+ 459.01 |

-continued

| Example | Structure | ¹HNMR (400 MHz, DMSO-d₆) δ | LCMS |
|---|---|---|---|
| 27 | 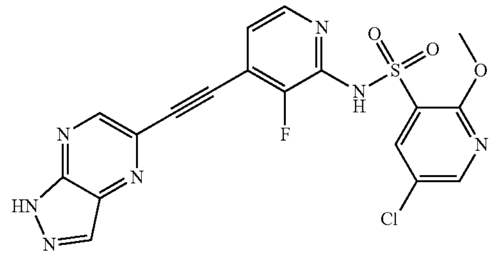 [SMILES: COc1ncc(Cl)cc1S(=O)(=O)Nc1nccc(C#Cc2cnc3[nH]ncc3n2)c1F] | 14.41 (s, 1H), 11.94 (s, 1H), 8.89 (s, 1H), 8.56 (s, 1H), 8.45 (s, 1H), 8.23 (s, 1H), 7.94 (s, 1H), 7.20 (s, 1H), 3.90 (s, 3H) | Method E RT: 2.883 min m/z: [M + H]+ 460.01 |
| 28 | 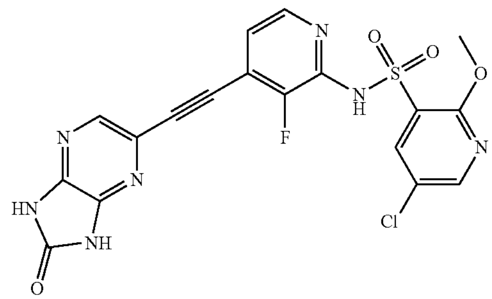 [SMILES: COc1ncc(Cl)cc1S(=O)(=O)Nc1nccc(C#Cc2cnc3[nH]c(=O)[nH]c3n2)c1F] | 11.95 (br, 2H), 8.19 (d, J = 2.7 Hz, 1H), 8.12 (s, 1H), 8.07 (d, J = 2.7 Hz, 1H), 7.54 (d, J = 5.1 Hz, 1H), 6.54-6.48 (m, 1H), 3.83 (s, 3H) | Method C RT: 2.413 min m/z: [M + H]+ 476.02 |
| 29 | 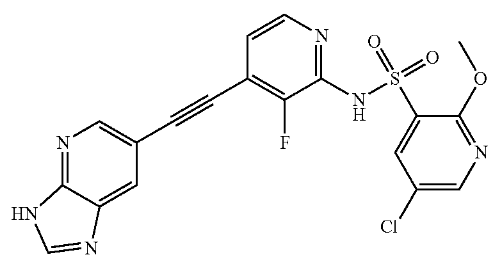 [SMILES: COc1ncc(Cl)cc1S(=O)(=O)Nc1nccc(C#Cc2cnc3[nH]cnc3c2)c1F] | 8.26 (d, J = 2.0 Hz, 1H), 8.20 (d, J = 2.6 Hz, 1H), 8.12 (s, 1H), 8.09 (d, J = 2.7 Hz, 1H), 7.90 (d, J = 2.1 Hz, 1H), 7.52 (d, J = 5.1 Hz, 1H), 6.55-6.50 (m, 1H), 3.85 (s, 3H) | Method C RT: 2.377 min m/z: [M − H]− 456.88 |
| 30 | 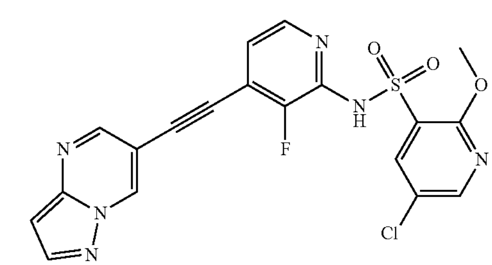 [SMILES: COc1ncc(Cl)cc1S(=O)(=O)Nc1nccc(C#Cc2cnc3ccnn3c2)c1F] | 12.04 (s, 1H), 9.62 (dd, J = 2.0, 0.9 Hz, 1H), 8.69 (d, J = 2.1 Hz, 1H), 8.39-8.29 (m, 2H), 8.17 (s, 1H), 7.76 (s, 1H), 6.86 (dd, J = 2.3, 0.9 Hz, 2H), 3.87 (s, 3H) | Method B RT: 2.730 min m/z: [M + H]+ 459.02 |
| 31 | 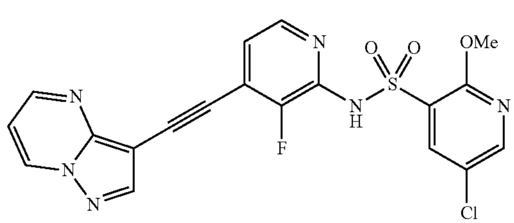 [SMILES: COc1ncc(Cl)cc1S(=O)(=O)Nc1nccc(C#Cc2cnn3cccnc23)c1F] | 11.84 (s, 1H), 9.66 (d, J = 2.3 Hz, 1H), 8.71 (d, J = 2.1 Hz, 1H), 8.49 (d, J = 2.6 Hz, 1H), 8.38 (d, J = 2.3 Hz, 1H), 8.25 (d, J = 2.6 Hz, 1H), 7.98 (s, 1H), 7.23 (s, 1H), 6.91-6.85 (m, 1H), 3.90 (s, 3H) | Method B RT: 2.723 min m/z: [M + H]+ 459.00 |

| Example | Structure | ¹HNMR (400 MHz, DMSO-d₆) δ | LCMS |
|---|---|---|---|
| 32 | 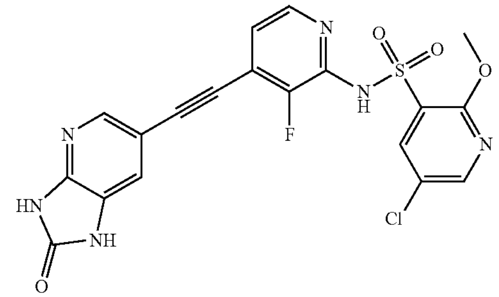 [SMILES: COc1ncc(Cl)cc1S(=O)(=O)Nc1nccc(C#Cc2cnc3[nH]c(=O)[nH]c3c2)c1F] | 11.05 (br, 3H), 8.19 (d, J = 2.7 Hz, 1H), 8.07 (d, J = 2.7 Hz, 1H), 8.04 (s, 1H), 7.51 (d, J = 5.1 Hz, 1H), 7.25 (s, 1H), 6.52-6.44 (m, 1H), 3.83 (s, 3H) | Method C RT: 2.380 min m/z: [M + H]+ 475.02 |
| 33 | 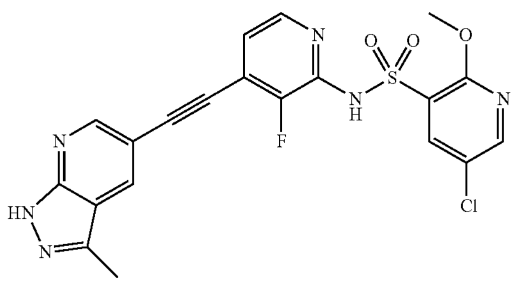 [SMILES: COc1ncc(Cl)cc1S(=O)(=O)Nc1nccc(C#Cc2cnc3[nH]nc(C)c3c2)c1F] | 13.36 (s, 1H), 8.63 (d, J = 2.0 Hz, 1H), 8.52 (d, J = 2.0 Hz, 1H), 8.20 (d, J = 2.6 Hz, 1H), 8.09 (d, J = 2.7 Hz, 1H), 7.55 (d, J = 5.1 Hz, 1H), 6.54 (dd, J = 5.1, 4.2 Hz, 1H), 3.84 (s, 3H), 2.53 (s, 3H) | Method B RT: 2.577 min m/z: [M + H]+ 473.02 |
| 34 | 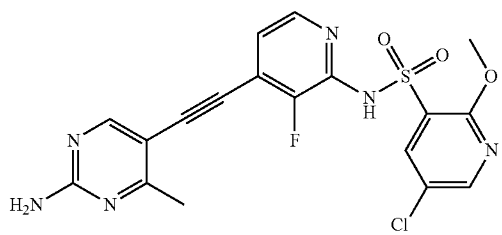 [SMILES: COc1ncc(Cl)cc1S(=O)(=O)Nc1nccc(C#Cc2cnc(N)nc2C)c1F] | 8.33 (s, 1H), 8.19 (d, J = 2.7 Hz, 1H), 8.07 (d, J = 2.7 Hz, 1H), 7.51 (d, J = 5.1 Hz, 1H), 7.12 (s, 2H), 6.50-6.43 (m, 1H), 3.84 (s, 3H), 2.41 (s, 3H) | Method C RT: 2.657 min m/z: [M + H]+ 449.01 |
| 35 | 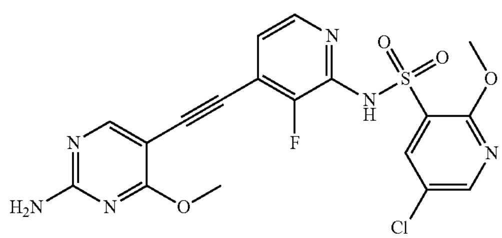 [SMILES: COc1nc(N)ncc1C#Cc1ccnc(NS(=O)(=O)c2cc(Cl)cnc2OC)c1F] | 8.21 (s, 1H), 8.18 (d, J = 2.7 Hz, 1H), 8.07 (d, J = 2.7 Hz, 1H), 7.49 (d, J = 5.1 Hz, 1H), 7.15 (s, 2H), 6.45-6.38 (m, 1H), 3.91 (s, 3H), 3.83 (s, 3H) | Method C RT: 2.613 min m/z: [M + H]+ 464.95 |
| 36 | 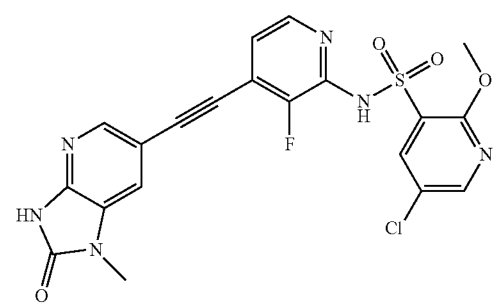 [SMILES: COc1ncc(Cl)cc1S(=O)(=O)Nc1nccc(C#Cc2cnc3[nH]c(=O)n(C)c3c2)c1F] | 8.19 (d, J = 2.7 Hz, 1H), 8.08 (d, J = 2.7 Hz, 1H), 7.83 (d, J = 2.1 Hz, 1H), 7.48 (d, J = 5.1 Hz, 1H), 6.86 (s, 1H), 6.45 (t, J = 4.7 Hz, 1H), 3.84 (s, 3H), 3.17 (s, 3H). | Method C RT: 2.633 min m/z: [M + H]+ 489.03 |

-continued

| Example | Structure | 1HNMR (400 MHz, DMSO-d6) δ | LCMS |
|---|---|---|---|
| 37 | 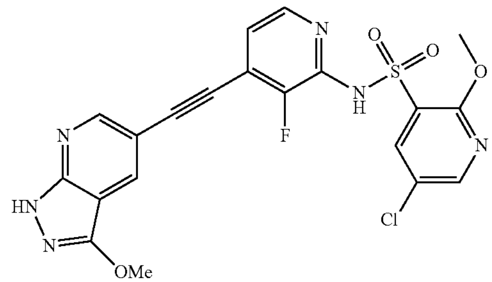 [SMILES: COc1ncc(Cl)cc1S(=O)(=O)Nc1nccc(C#Cc2cnc3[nH]nc(OC)c3c2)c1F] | 12.93 (s, 1H), 8.65 (s, 1H), 8.36 (s, 1H), 8.30-8.18 (m, 1H), 8.18-8.01 (m, 1H), 7.74-7.48 (m, 1H), 6.80-6.52 (m, 2H), 4.03 (s, 3H), 3.85 (s, 3H) | Method G RT: 2.457 min m/z: [M + H]+ 488.93 |
| 38 | 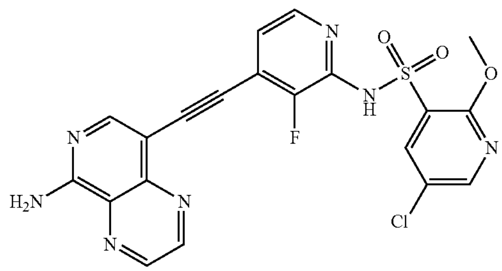 [SMILES: COc1ncc(Cl)cc1S(=O)(=O)Nc1nccc(C#Cc2cnc(N)c3nccnc23)c1F] | 9.14 (d, J = 2.0 Hz, 1H), 8.88 (d, J = 2.0 Hz, 1H), 8.39 (s, 1H), 8.19 (d, J = 2.7 Hz, 1H), 8.08 (d, J = 2.7 Hz, 1H), 7.85 (s, 2H), 7.52 (d, J = 5.1 Hz, 1H), 6.56-6.45 (m, 1H), 3.84 (s, 3H) | Method C RT: 2.410 min m/z: [M + H]+ 486.00 |

Biological and Pharmacokinetic Testing (a) GCN2 Enzyme Inhibition (10 μM and 300 μM Assays)

Assay Protocol Overview:

The inhibitory activity of the Example compounds towards GCN2 enzyme was measured according to the description below, using a LanthaScreen TR-FRET (Time Resolved Fluorescence Resonance Energy Transfer) Kinase Activity assay distributed by ThermoFisher Scientific.

The full-length human GCN2 enzyme (UniProt accession number Q9P2K8) was used for all experiments (Carna Bioscience). The TR-FRET pair was composed of GFP-eIF2α and LanthaScreen Terbium-labeled anti-peIF2α (pSer52) Antibody.

Each example compound was dissolved in DMSO (0.15 mM) and dispensed in a 384-well plate by a D300 dispenser (Tecan) to a final concentration range 3000-0.13 nM using the logarithmic dilution mode in 2 replicates. Full inhibition (3000 nM commercial reference inhibitor) and DMSO vehicle control wells were also included on the same plate. All volumes were normalized to the final DMSO concentration of 2% of the reaction volume. Next, 5 μL of H$_2$O was added to each well of the plate.

The enzyme mixture was prepared to obtain the following concentrations:

GCN2—30 nM unloaded tRNA—0.3 nM

HEPES (pH=7.0)—100 mM

MgCl$_2$—20 mM; MnCl$_2$—10 mM

The mixture was applied by adding 5 μL to each well of the plate. The enzyme and the tested compound were then incubated at room temperature for 20 min while shaking at 450 rpm.

The substrate mixture was prepared to obtain the following concentrations:

GFP-eIF2α—240 nM

ATP—900 μM or 30 μM

HEPES (pH=7.0)—50 mM

MgCl$_2$—10 mM

MnCl$_2$—5 mM.

The mixture was applied by adding 5 μL to each well of the plate. Thus, the final concentrations of the 15 μL reaction mixture were as follows:

GCN2—10 nM unloaded tRNA—0.1 nM

GFP-eIF2α—80 nM

ATP—300 μM or 10 μM

HEPES (1 M, pH=7.0)—50 mM

MgCl$_2$—10 mM

MnCl$_2$—5 mM.

The reaction was allowed to proceed at room temperature for 30 min while shaking at 450 rpm.

The antibody mixture was prepared to obtain the following concentrations:

Na$_2$EDTA·2H$_2$O—40 mM, in TR-FRET Dilution Buffer (Life technologies)

Tb—anti-peIF2a antibodies—4 nM.

The mixture was applied by adding 15 μL to each well. The plate was then incubated at room temperature for 60 min while shaking at 450 rpm and then read using Tecan Spark reader using specific TR-FRET filters.

The analysis of the GFP/Tb fluorescence results was conducted with GraphPad Prism to determine IC$_{50}$ for each of the example compounds using 4-parameter model: log (inhibitor) vs. response-variable slope. IC$_{50}$ and K, values were calculated in the usual way. The assay was carried out between 1 and 15 times. The results in the table below are the mean results from replicate assays for the compound in question, where applicable.

Results:

TABLE 1

| Example # | GCN2 IC50 (nM) 10 uM ATP | GCN2 Ki (nM) 10 uM ATP | GCN2 IC50 (nM) 300 uM ATP | GCN2 Ki (nM) 300 uM ATP |
|---|---|---|---|---|
| 1 | 7.2 | 2.3 | 103.2 | 1.6 |
| 2 | 8.1 | 2.6 | 79.0 | 1.2 |
| 3 | 3.5 | 1.1 | 26.5 | 0.6 |
| 4 | 2.9 | 0.9 | 17.6 | 0.3 |
| 5 | 7.8 | 2.5 | 185.6 | 2.8 |
| 6 | 6.7 | 2.1 | 49.3 | 0.8 |
| 7 | 7.9 | 2.5 | 104.7 | 1.6 |
| 8 | 9.9 | 3.1 | 335.3 | 5.1 |
| 9 | 7.5 | 2.4 | 112.2 | 1.7 |
| 10 | 19.1 | 6.1 | 57.3 | 0.9 |
| 11 | 2.3 | 0.7 | 71.8 | 1.1 |
| 12 | | | 256.8 | 3.9 |
| 13 | | | 610.6 | 9.3 |
| 14 | | | 235.5 | 3.6 |
| 15 | | | 465.3 | 7.1 |
| 16 | | | 110.8 | 1.7 |
| 17 | | | 59.0 | 0.9 |
| 18 | 11.3 | 3.6 | 364.8 | 5.6 |
| 19 | 12 | 3.8 | 384.4 | 5.9 |
| 20 | 14.5 | 4.6 | 324.3 | 4.9 |
| 21 | | | 158.0 | 2.4 |
| 22 | | | 98.6 | 1.5 |
| 23 | | | 38.3 | 0.6 |
| 24 | | | 168.9 | 2.6 |
| 25 | | | 110.0 | 1.7 |
| 26 | | | 556.0 | 8.5 |
| 27 | | | 224.6 | 3.4 |
| 28 | | | 174.1 | 2.7 |
| 29 | | | 653.8 | 10.0 |
| 30 | | | 160.4 | 2.4 |
| 31 | | | 98.9 | 1.5 |
| 32 | | | 48.1 | 0.7 |
| 33 | 4.2 | 1.3 | 21.7 | 0.3 |
| 34 | | | 658.4 | 10.0 |
| 35 | | | 328.1 | 5.0 |
| 36 | | | 182.5 | 2.8 |
| 37 | | | 20.9 | 0.3 |
| 38 | | | 55.3 | 0.8 |

The results in Table 1 show that the compounds of the invention are potent inhibitors of GCN2.

(b) Kinetic Solubility

Assay Protocol Overview:

The kinetic solubility assay investigates a solubility based on the amount of material which remains in solution after a precipitation process. Compounds for kinetic solubility test are prepared as 10 mM stock solutions in DMSO. Assay is performed using Multiscreen Vacuum Manifold. A buffer of interest (in standard protocol PBS buffer at pH=7.4 is used) is spiked with stock solution and incubated for 90 minutes at room temperature. After that time solution/suspension is filtrated. The concentration of each compound is determined on the base of prepared calibration curve using UV-VIS spectrophotometry method. The assay is made in triplicate.

Buffer of interest: 0.24 g of $KH_2PO_4$, 1.44 g of $Na_2HPO_4$, 0.2 g of KCl and 8 g NaCl and dissolve in 1 L distilled $H_2O$; adjust pH to appropriate value (pH 7.4). 190 μl of buffer of interest was dispensed into the wells of a 96 well filter plate, followed by 10 μl of compound (10 mM stock solution in DMSO). The plate was shaken gently at room temperature for 90 minutes at 500 rpm using a BioSan, Plate Shaker-Thermostat, PST-60 HL-4. After 90 minutes, the plate was filtered using a vacuum manifold and vacuum pump. 100 μl of each filtrate and 100 μl acetonitrile was transferred to a 96 well UV-visible light transparent plate and the UV-visible absorption spectrum was measured using a Biotek Synergy 2 multiplate reader from 250-500 nm, interval range 10 nm. The amount of test compound was calculated using a calibration curve prepared by serial dilution of compounds in equivalent amounts of DMSO and acetonitrile.

Results:

| Compound | Kinetic Solubility (μg/ml) |
|---|---|
| Example 1 | 217.8 |
| Example 2 | 225.7 |
| Example 3 | 229.4 |
| Example 4 | 29.5 |
| Example 5 | 222.8 |
| Example 6 | 40.3 |
| Example 7 | 215.9 |
| Example 8 | 213.7 |
| Example 9 | 134.5 |
| Example 10 | 137.8 |
| Example 11 | 216.4 |
| Example 12 | 160.8 |
| Example 13 | 109.4 |
| Example 14 | 24.7 |
| Example 15 | 223.9 |
| Example 16 | 218.2 |
| Example 17 | 250.4 |
| Example 18 | 24.3 |
| Example 19 | 102.6 |
| Example 20 | 70.6 |
| Example 21 | 221.1 |
| Example 22 | 229.3 |
| Example 23 | 220.5 |
| Example 24 | 80.3 |
| Example 25 | 207.9 |
| Example 26 | 241.1 |
| Example 27 | 225.0 |
| Example 28 | 231.2 |
| Example 29 | 230.8 |
| Example 30 | >244.9 |
| Example 31 | >243.4 |
| Example 32 | 40.1 |
| Example 33 | 245.3 |
| Example 34 | 237.5 |
| Example 35 | N/A |
| Example 36 | 239.7 |
| Example 37 | >244.4 |
| Example 38 | 244.9 |

Comparative Data 1

The inhibitory activity towards the GCN2 enzyme and the kinetic solubility of certain comparator compounds were measured using the assays described above, and they were compared with a compound of the current invention. The results are shown below.

| Compound Number | Structure | GCN2 IC$_{50}$ (10 μM ATP) nM | GCN2 Ki (10 μM ATP) nM | GCN2 IC$_{50}$ (300 μM ATP) nM | GCN2 Ki 300 μM ATP) nM | Kinetic Solubility (μg/ml) |
|---|---|---|---|---|---|---|
| Comp Ex 1 | 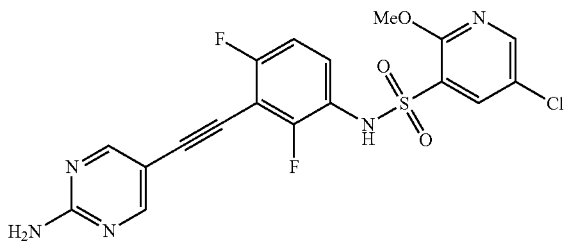 [SMILES: COc1ncc(Cl)cc1S(=O)(=O)Nc1ccc(F)c(C#Cc2cnc(N)nc2)c1F] | 5.9 | 1.9 | 59.2 | 0.9 | 4.7 |
| Comp Ex 2 | | 10.0 | 3.2 | 70.7 | 1.1 | 50.8 |
| Comp Ex 3 | | 249 | 78.9 | 8221 | 125.5 | 227.3 |
| Example 1 | 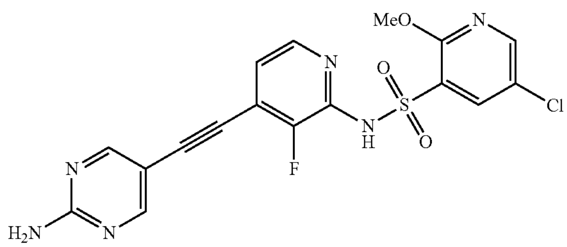 | 7.2 | 2.3 | 103.2 | 1.6 | 217.8 |

Comparative Example 1 was disclosed in Fujimoto, J. et al (2019) ACS Med. Chem. Lett 10(1), 1498-1503 where it was named Compound 6e. In Nakamura et al (2018), PNAS, 115 (33), 7776-7785, it was named GCN2iB. Comparative Example 2 was disclosed in WO 2018/030466 where it was named Example compound 123. Comparative Example 3 was disclosed in WO 2018/030466 where it was named Reference compound 120.

It is seen that the compound of Example 1 is superior to the comparator compounds, in that it has both strong GCN2 inhibitory activity and good kinetic solubility as measured in the assay. It is especially noteworthy that Comparative Example 3 which has a pyridine ring at its centre, but in a different orientation from the compounds of the invention (such as Example 1), has extremely poor activity at GCN2.

Comparative Data 2

The inhibitory activity towards the GCN2 enzyme and the kinetic solubility of a further comparator compound were measured using the assays described above, and they were compared with a compound of the current invention. The results are shown below.

| Compound Number | Structure | GCN2 IC$_{50}$ (10 μM ATP) nM | GCN2 Ki (10 μM ATP) nM | GCN2 IC$_{50}$ (300 μM ATP) nM | GCN2 Ki (300 μM ATP) nM | Kinetic Solubility (μg/ml) |
|---|---|---|---|---|---|---|
| Comp Ex 4 | | 5.8 | 1.8 | 31.0 | 0.5 | 3.9 |
| Example 3 | 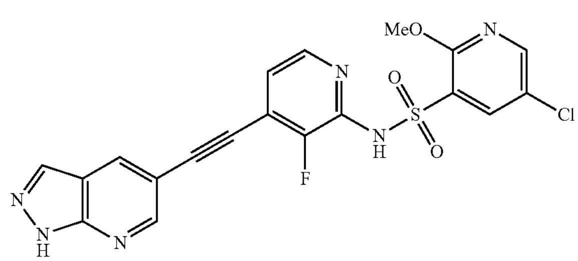 [SMILES: COc1ncc(Cl)cc1S(=O)(=O)Nc1nccc(C#Cc2cnc3[nH]ncc3c2)c1F] | 3.5 | 1.1 | 26.5 | 0.6 | 229.4 |

Comparative Example 4 was disclosed in WO 2018/030466 where it was named Example compound 5. It is seen that the compound of Example 3 is superior to the comparator compound, in that it has both strong GCN2 inhibitory activity and good kinetic solubility as measured in the assay.

Kinase Selectivity Assay:

Compounds were tested for activity against off-target kinases using the KINOMEscan™ screening platform, which employs a novel and proprietary active site-directed competition binding assay to quantitatively measure interactions between test compounds and hundreds of human kinases and disease relevant mutant variants. KINOMEscan™ assays do not require ATP and thereby report true thermodynamic interaction affinities.

For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Results:

| Example No: | % Control | Kinases |
|---|---|---|
| Example 1 | <0.5% | GCN2 |
|  | <5% | None |
| Example 3 | <0.5% | GCN2 |
|  | <5% | MEK5 |

For comparison, the equivalent findings for Comparative Example 1, as reported in Nakamura et al (2018), PNAS, 115 (33), 7776-7785, (where it was named GCN2iB) were as follows:

| Compound: | % Control | Kinases |
|---|---|---|
| Comp Ex 1 | <0.5% | GCN2 |
|  | <5% | MAP2K5, STK10, ZAK |

The invention claimed is:

1. A compound of formula

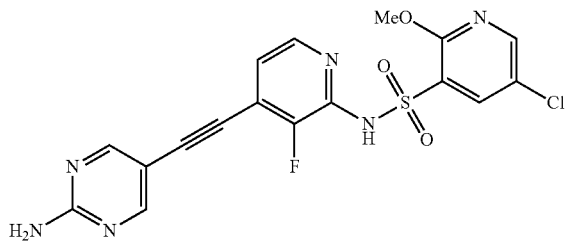

or a pharmaceutically acceptable salt thereof.

2. A compound N-{4-[2-(2-aminopyrimidin-5-yl)ethynyl]-3-fluoropyridin-2-yl}-5-chloro-2-methoxypyridine-3-sulfonamide or a pharmaceutically acceptable salt thereof.

3. A pharmaceutical composition comprising the compound according to claim 1 and at least one pharmaceutically acceptable carrier or excipient.

4. The pharmaceutical composition according to claim 3, wherein said composition further comprises at least one further therapeutic agent.

5. The pharmaceutical composition according to claim 4, wherein the further therapeutic agent is 1-asparaginase or a proteasome inhibitor.

\* \* \* \* \*